(12) United States Patent
Minassian

(10) Patent No.: US 8,349,557 B2
(45) Date of Patent: Jan. 8, 2013

(54) COMPOSITIONS AND METHODS FOR DIAGNOSIS OF AUTOPHAGIC VACUOLAR MYOPATHY

(75) Inventor: Berge A. Minassian, Toronto (CA)

(73) Assignee: The Hospital for Sick Children, Toronto (CA)

(*) Notice: Subject to any disclaimer, the term of this patent is extended or adjusted under 35 U.S.C. 154(b) by 357 days.

(21) Appl. No.: 12/477,555

(22) Filed: Jun. 3, 2009

(65) Prior Publication Data

US 2009/0311704 A1 Dec. 17, 2009

Related U.S. Application Data

(60) Provisional application No. 61/059,317, filed on Jun. 6, 2008.

(51) Int. Cl.
C07H 21/04 (2006.01)
C12Q 1/68 (2006.01)

(52) U.S. Cl. ...... 435/6.1; 435/6.11; 435/6.12; 435/91.1; 435/91.2; 536/23.1; 536/24.3

(58) Field of Classification Search ............ None
See application file for complete search history.

(56) References Cited

U.S. PATENT DOCUMENTS 5,545,527 A 8/1996 Stevens et al.

OTHER PUBLICATIONS

Ramachandran et al. ( Cell, 137, vol. 235-246, 2009).*
Mazarei, Clinical Genetics, pp. 114-115, 2009.*
Ioannidis (Nature Genetics, vol. 29, pp. 306-309, Nov. 2001).*
Hirschhorn et al. (Genetics in Medicine. vol. 4, No. 2, pp. 45-61, Mar. 2002).*
Oprea, Iulia, "Unraveling the causative defects in x-linked myopathy with excessive autophagy", Thesis, Institute of Medical Science, University of Toronto, 2009.*
Auranen, M. et al., "X-linked vacuolar myopathies: two separate loci and refined genetic mapping," *Ann Neurol* 47:666-669 (2000).
Bechet, D. et al., "Lysosomal proteolysis in skeletal muscle," *Int J Biochem Cell Biol* 37:2098-2114 (2005).
Bowman, E. J. et al., "Bafilomycins: a class of inhibitors of membrane ATPases from microorganisms, animal cells, and plant cells," *Proc Natl Acad Sci USA* 85:7972-7976 (1988).
Chabrol, B. et al., "X-linked myopathy with excessive autophagy: a clinicopathological study of five new families," *Neuromuscul Disord* 11:376-388 (2001).
Cuervo, A. M. et al., "A receptor for the selective uptake and degradation of proteins by lysosomes," *Science* 273:501-503 (1996).
Cuervo, A. M. et al., "Unique properties of lamp2a compared to other lamp2 isoforms," *J Cell Sci* 113(Pt 24), 4441-4450 (2000).
Di Blasi, C. et al., "Abnormal Lysosomal and Ubiquitin-Proteasome Pathways in 19p13.3 Distal Myopathy," 56(1):133-8 (2004).
Drose, S. et al., "Bafilomycins and concanamycins as inhibitors of V-ATPases and P-ATPases," *J Exp Biol* 200:1-8 (1997).

Drose, S. et al., "Inhibitory effect of modified bafilomycins and concanamycins on P- and V-type adenosinetriphosphatases," *Biochemistry* 32:3902-3906 (1993).
Eskelinen, E. L. et al., "Role of LAMP-2 in lysosome biogenesis and autophagy," *Mol Biol Cell* 13:3355-3368 (2002).
Forgac, M., "Vacuolar ATPases: rotary proton pumps in physiology and pathophysiology," *Nat Rev Mol Cell Biol* 8:917-929 (2007).
Frattini, A. et al., "Defects in TCIRG1 subunit of the vacuolar proton pump are responsible for a subset of human autosomal recessive osteopetrosis," *Nat Genet* 25:343-346 (2000).
Gietz, R. D. et al., "Applications of high efficiency lithium acetate transformation of intact yeast cells using single-stranded nucleic acids as carrier," *Yeast* 7:253-263 (1991).
Hayashi, M. et al., "Vacuolar H(+)-ATPase localized in plasma membranes of malaria parasite cells, Plasmodium falciparum, is involved in regional acidification of parasitized erythrocytes," *J Biol Chem.*
Hurtado-Lorenzo, A. et al., "V-ATPase interacts with ARNO and Arf6 in early endosomes and regulates the protein degradative pathway," *Nat Cell Biol* 8:124-136 (2006).
Huynh, K. K. et al., "LAMP proteins are required for fusion of lysosomes with phagosomes," *Embo J* 26:313-324 (2007).
Kalimo, H. et al., "X-linked myopathy with excessive autophagy: a new hereditary muscle disease," *Ann Neurol* 23:258-265 (1988).
Karet, F. E. et al., "Mutations in the gene encoding B1 subunit of H+-ATPase cause renal tubular acidosis with sensorineural deafness," *Nat Genet* 21:84-90 (1999).
Kornak, U. et al., "Impaired glycosylation and cutis laxa caused by mutations in the vesicular H+-ATPase subunit ATP6V0A2," *Nat Genet* 40:32-34 (2008).
Ludwig, J. et al., "Identification and characterization of a novel 9.2-kDa membrane sector-associated protein of vacuolar proton-ATPase from chromaffin granules," *J Biol Chem* 273:10939-10947 (1998).
Macdonald, R. D. et al., "Experimental chloroquine myopathy," *J Neuropathol Exp Neurol* 29:479-499 (1970).
Malkus, P. et al., "Role of Vma21p in assembly and transport of the yeast vacuolar ATPase," *Mol Biol Cell* 15:5075-5091 (2004).
Manolson, M. F. et al., "The a3 isoform of the 100-kDa V-ATPase subunit is highly but differentially expressed in large (>or=10 nuclei) and small (<or=nuclei) osteoclasts," *J Biol Chem* 278:49271-49278.

(Continued)

*Primary Examiner* — Jeanine A Goldberg
(74) *Attorney, Agent, or Firm* — Vedder Price P.C.; Ajay A. Jagtiani

(57) ABSTRACT

Transmembrane V-ATPase proton pump complexes regulate pH of extracellular space or intracellular compartments of cells. V-ATPase complexes are ubiquitous in cells across species. A human orthologue of yeast vma21, LOC203547 (VMA21), is likely involved in the assembly of the V-ATPase. Hypomorphic mutations of VMA21 are identified from XMEA patients. Methods to diagnose and/or distinguish between different forms of vacuolar or vacuolated myopathy in an individual or patient are provided based either on the sequence of the VMA21 gene and/or the level and/or activity of the V-ATPase complex. Compositions of the present invention may comprise DNA, RNA, or protein molecules corresponding to all or a portion of VMA21 and including one or more of the mutations in VMA21 identified. Cultured cells or cell lines having one or more mutations in the VMA21 gene derived from patients having a form of vacuolar or vacuolated myopathy are provided.

3 Claims, 26 Drawing Sheets

OTHER PUBLICATIONS

Massey, A. C. et al., "Consequences of the selective blockage of chaperone-mediated autophagy," *Proc Natl Acad Sci USA* 103:5805-5810 (2006).
Minassian, B. et al., "Narrowing in on the causative defect of an intriguing X-linked myopathy with excessive autophagy," *Neurology* 59:596-601 (2002a).
Minassian, B.A. et al., "X-linked myopathy with excessive autophagy," In: Structural and Molecular Basis of Skeletal Muscle Diseases, G. Karpati, ed. (Zurich, ISN Neuropath Press), pp. 145-147; and Villanova, M. et al., "X-linked vacuolated myopathy: complement membrane attack complex on surface membrane of injured muscle fibers," *Ann Neurol* 37:637-645 (1995).
Mizushima, N. "Autophagy: process and function," *Genes Dev* 21:2861-2873 (2007).
Mizushima, N. et al., "Autophagosome formation in mammalian cells," *Cell Struct Funct* 27:421-429 (2002).
Mizushima, N. et al., "In vivo analysis of autophagy in response to nutrient starvation using transgenic mice expressing a fluorescent autophagosome marker," *Mol Biol Cell* 15:1101-1111 (2004).
Nishino, I. et al., "Primary LAMP-2 deficiency causes X-linked vacuolar cardiomyopathy and myopathy (Danon disease)," *Nature* 406:906-910 (2000).
Nishino, I., "Autophagic vacuolar myopathy," *Semin Pediatr Neurol* 13:90-95 (2006).
Ochotny, N. et al., "Effects of human a3 and a4 mutations that result in osteopetrosis and distal renal tubular acidosis on yeast V-ATPase expression and activity," *J Biol Chem* 281:26102-26111 (2006).
Paroutis, P. et al., "The pH of the secretory pathway: measurement, determinants, and regulation," *Physiology (Bethesda)* 19:207-215 (2004).
Salvador, N. et al., "Import of a cytosolic protein into lysosomes by chaperone-mediated autophagy depends on its folding state," *J Biol Chem* 275:27447-27456 (2000).
Sambade, M. et al., "The yeast vacuolar proton-translocating ATPase contains a subunit homologous to the *Manduca sexta* and bovine e subunits that is essential for function," *J Biol Chem* 279:17361-17365 (2004).
Sennoune, S. R. et al., "Vacuolar H+-ATPase in human breast cancer cells with distinct metastatic potential: distribution and functional activity," *Am J Physiol Cell Physiol* 286:C1443-1452 (2004).
Servidei, S. et al., "A distinctive autosomal dominant vacuolar neuromyopathy linked to 19p13," *Neurology* 53(4):830-7 (1999).
Shacka, J. J. et al., "Bafilomycin A1 inhibits chloroquine-induced death of cerebellar granule neurons," *Mol Pharmacol* 69:1125-1136 (2006).
Smith, A. N. et al., "Mutations in ATP6N1B, encoding a new kidney vacuolar proton pump 116-kD subunit, cause recessive distal renal tubular acidosis with preserved hearing," *Nat Genet* 26:71-75 (2000).
Stauber, W. T. et al., "Inhibition of lysosomal function in red and white skeletal muscles by chloroquine," *Exp Neurol* 71:295-306 (1981).
Tanaka, Y. et al., "Accumulation of autophagic vacuoles and cardiomyopathy in LAMP-2-deficient mice," *Nature* 406:902-906 (2000).
Taussky, H. H. et al., "A microcolorimetric method for the determination of inorganic phosphorus," *J Biol Chem* 202:675-685 (1953).
Villard, L. et al., "Linkage of X-linked myopathy with excessive autophagy (XMEA) to Xq28," *Eur J Hum Genet* 8:125-129 (2000).
Yamamoto, A. et al., "Bafilomycin A1 prevents maturation of autophagic vacuoles by inhibiting fusion between autophagosomes and lysosomes in rat hepatoma cell line, H-4-II-E cells," *Cell Struct Funct* 23:33-42.

* cited by examiner

| | | |
|---|---|---|
| *GGGTCACTGG CATCGAGTCT GGAACAGTCA TTCTCAGCAA GAGCTCTTTG*<br>*AACTCTGACA TTCTCTAGTT TTACGGACTC GG* | 150315745 | Alt x1<br>(SEQ ID NO: 8) | gtgagtgt tttaactcct
cccagctgcc aagggcttga cttcctacca ctgcgggcag taattaatga 150315845
ggcatttatt tgctcaagta gtggcgaaat aatgcgcact gcttttttgt 150315895
gttgtcgtcg gcggaatacg ctcagttgcc tag

| | | |
|---|---|---|
| *CACCACA GCCCTCTGGC*<br>*TGGTAGTCCC TCTTCGCGGC TCAATG¹CTC GGGTCTCCTT GCGGCCCCCA*<br>*GCTCAGCGAC CGAGACGCAG ACGAGGACCA GTGTTCACGC GAGTTCAGGG*<br>*GGCGGCGTAG CCGCCGCCCG CCCAGGAGGA CCATG² TTGCG CGGCAAGTCC*<br>*CGGCTCAACG TGGAGTGGCT GGGCTACTCG CCAGGCCTGC TCCTCGAGCA*<br>*CAGGCCCCTC CTGGCAGGGC GCACGCCGCG GAGCCACCGC CG* | 150315995<br>150316045<br>150316095<br>150316145 | Alt x2<br>(SEQ ID NO: 9) | gtaagtca
tgtgagcgcc cgccccccgcg ccggcaacag ccctgcgtcg ctgcggcgcg 150316245
ccgcgccgcg ccgcgcctgc gtactgtggc ccgccgcccg cgcgcaacgg 150316295
gcacttccgg cgcgaacggg cacttccggc gcgaaccgct acttccggtg 150316345
cgaaccgcct cggccgt

| | | |
|---|---|---|
| *TCCCTCGCGG AGCTTACTGA GCGCGGCCGC CGAGCCCAGC TCCGCCGCCG*<br>*AGCGCCTGTG CCGGCACGGC TACACCATGG AGCGCCCGGA TAAGGCGGCG*<br>*CTGAACGCAC TGCAGCCTCC TGAGTTCAG* | 150316412<br>150316462 | Exon x1<br>(SEQ ID NO: 2) |

| | | |
|---|---|---|
| gtag<br>ccctgagcgg ggcctggacc gcgaggcgga ctggccccag cctggagcag<br>ggcttgaggg aaggccctag ctgaatgggt gggcgtgagg tctggacccc<br>gggggacctgg cctcagggaa ggggggcgggg aaagcaggtt ggagcctgag<br>acgtctaaac tcccggcccc gaactttcgc tcgggaacaa gggatccggg<br>gtcatgggga ataggtcagt gggccttcag ctcatgctcc tatcctagca<br>ctttctctcg ctgtgtctat attgcagtct ctttcattac cgcagggtca<br>gccttctgag gacaggaatg cagtctcctt catctccgtt ttccctaggg<br>ggcctgcata gtcggggctt aataaatgtt tgctgtatga atgaaggagt<br>agaagggaat agtccctgg tgtgagattg cttcacttgg ggaatcagta<br>agatagaggc tggtgactga gttgaaggaa tgtatgagag agcaggtggt<br>tctggcccac cccagtaggc aagggagtgg tgagggagtt agctatcatt<br>cgttaagacc tactgtatgc caggctcagt gcacgtgctt tacatacatt<br>gtcagaattc ttaatttctc taactgcttg atttcccaat tttgaagagg<br>atgcagttga gggtaagtga cttgaaactg agggtgagtg attacagaat<br>taggcgacaa agttagtatg taattgaagc taacgtttga ccaagctcac<br>tgactccaaa gcccacgatc tttggagctc tgtgatgcct tctctttccg<br>acagggtcat tgtgagtttt ttttttttt tttaactttt tattttaggt<br>tcatgagtac atgcgcaggt tgttatata ggtaaactgc atgtcacggg<br>ggcttggcgt acaggtaatt ttgtcaccca ggtaataagc atagtacccg<br>ataggcgttt tttctgattc tctccctcct cccagcctcc accctcaagt<br>agaccgcact gtctgttgtt cctctcctag tgtccatctg ttcttgttgt<br>ttagttccca cttatgagaa cgtgcagtat ttggttttct tttcctgtct | 150316545<br>150316595<br>150316645<br>150316695<br>150316745<br>150316795<br>150316845<br>150316895<br>150316945<br>150316995<br>150317045<br>150317095<br>150317145<br>150317195<br>150317245<br>150317295<br>150317345<br>150317395<br>150317445<br>150317495<br>150317545<br>150317595 | (SEQ ID NO: 5) |

FIG.3A-1

```
taatttgctt agaataatgg cttccagctc cagtcatgtt gctgcaaagg 150317645
acatgatctc attcttttt  atggctgcat agtgttccat ggtgtatatg 150317695
taccgcattt tctttatcca gcctcaatgt gggttttttt ttaattattc 150317745
atttatgaga ataccaacat attttatta  gatacactta cagcatagtc 150317795
cttctagact gattctggtt tcctaatgga atttgcagtg aaatcttgac 150317845
tgtgggagaa agaattcctg ttgtcttact tgctacaaaa gggaatgtgg 150317895
taggctctgt ctgctcaatg ttggctgcag aagtttgtat gaagtgggaa 150317945
aactaggtgg tgttataaat ggaggcagat taaggttcat cctgaacttt 150317995
ttcctttgtg tgaggacaac tttaattcca gcctttctca ttcctcactt 150318045
ctaacaaatc tctgctcagt aacacccaaa gatacatagg ataaatcaat 150318095
tgaatagcat cagttgcttt gtcttggata agccactgat tttacccaag 150318145
gtggcttgca tcagcaaaac caacagctct tgtggctgga atccagggag 150318195
aaaatgtcct ataaacagta gaggaagttt gctagttttc aaagtttgt  150318245
atgtacactt tgacttaatg cttagtccca tattagtgag gtcacaacac 150318295
agaaaagtag tcacatttt  gaagtttgag gtaaagagag aagtgagaag 150318345
gaattagcca taaattatta aggtatgctg tgtatagatt gtgtgggggc 150318395
tagaaattaa tatgtagaaa ggttatattt gggtggtggg attataggtg 150318445
attttgttta ctttaaaaca tttttatggt gttatatcat cttttcaata 150318495
ataaacttt  taaaagccag accagataat agatactcaa gagaggtcat 150318545
gtaaagaaca aaacaatcag ttaacacttc ctttctgttc ctttaacaag 150318595
ttagataatc tgaaagttgc attcctaaaa catactttt  tactcaccat 150318645
agaaacacca aagtcaagtg cttttttag  ggtgcacaaa agaattggcc 150318695
aattagtgac tctttgtatt ttttgtagat tctccactgc agacactcat 150318745
actcttcatg aggattacac aataaatttc tctaaaaatt tactagtagg 150318795
aaacagttta agggagctta tgtatattaa atgagagttg tatagctcag 150318845
taataaccaa aatgaggcct gctaaaagat gatccattta agtaccaaaa 150318895
gaaaatatta gaactttttt ttttacagca gtaagcattt aatttctcac 150318945
acatgtgcag agcatgtgat caagaaatag gcatgaggtt agttatattt 150318995
aatatatatt ttactcaatg tttttgtggg tttttttgttc aggttctttt 150319045
taaataaatt tcattgtgta tatttgaggt tcataacatg atgttatggc 150319095
atacatatag taaaatgatt actatggtga agcagattaa tatatctgtc 150319145
atctcacata cttttgtgtg tgtgtgacca gaggcagcta aaatcttatt 150319195
tacaaaagtc cctaatacca tgcaactttta ttgcctatag tcctcttgta 150319245
cattagatat ctcacttgtt aatccatata tctactgctt tgtgtccttt 150319295
gatgtatatc ttcctatttc ctcccctcca gcctcccacc cccaccgcca 150319345
tggtaactac tgttttattc tctgtccctg tgtagttgac cgttgacctt 150319395
ttttttttt  ttttaaagat tccacatata agtgagctca tgtagtattc 150319445
gtctttctgc gtttggctta ttttacttaa catgtcttcc aggtccatcc 150319495
atgttgtggc aaatggcaga tgtcctcttt taaggctgaa taaaatattc 150319545
ccttgtatat atacactacg gtttctttat tttgtctgtc tacatacacg 150319595
taggttgttt tcaaatcttg gctattgtga ataatgctgc aatgaacatg 150319645
gaagtgcaga tatttttacg aggtagtgat ttcatctcct ttgcttatat 150319695
tccagaagag agattgctgg gctgtgtggt agttctattt ttaatttctt 150319745
taggaactgt tttccataat ggctgtacca gtctacattt ccagtcacaa 150319795
tgtagtaggg tttcttttc  tccacacttt tacaaacatt tgttatcact 150319845
tgcctttttg ataatagctg tccttagaag tgtgaggtta tatctcatag 150319895
tggttttgat ttgcatttcc ctgatgattt agtgatgttg agcacattt  150319945
catttatctc ttggccattt ttatgtcttt ggagaaatgt ctgtccagct 150319995
gttgtccata ttttaatcag gtggtttttc tgctgagttg taagagttct 150320045
```

FIG.3A-2

```
ttataaattt tggggtatta acccottaca agataggtgg ttcgcaaata 150320095
tgttttccta gtctgtaagc tgccttttca ttttgttgat tgtttccttt 150320145
gcagtacaga agcttttag tttgatgcaa gccgctttat tttttctttt 150320195
gtagcctgag cttttggtgt gatatccaaa aaatcattac tgaggccaat 150320245
gttaaggacc tttccctctg tgttcttta tgtcttaaaa ctttatatct 150320295
ttatgtttta gttattttat ccattttggg ttgattttg tttatggtgt 150320345
aagagtccag tttttttctt tgcatgtaga aatcctgttt tcccagtacc 150320395
acttattgaa gggactgtcc tttccccatt gtgttcctct taacacccct 150320445
gtcgaagatt agttggccat atatgtttgg atttatttct gggctctatt 150320495
ctgtttcatt gttatatgtt tctgttttta tgccaatacc atattgtttt 150320545
gattactata actgtaatat tttaaatcag aaagtgtgat gcttacaact 150320595
ttttcaatgt tgctttggct atttggggct ttttgtggtt ctgtatgatg 150320645
aattttagga ttgttttct attaatga agaatgctac tgtaattttg 150320695
atagagattg tgttatatct gtatgttgct ttgggtgctg tagacatttc 150320745
aacagtatta attcttccaa tccatgaaca caggatatct ttacatttat 150320795
ttgtgtcatc ttcaatttct ttcatcagtg ttttatactt ttcagtgtac 150320845
aagtcactca tcgccttggt taaatttatt cctaagtttc tttttttttg 150320895
aaatagagtc ttgctctgtc acccaggcca gagtaaagtg ccccaatcac 150320945
tgctcactgc agccttgacc tctggggctc aaacaatcct cccacttcag 150320995
cctcttgagt agctgagatt acaggcacgt gccaccatgc ccagcgaatt 150321045
atcaaaattt ttttttgtag aggtgggtt ttgctgtgtt acctaggctt 150321095
gcgtcaaact cccggcctca agcctcagcc ttcccaaagt gctgggatta 150321145
caggcatgag ccactgagcc tggccccctaa gtattttttt ttaatgctat 150321195
tataaatgag attgttttct tgatttcttt ttcagctcag taaaggatgc 150321245
ggaagtttgt caagtgcttt ttctgcatca actgagatga tcctacttgg 150321295
tcataatata taatcttttt gatgtattgg ttttgttgt ttgtgacaga 150321345
gtcttgctct gttgcccaga ctggagtgtg atttggctc attgcaacct 150321395
ctgcctccca ggatcaaggg attcttgtgc cttggcctcc caagtagctg 150321445
ggactatagg cacacgccac cactctcagc taattttgt attttagta 150321495
gagactgggt tttgccatgt tggccaggct gatctcgaac tcctggcctc 150321545
aagtgatccg cctgcctcgg cctcccaaag tgctgggatt acaggtgtga 150321595
gccaccacac ctggcctgat tattgttgaa tttggtttga aatatgtta 150321645
ttgaggaatt ttgcaccagt gttcatcagt gatgttgtcc tgtagttttc 150321695
ttgctgtgtc tgtctggctt aggtatcaag gtgattggag cctcttaaaa 150321745
cgtgtttgga agtattccct ctagctcgat ttttcaccca taacagaagt 150321795
tcctattcca gctggggagg gcgcactggt ccgttcgccc tgcctaccctc 150321845
cttcagtggt ctggtgtctg gtgctggtgg tcagggttgc tgcacgggct 150321895
cagggactgg tgtggcagtg gcttccctgg gccaaagctc tgatcccagt 150321945
gggggagggc acgctggtgc gtcggctcca cctggttagt ttgctggtcc 150321995
actgtctggt gctggaggac aggaggctgg cagctttccc agatgcaagc 150322045
tccgattcca gcgggagagg gcacactgct ccacctgtgg tgcctgccga 150322095
gttccctggt ctggtgtccg gtgctggtgg tcagggttgc tgcgtgggct 150322145
cagggaccag tgtgacagtg gcttccctgg gcaaaagctc tgattccagt 150322195
gtgggagggt gcacaggtgt gtctgcctcg ttagttccct ggtccactgt 150322245
ctcatgctgg aggacagcaa gctggtcgct tccgtgacg gaagctctga 150322295
ttccagcaaa agagggcgcg ctgatccacc catggtgcct gctgcgttcc 150322345
cagctctggt gtctggtgct ggtggcacg gttgccgcat gggttgggca 150322395
ctggtgccgc tgtccgccgt ggcttccctg ggtaaaagct ccagttccag 150322445
aggcaggggc actgagtttc ttcacttagt ttgttcaccc agcttgttgg 150322495
```

```
cagttgatct gaggtgccct gacgcttcgt cttacactgg atatgaatga    150322545
cagtccctaa aggtggtgta taatcttcat gttccagctc aagaaattcc    150322595
cactacccac agctggttct ctaggatctt cggattacga gtccctgcct    150322645
gtgatcttcc tcctgcatag catctcattt gtggatgttt atagtttcag    150322695
ggacataaga gcgtttggat atgactgtgc aggttctgat tttctctttg    150322745
tttactttat tccag
```

```
AAATG AAAGCTCATT AGCATCTACA CTGAAGACGC                    150322795    Exon x2
TCCTGTTCTT CACAGCTTTA ATGATCACTG TTCCTATTGG GTTATATTTC    150322845    (SEQ ID NO: 3)
ACAACTAAAT CTTACATATT TGAAG
```

```
gtaat cttagaccca ttaaaacaag
atgttttccc ccaatttaag attctgtgct tttatgacct ctttatatct    150322945
ttaaactggg tattcttatt ttttctttgt ttagcttttc aaaaaatcat    150322995
attgctcata atgagtcttt atgaaataac ttattgtttc agcttgacag    150323045
ttttcctatg gttttctgtg aaatagcttg caaatccttt ctcttagtac    150323095
cttttaaaga ataggggttg gctgacatgg gaggaggaat tttgggggaa    150323145
tggactttag tgtcagataa cggaaggaag agagaatgaa gtcccctttt    150323195
tgatgttgaa atttttttttt tttttttgag acagtttcac tcttgttgca    150323245
caggctggag tgcaatggcg cgatctcggc tcaccgcaac ccccgcctcc    150323295    (SEQ ID NO: 6)
catgttcaag cgattctcct gtctcagcct cctgagtatc tgggattaca    150323345
ggcaccccgcc actacacccg actgattttt ggtatttta gtagagacgg    150323395
ggtttcgcca tgttggccag gctggtctcg aactcgtgac ctcaggtgat    150323445
ccaccccgcct cggcctccca gagtgctggg attacaagcg tgagccaccg    150323495
cacccggcct gaagtcttta taattatggt tttgtttaaa acaatgtttg    150323545
tttgtttgtt tgtttgtttt tgagacggag tctcgctcag tcacccaggc    150323595
tggagtgcag tggtgcgatc tcggctcgcg tcaagctctg cctcccaggt    150323645
tcacgccatt ctgctgcctc agcctcccga gtagctggga ctacaggcgc    150323695
ctgccactac gcctggctaa tttttttttgt atttttagta gagacggggt    150323745
ttcacggtgc tagccaggat ggtttccatc tcctgacctc gtgatctgcc    150323795
cgtcttggcc tcccaaagtg ctgggattac aggcgtgagc cactgcaccc    150323845
ggccaacata atgttcttaa tatataagaag gtactcatat cttttagtga    150323895
atactttatt cattaccacc caaaatatta ctttttaatt gcctgactag    150323945
ttaaataaat acatcataaa aattaggatg ctttgttttt ttttttttgta    150323995
ctttggtaaa ttttgcaata aaatggaaac tgttttttttt ctcttgatag    150324045
```

```
GCGCCCTTGG GATGTCCAAT AGGGACAGCT ATTTTTACGC TGCTATTGTT    150324095    Exon x3
GCAGTGGTCG CCGTCCATGT GGTGCTGGCC CTCTTTGTGT ATGTGGCCTG    150324145    (SEQ ID NO: 4)
GAATGAAGGc TCACGACAGT GGCGTGAAGG CAAACAGGAT TAA
```

```
AGTG AACATCACCT TTTTATAGCA
TTAAATTCAT TTTTTAAAAT GATAAATGCT GGAGGGGGCC ATCTGATTTG    150324262
AATAAAGTtG AAAGAACATG TTAAAGTCAG TCTTAAGGAG TCACGTTTGA    150324312
GTATGTAAAT TTTGATCTTT CTAATATGTT GGTTTGTATA TTCAGTTTTA    150324362
ACTGTATGAA TCTGATTTGC AAATGAGAAT TTGGAAAAGT TAGTTACAAA    150324412
GAAATATGTT AATTTAATTA GACAAATACTC TGGAAGGAAT TTTATCTTCT    150324462
TTCAACAAAA CATGTTTTAT AGTATTCTGA CTTACGGTTG CTTTTGAGTT    150324512
TTACTCATTT GGATATATTA AGATGCACAC AGTGAAGCAA ATTAAACTCC    150324562
ACTTTACGCT GGAATGCTTT CTTTAGCATG AAAATACCAG GTCCTTGGAT    150324612
```

FIG.3A-4

```
TTGGGATTTT AATTTCCTAT GGAAAGTTGC TTAAATTGTG GACACTGGAA   150324662
TTAATCTGAA TGTCACTGAG GAATTTCACA TGAAGTGTAA TCCCTAGTCA   150324712
ATAAGAATTA TCCATTACAT TATTTTATGG GAAAACTAGG CTAAATTACA   150324762
TCCATTCAGG TAAAAGGACC TTAGCTTACT GAAGGATCTA AAGAGCAAAG   150324812
CAAAGATCTC ACTACTCAAA CACTCAGCCT GCTTCCTTCa AGtCCCCTTG   150324862
CAGGCCAGCT TTGTGCTTTG CAGACCAACT TTTTAATGAG ATACTTTGCT   150324912
TCCTCATTCA ACATTGAAGC TAGGCTTCAA TTAAAAGGTT CGAGGAAGCT   150324962
CCATTTAAAA TTGTTTTTTT TACTATTTTT TAAAATTGTA GTGTATATGA   150325012
TAGGAATTTG CATTTAAATA TGTTCATTTT TGCATATGTT AGGAGTGGAA   150325062
ACAATCTGGA AAACATTTTT TTTTCATCCA AAAAGTATTC TCCTTGGGCA   150325112
TATCTGATGG AAAAAAACCT TGATTTTATT TTCGTATCTT TAGTCTGTGT   150325162
TCTTTCTAGT TATTTGGTAC TAATTATGTG CAATCTAAAA ACACTCCCAC   150325212
AAGTATTTGT TTTTTAATTA TAAAATCATA GTAtATGTTC TTTGTAGAAA   150325262
ACTGGAAAAA TACATATTCA AACAGGAAAA AAAATCAAAA TTCCCCATAA   150325312
TGTTGCCATC TAAAAATAAC CTCTATTTTA GTTGATATCC CGTATTCATT   150325362
TTTGAAAGCC ATTCCTTAAT GCTAGTTTGA TACACACTAA AAGTTTAGCT   150325412
TACAAGTTCA AATTCTGCCA GCTTTTCCTG ACAGCTATTT GCATTTTTTT   150325462
CAGATGAGTG ATTATTGGCC ATTTTCTTTT TCTTTTTCTT TATTTTATTT   150325512
ATTTATTTTT TTGAGACAGA GTTTTGCTCT GTTGCCCAGG CTGGAGTGCA   150325562
GTGGTGCAAT CTCGGCTCAC TGCAACCTCT GCCTCCTGGG TTCAAGTGAT   150325612
TCTCCACCTC AGCCTCCCAA GTAGCTGGGA CTACGGATGC CTGCCACCAC   150325662
GCCTGGCTAA TTTTTTTTTG TATTTTTTTG TAGAGACGGG GTTTCACCAT   150325712
GTTGTCCAGG CTAATCTTGA ACTTGTGACC TCAGGTGATC CACCCGCCTC   150325762
GGCCTCCGAA AGTGCTGGGA TTACAGGCGT GAGCTACCAC GCCCGGCCTT   150325812
ATTGACCATT TTCTAAATAA GCACATTCTA TCTTTATTCT CTTAAAATTC   150325862
AAATTTTCTG TTACTGATAA TCCTAATACT AGGATTCTTG CTTAAGTATG   150325912
TGAAACCATT ACCGATTTGT TGTTCACATT TATTTTTTAT GTTGTGAAAC   150325962
TGGACTAAAG GAATAGAGGG ATGATTAGTC ATAAAAGTCA AATAGCATTT   150326012
GTGTTTAACT GTTGAGAAAA GTGAAAGATC AGTaTGATTA TTATGGAACT   150326062
GTTTTTAATT CTTGCTTAAA GACTACAATT TTAGTATAAT GACATTTGAG   150326112
TCTAGGGTAG TATGTGGTAG ATTTCTAGAT GGTCCCTAAT TAAGAAGTAT   150326162
TGTTGTATTT AGAATTGTCC ACCTAATTTC TTTTTATATA ATGCCAAGGT   150326212
ATTTCTTGTG CTTTTGGGAT CTTATGCTGT TTGTAAAATG TTACTGTCCA   150326262
ATGTTGGATT ATTGTTTTGG TTTCAGGCAT TTGCTGAATA GGTGATGATA   150326312
CATGGGTATT TTTCTGCAAG TATTTAAACC AGGGGCATAT GCAAAGGCAG   150326362
TTGTAATTTC CTCTTGGAAA AAGCGCCAAA TGTTTGAAGG TTAAAATCAA   150326412
ATGCTAGGGT TGATATTTAG GCTTATAACA AAATAGGCTT GTTTTCAAAG   150326462
CAGTTTTTTC CTAGAGTTTT AACTGTTAAC TCACTAGTTT GCTGCTGTTT   150326512
TTAACTATGT TAAATAACAT ATGGTATTTG GCAAATAGAT TTATTTTTCA   150326562
AAATGTCTCA CTAGTTTCCT TTTACACAAT GTATATACTT CAAGATGTAT   150326612
AGAAAGGAAA GCTACAGtTG AGCCCTTATA CATGTTTTAA GGTAGAAATA   150326662
TGTTCCCTAT TGTTTGAAAA CTGATTGTAA GAATAACCTC AGTTAGGAGA   150326712
TATAACTTGA AGTGTCAGTC CAAACTACTG ATTTAACCCT ATTTACGGTA   150326762
ACACATTACC TTCCTCACCT CCTGTTTGGC CCTGGAGAAT GTAGTCCTTT   150326812
TTCTCATTTG TGTTGAGAAA TGAAAGTCT GCTGTAGAAT GTATCTGATG    150326862
TCATTAGTTC TTCAAATGGA TACCATTGTA CATATAACAG TAGAATTTGG   150326912
TTTGGGGTTG TTAGTGAAAA AAAATTTAAA CCTGCCATTA AAAATCCCCA   150326962
TGTTTCATGG AAATCTAACA GAAATACATT GTAATAATTA GAACATTTTG   150327012
```

FIG.3A-5

```
TTTTCTTTTT TCTTTTTTTT TTTTTCGAGA CGGAGTTTTG CCCTTCTTGC  150327062
CCAGGCTGGA GTGCAAGGGC GCAATCTCGG CTCGCTGCAA CCTCCGCCTC  150327112
CCGGGTTCAA GCAGTTCTCC TGCCTCAGCC CCCTGAGTAC CTCAGATGAC  150327162
AGGTGCGTGC CACCACACCC GGCTAATTTT TGTATTTTTA GTAGAGACGG  150327212
GGTTTCACCA TGTTAGCCAG GCTAGTCTCG AACTCCTGAC CTCAGGTGAT  150327262
CCACCCGCCT CCGCCTCCCA AAGTGCTGGG ATTACAGGTA TCAGCCACCG  150327312
TGCCTGGCCT AATAATTGGA ACATTTTCAT CATGAAAATG TCATCAGCTT  150327362
TGCCAAAAGA AACAACCAAT TGACTTGTTT GGCGTTTGTT TTCCATTTTC  150327412
ATGTCAATTT TATGTATACA GTTAGAATAC CCAAGGAGAC CACTAAAATC  150327462
AGTTAAACAA GTAGGGTATA TACAAAGAAA GaTGAAACCC GAAAGTACAT  150327512
AAAAAGGATT TAAATCCGAT TTTAGATGTA CCTAGTGTGT ATTTCTTATC  150327562
TCTAGACAAG TTCATGTTTA TTGTTTAATT TATGCCCAAG TGAAGTTGTA  150327612
AACTTATGGT TCAACTCTGA CACAGAATTT GTCACTTGTC TGAGGTCAGT  150327662
GGCAGGTTTC TCTGCTGTCA AGCACTCTGT GTCACCCACC AGATTAGTAT  150327712
AACTATTAAT TCAGACTGTA CTCCTATGTT TAAGATAATT TTTACAAGAG  150327762
CTGGCTGAAG CAGCACATTA GTAACCTGAC AAGATTTCTT TTTCCCTTTT  150327812
CAGGGGGAAA GGGTCACCTT AAAAATAAAT TATTTTCAGG GACTTTGGGA  150327862
ATCTAATGAT AAATATTACA CATAATCTAT GAATAGCTTA ATCCTTTATA  150327912
TATTCCTTAA AATAGGAATT CCTCGACATC ACTCCTGGCC ACACTTTCCT  150327962
TGCCTGTGTT GTTGCTATGT GTATTTGAAA GTAATATCTG CATTCCTTTT  150328012
AAGATGTTCT GTAAGTCATA TTTGTCAGTT ATACAGAGTA GTCTTCCTTT  150328062
TCCCCACGTT CAGTGTAATC TCACTGAACA GTAATAATAG CAATAGCTAA  150328112
CAACATCTGC ACAGCACCTT ACAGTTTGCA AGAACGTTC ACACATTCTC  150328162
ATTTGAGTTT TGCATAGTGA ACCTGTTACG AGATGTCTCT TGACGTCGAT  150328212
GCTAAAAGTG TTAGAATCTT TACATCACTA GAGTCATTGA ATATGCTGTA  150328262
GTATTGAATA GTGCCCTGAC TAGGGGGAGG ATTTGGATGT GCTGCATTTC  150328312
AAGCCGTGTA TAATCATCAA AATGGGGGGC TTGAGTTCtT TAGCTACTTG  150328362
AATCCGATTT ACTTCTGTTA AGTGATGCTT TTCTAACCGT TTTCTGGATG  150328412
GATTTTGTAT TCACTATATT GTAGCTTGTA ATTTGTATAA ATGTACCATC  150328462
TGATGTCATT AAAAAAAGTG TTTGTAGTGC T     (FULL LENGTH SEQUENCE
                                        DISCLOSED AS SEQ ID NO: 1)
```

FIG.3A-6

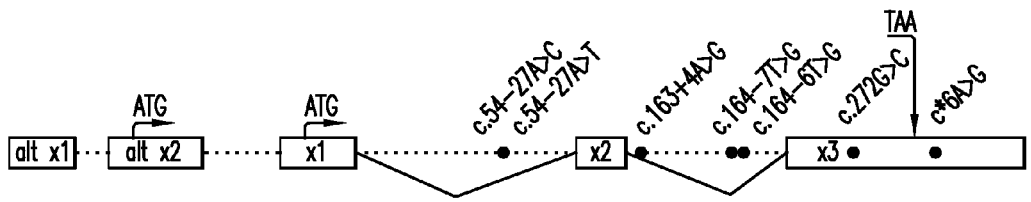

```
TCCCTCGCGG AGCTTACTGA GCGCGGCCGC CGAGCCCAGC TCCGCCGCCG    50
AGCGCCTGTG CCGGCACGGC TACACC

ATGG AGCGCCCGGA TAAGGCGGCG                                100
CTGAACGCAC TGCAGCCTCC TGAGTTCAGA AATGAAAGCT CATTAGCATC    150
TACACTGAAG ACGCTCCTGT TCTTCACAGC TTTAATGATC ACTGTTCCTA    200
TTGGGTTATA TTTCACAACT AAATCTTACA TATTTGAAGG CGCCCTTGGG    250
ATGTCCAATA GGGACAGCTA TTTTTACGCT GCTATTGTTG CAGTGGTCGC    300
CGTCCATGTG GTGCTGGCCC TCTTTGTGTA TGTGGCCTGG AATGAAGGCT    350
CACGACAGTG GCGTGAAGGC AAACAGGAT TAA

AGTGAACA TCACCTTTTT                                       400
ATAGCATTAA ATTCATTTTT TAAAATGATA AATGCTGGAG GGGGCCATCT    450
GATTTGAATA AAGTcGAAAG AACATGTTAA AGTCAGTCTT AAGGAGTCAC    500
GTTTGAGTAT GTAAATTTTG ATCTTTCTAA TATGTTGGTT TGTATATTCA    550
GTTTTAACTG TATGAATCTG ATTTGCAAAT GAGAATTTGG AAAAGTTAGT    600
TACAAAGAAA TATGTTAATT TAATTAGACA ATACTCTGGA AGGAATTTTA    650
TCTTCTTTCA ACAAAACATG TTTTATAGTA TTCTGACTTA CGGTTGCTTT    700
TGAGTTTTAC TCATTTGGAT ATATTAAGAT GCACACAGTG AAGCAAATTA    750
AACTCCACTT TACGCTGGAA TGCTTTCTTT AGCATGAAAA TACCAGGTCC    800
TTGGATTTGG GATTTTAATT TCCTATGAA AGTTGCTTAA ATTGTGGACA    850
CTGAATTAA TCTGAATGTC ACTGAGGAAT TTCACATGAA GTGTAATCCC    900
TAGTCAATAA GAATTATCCA TTACATTATT TTATGGGAAA ACTAGGCTAA    950
ATTACATCCA TTCAGGTAAA AGGACCTTAG CTTACTGAAG GATCTAAAGA    1000
GCAAAGCAAA GATCTCACTA CTCAAACACT CAGCCTGCTT CCTTCgAGcC    1050
CCCTTGCAGG CCAGCTTTGT GCTTTGCAGA CCAACTTTTT AATGAGATAC    1100
TTTGCTTCCT CATTCAACAT TGAAGCTAGG CTTCAATTAA AAGGTTCGAG    1150
GAAGCTCCAT TTAAAATTGT TTTTTTTACT ATTTTTTAAA ATTGTAGTGT    1200
ATATGATAGG AATTTGCATT TAAATATGTT CATTTTTGCA TATGTTAGGA    1250
GTGGAAACAA TCTGGAAAAC ATTTTTTTTT CATCCAAAAA GTATTCTCCT    1300
TGGGCATATC TGATGGAAAA AAACCTTGAT TTTATTTTCG TATCTTTAGT    1350
CTGTGTTCTT TCTAGTTATT TGGTACTAAT TATGTGCAAT CTAAAACAC    1400
TCCCACAAGT ATTTGTTTTT TAATTATAAA ATCATAGTAc ATGTTCTTTG    1450
TAGAAAACTG GAAAAATACA TATTCAAACA GGAAAAAAAA TCAAAATTCC    1500
CCATAATGTT GCCATCTAAA AATAACCTCT ATTTTAGTTG ATATCCCGTA    1550
TTCATTTTTG AAAGCCATTC CTTAATGCTA GTTTGATACA CACTAAAAGT    1600
TTAGCTTACA AGTTCAAATT CTGCCAGCTT TTCCTGACAG CTATTTGCAT    1650
TTTTTTCAGA TGAGTGATTA TTGGCCATTT TCTTTTTCTT TTTCTTTATT    1700
TTATTTATTT ATTTTTTTGA GACAGAGTTT TGCTCTGTTG CCCAGGCTGG    1750
AGTGCAGTGG TGCAATCTCG GCTCACTGCA ACCTCTGCCT CCTGGGTTCA    1800
AGTGATTCTC CACCTCAGCC TCCCAAGTAG CTGGGACTAC GGATGCCTGC    1850
CACCACGCCT GGCTAATTTT TTTTTGTATT TTTTTGTAGA GACGGGGTTT    1900
CACCATGTTG TCCAGGCTAA TCTTGAACTT GTGACCTCAG GTGATCCACC    1950
CGCCTCGGCC TCCGAAAGTG CTGGGATTAC AGGCGTGAGC TACCACGCCC    2000
```

FIG.4A-1

```
GGCCTTATTG ACCATTTTCT AAATAAGCAC ATTCTATCTT TATTCTCTTA 2050
AAATTCAAAT TTTCTGTTAC TGATAATCCT AATACTAGGA TTCTTGCTTA 2100
AGTATGTGAA ACCATTACCG ATTTGTTGTT CACATTTATT TTTTATGTTG 2150
TGAAACTGGA CTAAAGGAAT AGAGGGATGA TTAGTCATAA AAGTCAAATA 2200
GCATTTGTGT TTAACTGTTG AGAAAAGTGA AAGATCAGTg TGATTATTAT 2250
GGAACTGTTT TTAATTCTTG CTTAAAGACT ACAATTTTAG TATAATGACA 2300
TTTGAGTCTA GGGTAGTATG TGGTAGATTT CTAGATGGTC CCTAATTAAG 2350
AAGTATTGTT GTATTTAGAA TTGTCCACCT AATTTCTTTT TATATAATGC 2400
CAAGGTATTT CTTGTGCTTT TGGGATCTTA TGCTGTTTGT AAAATGTTAC 2450
TGTCCAATGT TGGATTATTG TTTTGGTTTC AGGCATTTGC TGAATAGGTG 2500
ATGATACATG GGTATTTTTC TGCAAGTATT TAAACCAGGG GCATATGCAA 2550
AGGCAGTTGT AATTTCCTCT TGGAAAAAGC GCCAAATGTT TGAAGGTTAA 2600
AATCAAATGC TAGGGTTGAT ATTTAGGCTT ATAACAAAAT AGGCTTGTTT 2650
TCAAAGCAGT TTTTTCCTAG AGTTTTAACT GTTAACTCAC TAGTTTGCTG 2700
CTGTTTTTAA CTATGTTAAA TAACATATGG TATTTGGCAA ATAGATTTAT 2750
TTTTCAAAAT GTCTCACTAG TTTCCTTTTA CACAATGTAT ATACTTCAAG 2800
ATGTATAGAA AGGAAAGCTA CAGcTGAGCC CTTATACATG TTTTAAGGTA 2850
GAAATATGTT CCCTATTGTT TGAAAACTGA TTGTAAGAAT AACCTCAGTT 2900
AGGAGATATA ACTTGAAGTG TCAGTCCAAA CTACTGATTT AACCCTATTT 2950
ACGGTAACAC ATTACCTTCC TCACCTCCTG TTTGGCCCTG GAGAATGTAG 3000
TCCTTTTTCT CATTTGTGTT GAGAAATGAA AAGTCTGCTG TAGAATGTAT 3050
CTGATGTCAT TAGTTCTTCA AATGGATACC ATTGTACATA TAACAGTAGA 3100
ATTTGGTTTG GGGTTGTTAG TGAAAAAAAA TTTAAACCTG CCATTAAAAA 3150
TCCCCATGTT TCATGGAAAT CTAACAGAAA TACATTGTAA TAATTAGAAC 3200
ATTTTGTTTT CTTTTTTCTT TTTTTTTTTT TCGAGACGGA GTTTTGCCCT 3250
TCTTGCCCAG GCTGGAGTGC AAGGGCGCAA TCTCGGCTCG CTGCAACCTC 3300
CGCCTCCCGG GTTCAAGCAG TTCTCCTGCC TCAGCCCCCT GAGTACCTCA 3350
GATGACAGGT GCGTGCCACC ACACCCGGCT AATTTTTGTA TTTTTAGTAG 3400
AGACGGGGTT TCACCATGTT AGCCAGGCTA GTCTCGAACT CCTGACCTCA 3450
GGTGATCCAC CCGCCTCCGC CTCCCAAAGT GCTGGGATTA CAGGTATCAG 3500
CCACCGTGCC TGGCCTAATA ATTGGAACAT TTTCATCATG AAAATGTCAT 3550
CAGCTTTGCC AAAAGAAACA ACCAATTGAC TTGTTTGGCG TTTGTTTTCC 3600
ATTTTCATGT CAATTTTATG TATACAGTTA GAATACCCAA GGAGACCACT 3650
AAAATCAGTT AAACAAGTAG GGTATATACA AAGAAAGgTG AAACCCGAAA 3700
GTACATAAAA AGGATTTAAA TCCGATTTTA GATGTACCTA GTGTGTATTT 3750
CTTATCTCTA GACAAGTTCA TGTTTATTGT TTAATTTATG CCCAAGTGAA 3800
GTTGTAAACT TATGGTTCAA CTCTGACACA GAATTTGTCA CTTGTCTGAG 3850
GTCAGTGGCA GGTTTCTCTG CTGTCAAGCA CTCTGTGTCA CCCACCAGAT 3900
TAGTATAACT ATTAATTCAG ACTGTACTCC TATGTTTAAG ATAATTTTTA 3950
CAAGAGCTGG CTGAAGCAGC ACATTAGTAA CCTGACAAGA TTTCTTTTTC 4000
CCTTTTCAGG GGGAAAGGGT CACCTTAAAA ATAAATTATT TTCAGGGACT 4050
TTGGGAATCT AATGATAAAT ATTACACATA ATCTATGAAT AGCTTAATCC 4100
TTTATATATT CCTTAAAATA GGAATTCCTC GACATCACTC CTGGCCACAC 4150
TTTCCTTGCC TGTGTTGTTG CTATGTGTAT TTGAAAGTAA TATCTGCATT 4200
CCTTTTAAGA TGTTCTGTAA GTCATATTTG TCAGTTATAC AGAGTAGTCT 4250
TCCTTTTCCC CACGTTCAGT GTAATCTCAC TGAACAGTAA TAATAGCAAT 4300
AGCTAACAAC ATCTGCACAG CACCTTACAG TTTGCAAAGA ACGTTCACAC 4350
ATTCTCATTT GAGTTTTGCA TAGTGAACCT GTTACGAGAT GTCTCTTGAC 4400
GTCGATGCTA AAAGTGTTAG AATCTTTACA TCACTAGAGT CATTGAATAT 4450
GCTGTAGTAT TGAATAGTGC CCTGACTAGG GGGAGGATTT GGATGTGCTG 4500
CATTTCAAGC CGTGTATAAT CATCAAAATG GGGGCTTGA GTTCcTTAGC 4550
TACTTGAATC CGATTTACTT CTGTTAAGTG ATGCTTTTCT AACCGTTTTC 4600
TGGATGGATT TTGTATTCAC TATATTGTAG CTTGTAATTT GTATAAATGT 4650
ACCATCTGAT GTCATTAAAA AAAGTGTTTG TAGTGCT (SEQ ID NO: 7)
```

FIG.4A-2

MERPDKAALN ALQPPEFRNE SSLASTLKTL LFFTALMITV PIGLYFTTKS YIFEGALGMS    60    (SEQ ID NO: 11)
NRDSYFYAAI VAVVAVHVVL ALFVYVAWNE GSRQWREGKQ D                      101

FIG.4B

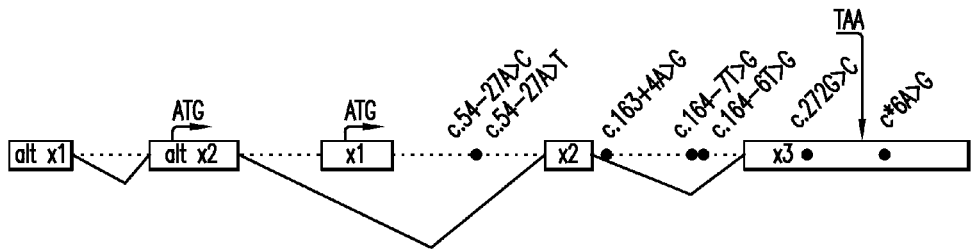

GGGTCACTGG CATCGAGTCT GGAACAGTCA TTCTCAGCAA GAGCTCTTTG    50
AACTCTGACA TTCTCTAGTT TTACGGACTC GGCACCACAG CCCTCTGGCT    100
GGTAGTCCCT CTTCGCGGCT CAT*ATG*¹CTCG GGTCTCCTTG CGGCCCCCAG    150
CTCAGCGACC GAGACGCAGA CGAGGACCAG TGTTCACGCG AGTTCAGGGG    200
GCGGCGTAGC CGCCGCCCGC CCAGGAGGAC C*ATG*²TTGCGC GGCAAGTCCC    250
GGCTCAACGT GGAGTGGCTG GGCTACTCGC CAGGCCTGCT CCTCGAGCAC    300
AGCCCCCTCC TGGCAGGGCG CACGCCGCGG AGCCACCGCC GAAATGAAAG    350
CTCATTAGCA TCTACACTGA AGACGCTCCT GTTCTTCACA GCTTTAATGA    400    (SEQ ID NO: 10)
TCACTGTTCC TATTGGGTTA TATTTCACAA CTAAATCTTA CATATTTGAA    450
GGCGCCCTTG GGATGTCCAA TAGGGACAGC TATTTTTACG CTGCTATTGT    500
TGCAGTGGTC GCCGTCCATG TGGTGCTGGC CCTCTTTGTG TATGTGGCCT    550
GGAATGAAGG CTCACGACAG TGGCGTGAAG GCAAACAGGA TT*AA*AGTGAA    600
CATCACCTTT TTATAGCATT AAATTCATTT TTTAAAATGA TAAATGCTGG    650
AGCGGGCCAT CTGATTTGAA TAAAGTTGAA AGAACATGTT AAA...?

FIG.4C

MLGSPCGPQL SDRDADEDQC SREFRGRRSR RPPRRTMLRG KSRLNVEWLG YSPGLLLEHR    60
PLLAGRTPRS HRRNESSLAS TLKTLLFFTA LMITVPIGLY FTTKSYIFEG ALGMSNRDSY   120    (SEQ ID NO: 12)
FYAAIVAVVA VHVVLALFVY VAWNEGSRQW REGKQD                            156

FIG.4D

MLRGKSRLNV EWLGYSPGLL LEHRPLLAGR TPRSHRRNES SLASTLKTLL FFTALMITVP    60
IGLYFTTKSY IFEGALGMSN RDSYFYAAIV AVVAVHVVLA LFVYVAWNEG SRQWREGKQD   120    (SEQ ID NO: 13)

FIG.4E

| Family, ethnicity and number of affected patients per family | | | Mutation type | Relevance, predicted outcome | Controls* | |
|---|---|---|---|---|---|---|
| | | | | | T | E |
| XMEA-1 | American | 3 | c.54-27A>T | The mutated A nucleotide is the predicted splicing branch point**. The mutation would inhibit nucleophilic attack of the branch point onto the 5' splice site of the first intron during splicing. | 360 | 133 |
| XMEA-2 | Italian | 1 | c.54-27A>T | | 360 | 108 |
| XMEA-3 | French | 1 | c.54-27A>C | | 360 | 119 |
| XMEA-4 | French | 2 | c.163+4A>G | The fourth position after an exon is A in 70% of all exons. This mutation is expected to result in suboptimal binding of the U1 snRNA to the 5' splice site. | 360 | 119 |
| XMEA-5 | French | 2 | c.163+4A>G | | 360 | 119 |
| XMEA-6 | French | 2 | c.163+4A>G | | 360 | 119 |
| XMEA-7 | French | 4 | c.164-7T>G | This mutation introduces a purine into the polypyrimidine tract of this splice site. This is predicted to decrease the binding strength of the U2AF splice factor. | 465 | 122 |
| XMEA-8 | French | 2 | c.164-7T>G | | 465 | 122 |
| XMEA-9 | French | 5 | c.164-7T>G | | 465 | 122 |
| XMEA-10 | Finnish | 5 | c.272G>C | This coding mutation is predicted to disrupt a binding motif for the SC35 splice factor***. It also changes a Glycine to Alanine. | 304 | 84 |
| XMEA-11 | Finnish | 2 | c.272G>C | | 304 | 84 |
| XMEA-12 | Armenian | 7 | c.*6A>G | 3' UTR mutation in proximity to the stop codon. This mutation may disrupt binding of transcript stabilization and processing factors. | 304 | 92 |
| XMEA-13 | American | 10 | c.*6A>G | | 304 | 128 |
| XMEA-14 | American | 3 | c.*6A>G | | 304 | 128 |

FIG.5

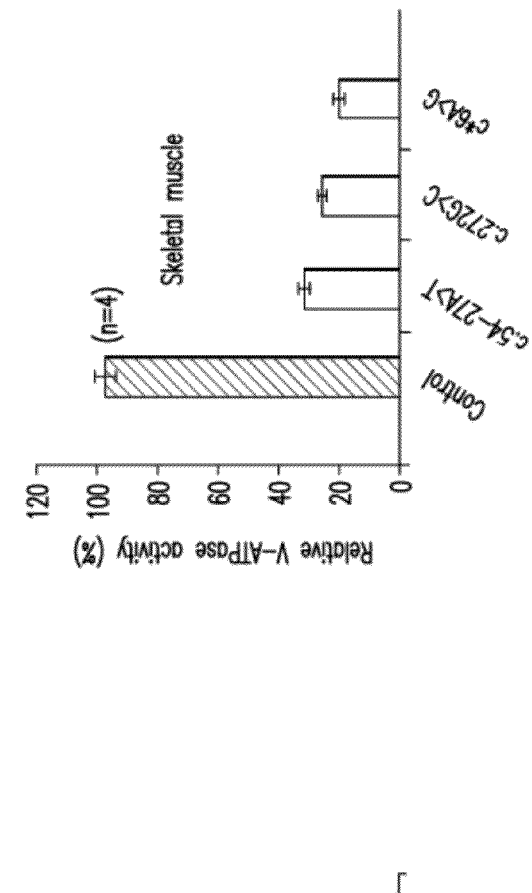
FIG. 6G
FIG. 6F
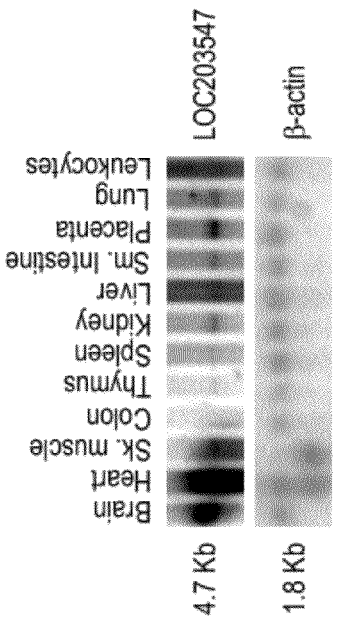
FIG. 7

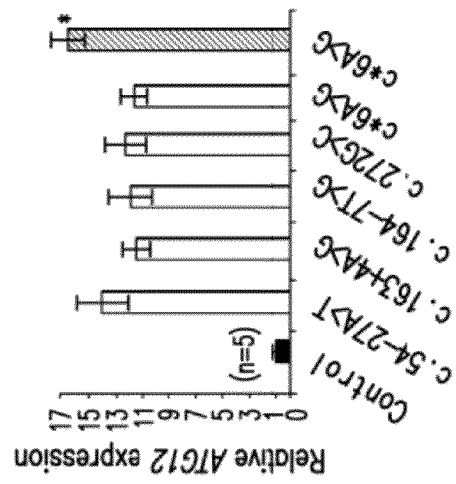
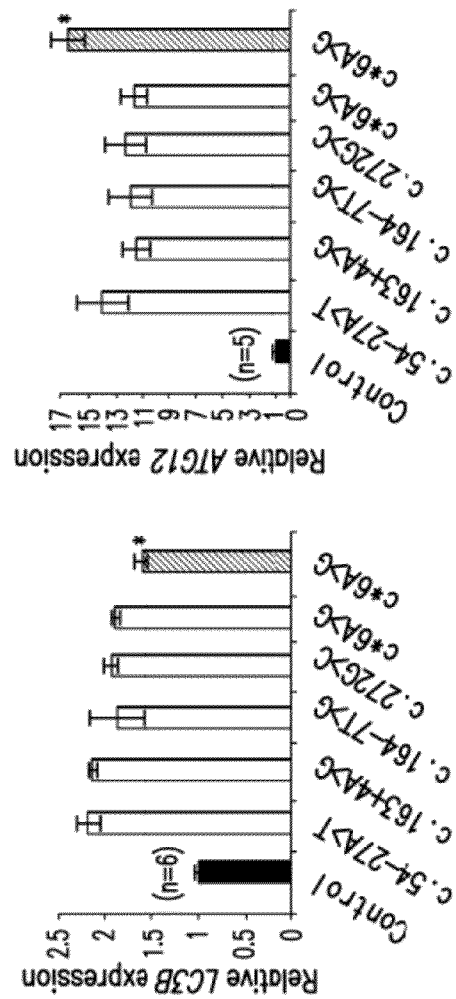
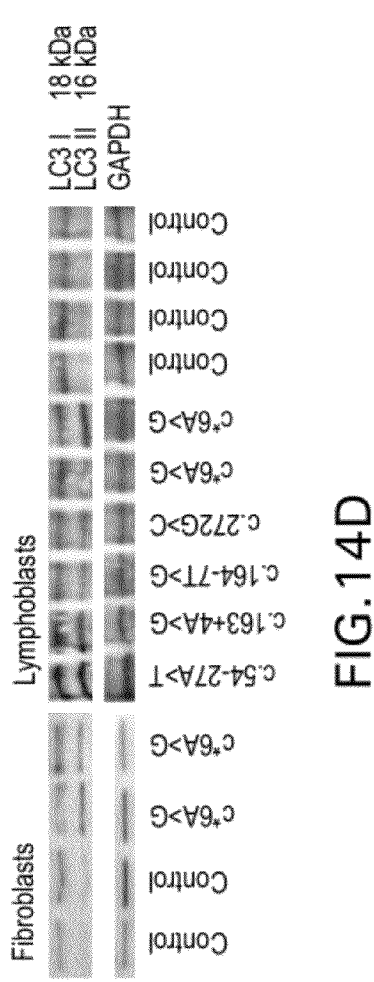
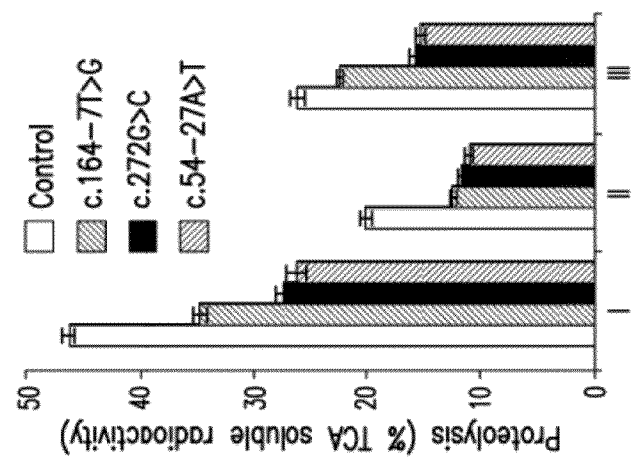

| SEQ ID NO: | Primer name | Primer sequence | Used for |
|---|---|---|---|
| 14 | LOC203547-x1-F | GAGTGGCTGGGCTACTCG | Mutation screening |
| 15 | LOC203547-x1-R | GACACAGCGAGAGAAAGTGCT | |
| 16 | LOC203547-x2-F | TCCTCCTGCATAGCATCTCA | |
| 17 | LOC203547-x2-R | GGAAAACTGTCAAGCTGAAACA | |
| 18 | LOC203547-x3-F | ACTTTATTCATTACCACCCAAAAT | |
| 19 | LOC203547-x3-R | CAAACCAACATATTAGAAAGATCAAAA | |
| 20 | LOC203547-RT-F | GATAAGGCGGCGCTGAAC | RT-PCR |
| 21 | LOC203547-RT-R | CCCCCTCCAGCATTTATCAT | |
| 22 | Q-LOC203547-F | CCTGAGTTCAGAAATGAAAGCTCA | q-PCR |
| 23 | Q-LOC203547-R | TCCCAAGGGCGCCTTCAAATATGT | |
| 24 | Q-BACT-F | CTGGAACGGTGAAGGTGACA | |
| 25 | Q-BACT-R | AAGGGACTTCCTGTAACAATGCA | |
| 26 | LC3B-F | AGCAGCTTCCTGTTCTGGAT | |
| 27 | LC3B-R | CTGGGAGGCATAGACCATGT | |
| 28 | ATG12-F | GTCTTCCGCTGCAGTTTCC | |
| 29 | ATG12-R | ATGAGTCCTTGGATGGTTCG | |
| 30 | FI-HindIII-F | TATAAGCTTGCTACACCATGGAGCGCCCGGAT | minigene construct |
| 31 | FI-XbaI-SalI-R | TATTCTAGAGTCGACCACTGACCTATTCCCCATGA | |
| 32 | FII-SalI-F | TATGTCGACCACTGAGTTTCTTCACTTAGT | |
| 33 | FII-XbaI-BglII-R | TATTCTAGAAGATCTTCCGTTATCTGACACTAAAGTC | |
| 34 | FIII-BglII-F | TATAGATCTAGGCGTGAGCCACTGCAC | |
| 35 | FIII-XbaI-R | TATTCTAGAACTGTCGTGAGCCTTCATTC | |
| 38 | LOC203547-North-F | TTGTAAACTTATGGTTCAACTCTGA | Northern blotting |
| 39 | LOC203547-North-R | TCAAGAGACATCTCGTAACAGG | |
| 36 | KpnI-VMA21-F | TATGGTACCATGGAGCGCCCGGATAAG | Myc-tagged construct |
| 37 | XbaI-VMA21-R | TATTCTAGAATCCTGTTTGCCTTCACG | |

COMPOSITIONS AND METHODS FOR DIAGNOSIS OF AUTOPHAGIC VACUOLAR MYOPATHY

CROSS-REFERENCE TO RELATED APPLICATIONS

This application claims the benefit of priority to U.S. Provisional Application 61/059,317 filed Jun. 6, 2008, which is hereby incorporated by reference in its entirety.

SEQUENCE LISTING

The instant application contains a Sequence Listing which has been submitted in ASCII format via EFS-Web and is hereby incorporated by reference in its entirety. Said ASCII copy, created on Feb. 24, 2012, is named 07620703.txt and is 52,218 bytes in size.

FIELD OF THE INVENTION

The present invention relates to compositions and methods and particularly to the identification of mutations relating to the diagnosis of autophagic vacuolar myopathy.

BACKGROUND

Autophagic vacuoles are a frequent feature in numerous neuromuscular disorders and myopathies. Among these, Dannon disease is the most known. However, there are other vacuolar myopathies or autophagic vacuolar myopathies, including, for example, X-linked myopathy with excessive autophagy (XMEA), infantile autophagic vacuolar myopathy, adult-onset autophagic vacuolar myopathy with multiorgan involvement, and X-linked congenital autophagic vacuolar myopathy. See, e.g., Nishino, I., "Autophagic vacuolar myopathy," *Semin Pediatr Neurol* 13:90-95 (2006), the entire contents and disclosure of which is hereby incorporated by reference. Currently, patients suffering from muscular dystrophy, including limb-girdle muscular dystrophy, are often tested by taking an invasive muscular biopsy from affected patients followed by pathological study to diagnose or rule out particular types of disease. Furthermore, existing methods may leave an exact diagnosis uncertain due to similar characteristics and symptoms displayed by various vacuolar myopathies. A need exists in the art for improved compositions and methods for diagnosing and distinguishing among various types of limb-girdle muscular dystrophy and/or vacuolar or vacuolated myopathies that do not require such invasive procedures and that are capable of giving more accurate and definite results.

SUMMARY

According to a first broad aspect of the present invention, a method is provided comprising the following steps: (a) taking a sample from an individual; and (b) determining whether the individual has one or more of the following mutations in the VMA21 gene or locus: c.54−27A>T; c.54−27A>C; c.163+4A>G; c.164−7T>G; c.164−6T>G; c.272G>C; or c.*6A>G. According to this first broad aspect, the method may further comprise step (c) of diagnosing the individual as having or at risk of developing a vacuolar or vacuolated myopathy disease if the individual has one or more of the mutations in the VMA21 gene or locus.

According to a second broad aspect of the present invention, a method is provided comprising the following steps: (a) taking a sample from an individual; and (b) determining whether the sample has a reduced level or enzymatic activity of a V-ATPase complex compared to a control level or activity of the V-ATPase complex in a normal or wild-type individual. According to this second broad aspect, the method may further comprise step (c) of diagnosing the individual as having or at risk of developing a vacuolar or vacuolated myopathy disease if the sample has a reduced level or activity of the V-ATPase complex compared to the control level or activity of the V-ATPase complex.

According to a third broad aspect of the present invention, a DNA molecule of at least 15 nucleotides in length is provided comprising a polynucleotide sequence that is 90% identical to a portion of the genomic sequence for the human VMA21 gene or locus (SEQ ID NO: 1) and having one or more of the following mutations: c.54−27A>T; c.54−27A>C; c.163+4A>G; c.164−7T>G; c.164−6T>G; c.272G>C; or c.*6A>G. According to this third broad aspect, the DNA molecule may be double stranded and may be cloned or inserted into a vector, and the DNA molecule may be contained in a host cell.

According to a fourth broad aspect of the present invention, a population of cultured cells taken from the body of an individual having a form of vacuolar or vacuolated myopathy is provided, wherein the population of cultured cells contains one or more of the following mutations in the VMA21 gene or locus: c.54−27A>T; c.54−27A>C; c.163+4A>G; c.164−7T>G; c.164−6T>G; c.272G>C; or c.*6A>G. Alternatively, a population of cultured cells taken from the body of an individual having a form of vacuolar or vacuolated myopathy is provided, wherein the population of cultured cells has a reduced level or activity of a V-ATPase complex compared to a control level or activity of the V-ATPase complex in a normal or wild-type individual.

BRIEF DESCRIPTION OF DRAWINGS

FIGS. 3A-1 through 3A-6 is the genomic sequence for the human VMA21 gene (SEQ ID NO: 1) on the X chromosome (from the UCSC Genome Browser on Human March 2006 Assembly) showing various features of the VMA21 gene, including demarcation of exons ("Exon x1," "Exon x2" and "Exon x3" disclosed as SEQ ID NOS 2-4, respectively) and introns (positions 150316492-150322760 disclosed as SEQ ID NO: 5 and positions 150322871-150324045 disclosed as SEQ ID NO: 6), with (i) upper case letters=exons; (ii) upper case italics=5' and 3' untranslated region (UTR); (iii) lower case letters=introns; (iv) underlined letters=splice sites; (v) bold oversized letters=locations of mutations found in human XMEA or other vacuolar or vacuolated myopathy; (vi) bold double-underlined letters=start and stop codons for translation; and (vii) lower case italics letters in UTR=uncertain nucleotides due to discrepancies between sequences. FIG. 3A-1 discloses the "Alt x1" and "Alt x2" sequences as SEQ ID NOS 8 and 9, respectively;

FIGS. 4A-1 and 4A-2 is a schematic illustration showing the splice sites of the main transcript of VMA21 in relation to the genomic locus (joining exons x1, x2, and x3) and the polynucleotide sequence of the cDNA sequence (NM_001017980) corresponding to the main transcript of VMA21 (SEQ ID NO: 7), with (i) upper case italics=5' and 3' untranslated region (UTR); (ii) underlined letters=splice sites; (iii) bold oversized letters=locations of mutations found in human XMEA or other vacuolar or vacuolated myopathy (present in mature transcript); (iv) bold double-underlined letters=start and stop codons for translation; and (v) lower case italics letters in UTR=uncertain nucleotides due to discrepancies between sequences;

FIG. 4B is the polypeptide sequence of VMA21 protein (SEQ ID NO: 11) translated from the main transcript of VMA21 with the bold oversized letter=the location of an amino acid mutation found in human XMEA or other vacuolar or vacuolated myopathy;

FIG. 4C is a schematic illustration showing the splice sites of the alternative transcript of VMA21 in relation to the genomic locus (joining exons alt x1, alt x2, x2, and x3) and the polynucleotide sequence of the cDNA sequence (ENST00000370361) corresponding to the alternative transcript of VMA21 (SEQ ID NO: 10), with (i) upper case italics=5' and 3' untranslated region (UTR); (ii) underlined letters=splice sites; (iii) bold oversized letters=locations of mutations found in human XMEA or other vacuolar or vacuolated myopathy (present in mature transcript); and (iv) bold double-underlined letters=start and stop codons for translation with ATG' and ATG² representing two possible in-frame start codons;

FIG. 4D is the polypeptide sequence of VMA21 protein (SEQ ID NO: 12) translated from the alternative transcript of VMA21 using the first start codon (ATG') with the bold oversized letter=the location of an amino acid mutation found in human XMEA or other vacuolar or vacuolated myopathy;

FIG. 4E is the polypeptide sequence of VMA21 protein (SEQ ID NO: 13) translated from the alternative transcript of VMA21 using the second start codon (ATG²) with the bold oversized letter=the location of an amino acid mutation found in human XMEA or other vacuolar or vacuolated myopathy;

FIG. 5 is a table providing an overview of the LOC203547 mutations identified in 14 unrelated XMEA families with (*) indicating that the numbers of chromosomes are from normal individuals genotyped for each mutation (T=total number of chromosomes, and E=number of chromosomes from ethnically matched individuals), () indicating a prediction by Splicing Sequences Finder of Branch Point Sequence; and (*) indicating a prediction by Exonic Splicing Enhancer Finder;

FIG. 6F is a bar graph showing relative V-ATPase activity in lymphoblast light membrane fraction of patients having the indicated mutations relative to controls (Each bar represents the mean±standard deviation of three independent experiments);

FIG. 6G is a bar graph showing relative V-ATPase activity in skeletal muscle light membrane fraction of patients having the indicated mutations relative to controls (Each bar represents the mean±standard deviation of three independent experiments);

FIG. 7 is a Northern blot of RNA samples from multiple human tissues (Clontech) hybridized with a 598 bp fragment of the coding region of VMA21 identifying a single transcript present in each tissue;

FIG. 8 discloses SEQ ID NOS 41, 42, 41 and 43-45, respectively, in order of appearance.

FIG. 14C is a bar graph showing the macroautophagic portion of total lysosome-dependent proteolysis from different groups of cells having the indicated mutations relative to control with group I being the 36 hour time points from FIG. 14B, group II being cells cultured with the specific macroautophagy inhibitor 3-MA, and group III being the difference between I and II (i.e., between total lysosome-dependent proteolysis and its non-macro autophagic portion);

FIG. 14D is a set of Western blots for LC3 including LC3-I (an 18 kDa protein) which is processed to a LC3-II isoform (a 16 kDa protein) upon induction of autophagy in fibroblasts or lymphocytes having the indicated mutations relative to a control with GAPDH used as a loading control;

FIG. 14E is a bar graph showing the relative expression by quantitative RT-PCR of the LC3B (ATG8) gene in patients with the indicated mutations relative to control with expression levels of the β-actin gene used as control and error bars representing means±standard deviation from three independent experiments performed in triplicate;

FIG. 14F is a bar graph showing the relative expression of the ATG12 gene by quantitative RT-PCR in patients with the indicated mutations relative to control with expression levels of the β-actin gene used as control and error bars representing means±standard deviation from three independent experiments performed in triplicate;

FIG. 18 is a table showing a list of primers (SEQ ID NOS 14-35, 38-39 and 36-37, respectively, in order of appearance) used in the present study.

DETAILED DESCRIPTION

Definitions

Where the definition of terms departs from the commonly used meaning of the term, applicant intends to utilize the definitions provided below, unless specifically indicated.

For purposes of the present invention, the term "main transcript" refers to the predominant mRNA transcript expressed from a gene.

For purposes of the present invention, the terms "alternative transcript" or "alternative transcripts" refer to one or more mRNA transcripts that are expressed from a gene in a minor proportion relative to the main transcript.

For purposes of the present invention, the term "exon" refers to the portion of a gene that is present in the mature mRNA transcript expressed form the gene (i.e., not excised during RNA processing).

For purposes of the present invention, the term "intron" refers to the portion of a gene that is present in the pre-mRNA transcript but removed from the mature mRNA transcript expressed form the gene (i.e., excised during RNA processing).

For purposes of the present invention, the terms "5' untranslated region" or "5'UTR" refer to the portion of the mature mRNA transcript of a gene upstream from the start ATG codon that is not translated into the protein encoded by the gene.

For purposes of the present invention, the terms "3' untranslated region" or "3' UTR" refer to the portion of the mature mRNA transcript of a gene downstream from the stop or termination codon that is not translated into the protein encoded by the gene.

For purposes of the present invention, the term "splice site" refers to a nucleotide position within an exon of a gene typically located at the 5' or 3' end of an exon that joins with a splice site of a different exon in the mature mRNA transcript following processing of the message.

For purposes of the present invention, the term "individual" refers to a human individual that may be tested, diagnosed, etc., for the presence of one or more of the herein identified mutations in the VMA21 gene and/or the level and/or activity of the V-ATPase complex according to embodiments of the present invention. The term "individual" may also refer to a human individual having or at risk of developing a form of vacuolar or vacuolated myopathy.

Figure 1A:
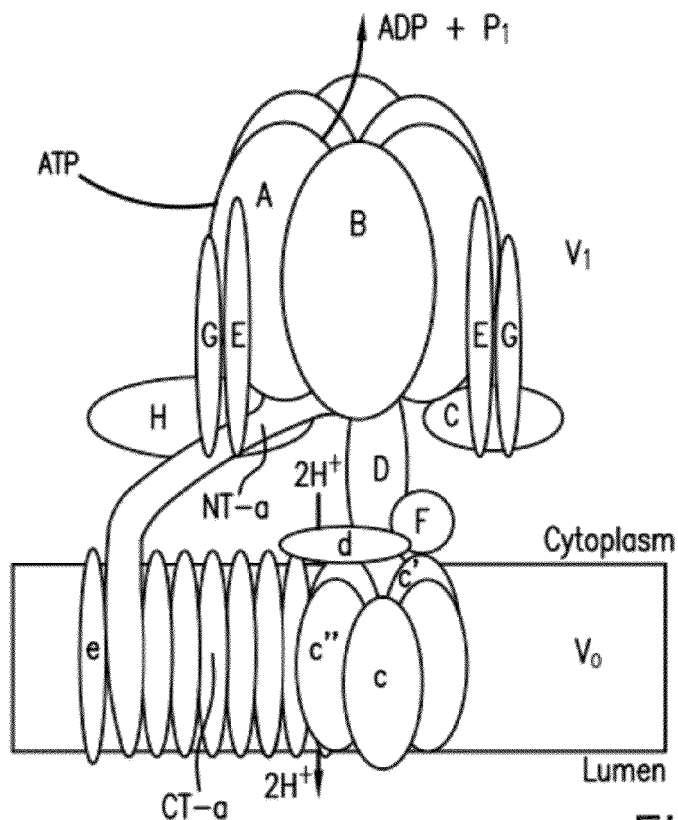
FIG. 1A is a schematic illustration of the V-ATPase proton pump showing the subunit organization of the V-ATPase with $V_0$=membrane-integral sector or portion and $V_1$=cytoplasmic sector or portion.
Figure 1B:
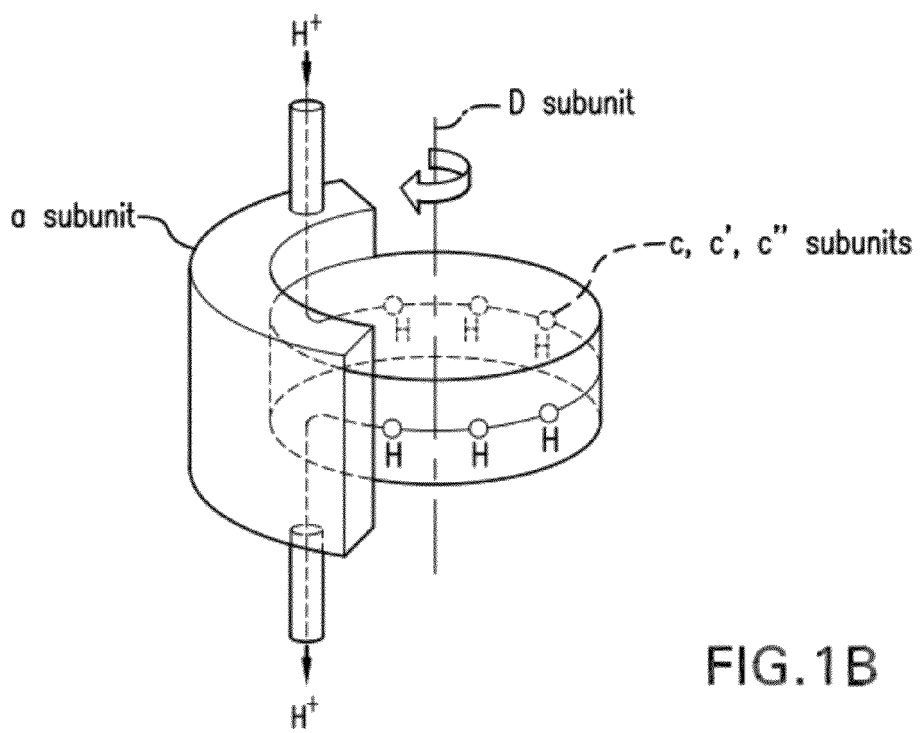
FIG. 1B is a model illustration of the rotary pumping mechanism of the V-ATPase with the force of rotation generated by ATPase activity of $V_1$ subunits A and B.
Figure 1C:
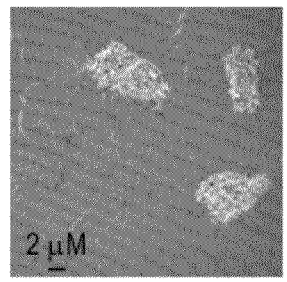
FIG. 1C is an image of a cross-section of XMEA muscle showing intra-sarcoplasmic vacuoles.
Figure 1D:
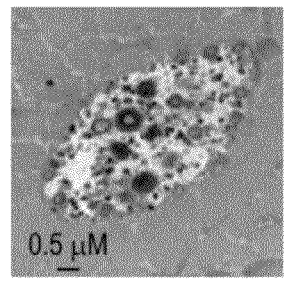
FIG. 1D is a closer image of a cross-section of XMEA muscle showing non-specific degradation content within a typical XMEA autophagic vacuole.
Figure 1E:
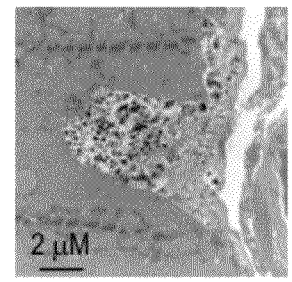
FIG. 1E is a closer image of a cross-section of XMEA muscle showing a vacuole merging with the sarcolemma.
Figure 1F:
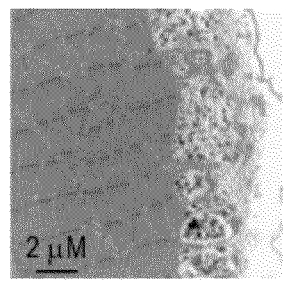
FIG. 1F is a closer image of a cross-section of XMEA muscle showing multiple vacuoles merging with the sarcolemma and extruding contents to the extracellular space.
Figure 1G:
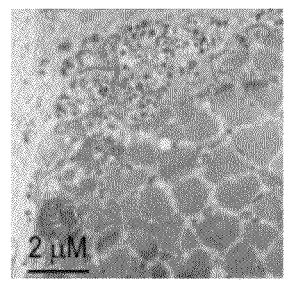
FIG. 1G is a closer image of a cross-section of XMEA muscle showing multi-fold duplication of basal lamina with released vacuolar contents present between the multiple layers.
Figure 1H:
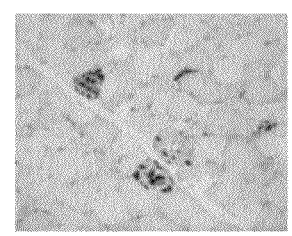
FIG. 1H is an image generated by light microscopy of a cross-section of XMEA muscle immunostained for LAMP2 with most, but not all, vacuoles being LAMP2-positive and with LAMP2 signal strong in the lumen of these vacuoles.
Figure 2A:
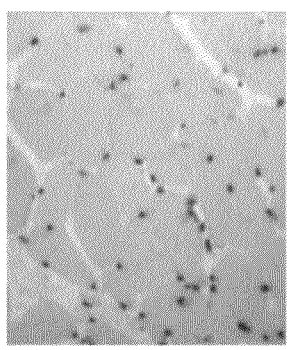
FIG. 2A is an image (picture width 250 μm) of a cross-section of skeletal muscle from a normal individual showing no TUNEL staining.
Figure 2B:
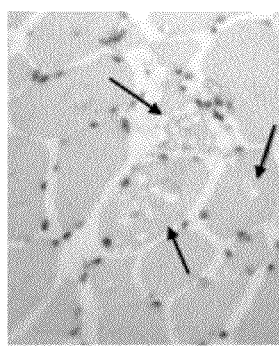
FIG. 2B is an image (picture width 250 μm) of a cross-section of skeletal muscle from an XMEA patient showing numerous vacuoles in the sarcoplasm of some of the myofibers (indicated by arrows) but no TUNEL staining.
Figure 2C:
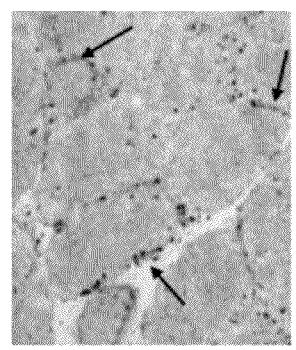
FIG. 2C is an image (picture width 0.5 nm) of a cross-section of the thymus of an infant used as a positive control showing the expected intense TUNEL staining at the periphery of the lobules.

For purposes of the present invention, the terms "identity" or "identical" for a polynucleotide sequences refer to the degree (often expressed in terms of percentage) to which two or more polynucleotide sequences have the same nucleotides or bases in the same order. For example, a polynucleotide sequence having at least 90% identity (that is 90% identical) to a reference sequence will have at least 90% of its nucleotides or bases the same or identical along the length of the polynucleotide sequence in the same order. The terms "identity" or "identical" may also refer to the degree (often expressed in terms of percentage) to which two or more polypeptide sequences have the same amino acids in the same order Description V-ATPases are ubiquitous in endomembrane systems of all cells. In humans and other species, V-ATPases are also expressed at the plasma membrane of specialized cells that secrete acid. V-ATPases acidify lysosomes and regulate the pH of multiple systems in the cell, including the secretory pathway and the endovesicular system, which use gradated pH to accomplish stepwise modifications. The V-ATPase is composed of 13 subunits organized into a transmembrane ($V_0$) and a cytoplasmic ($V_1$) sector (FIG. 1A), and has a unique pumping mechanism. Note that the $V_0$ subunits are conventionally referred to with lowercase, and the $V_1$ subunits are conventionally referred to with uppercase letters. The 'a' subunit of the $V_0$ sector spans the membrane and forms two separate channels within it that are not continuous with each other. One channel starts in the cytoplasm and ends within the membrane lipid bilayer, and the other starts from a different location in the lipid bilayer and opens in the organelle lumen. Protons enter from the cytoplasm into the first channel and exit within the bilayer. There, they load onto the side of a cylinder (composed of $V_0$ subunits c, c', c'' and d) which rotates and transports them to the entrance of the second 'a' channel, through which they exit into the organelle. The torque that rotates this cylinder is provided by the $V_1$ complex, which generates the force by consuming ATP (FIGS. 1A and 1B). See, e.g. Forgac, M., "Vacuolar ATPases: rotary proton pumps in physiology and pathophysiology," Nat Rev Mol Cell Biol 8:917-929 (2007).

Biogenesis of the V-ATPase is of major interest. In yeast, assembly of the $V_0$ sector takes place in the endoplasmic reticulum (ER), and a chief chaperone coordinating the process is the yeast Vma21p protein. See, e.g., Malkus, P. et al., "Role of Vma21p in assembly and transport of the yeast vacuolar ATPase," Mol Biol Cell 15:5075-5091 (2004), the entire contents and disclosure of which is hereby incorporated by reference. V-ATPase subunits are conserved from yeast to man, but the closest known mammalian sequence to yeast Vma21p has less than 18% identity and lacks a dilysine signal important in yeast Vma21p function (see, e.g., Malkus, P. et al. (2004), supra), thus making it unclear whether this predicted protein (i.e., LOC203547) is indeed the mammalian orthologue of Vma21p and/or whether V-ATPase biogenesis in mammals parallels that of yeast.

V-ATPase function appears vital. To date, all disease-causing mutations in V-ATPase subunits are in specialized isoforms conferring specialized functions to the V-ATPase, such as localization and action at the plasma membranes of acid secreting cells. See, e.g. Frattini, A. et al., "Defects in TCIRG1 subunit of the vacuolar proton pump are responsible for a subset of human autosomal recessive osteopetrosis," Nat Genet. 25:343-346 (2000); Karet, F. E. et al., "Mutations in the gene encoding BI subunit of H+-ATPase cause renal tubular acidosis with sensorineural deafness," Nat Genet. 21:84-90 (1999); Kornak, U. et al., "Impaired glycosylation and cutis laxa caused by mutations in the vesicular H+-ATPase subunit ATP6V0A2," Nat Genet. 40:32-34 (2008); and Smith, A. N. et al., "Mutations in ATP6N1B, encoding a new kidney vacuolar proton pump 116-kD subunit, cause recessive distal renal tubular acidosis with preserved hearing," Nat Genet. 26:71-75 (2000), the entire contents and disclosures of which are hereby incorporated by reference. There are no human diseases known with mutations in any of the subunits common to all V-ATPases.

X-linked myopathy with excessive autophagy (XMEA; OMIM 310440) is a skeletal muscle disorder inherited in recessive fashion affecting boys and sparing carrier females. See, e.g., Kalimo, H. et al., "X-linked myopathy with excessive autophagy: a new hereditary muscle disease," Ann Neurol 23:258-265 (1988), the entire contents and disclosure of which is hereby incorporated by reference. Onset is in childhood with weakness of the proximal muscles of the lower extremities, progressing gradually but slowly to involve other muscle groups and towards loss of independent ambulation after age 50. Other organs including the heart and brain are clinically unaffected. Pathological analysis of skeletal muscle biopsies shows no inflammation, necrosis or apoptosis as analyzed by TUNEL staining (FIG. 2) and electron microscopy. Instead, myofiber demise appears to occur through a novel form of autophagic cell death. Giant autophagic vacuoles of about 2 to 10 μm in size (i.e., about 100 times the size of normal lysosomes) are seen encircling sections of cytoplasm including organelles, proteins, glycogen, calcium-containing compartments and membrane whorls. The vacuoles contain lysosomal hydrolases, yet appear unable to complete digestion of their contents. Instead, they migrate to the myofiber surface, fuse with the sarcolemma, and extrude the contents extracellularly, forming a field of cell debris rich in lysosomal enzymes around the fiber (FIG. 1C through 1H and FIG. 2). See, e.g. Chabrol, B. et al., "X-linked myopathy with excessive autophagy: a clinicopathological study of five new families," Neuromuscul Disord 11:376-388 (2001); Kalimo, H. et al. (1988), supra; Minassian, B. A. et al., "X-linked myopathy with excessive autophagy," In: Structural and Molecular Basis of Skeletal Muscle Diseases, G. Karpati, ed. (Zurich, ISN Neuropath Press), pp. 145-147; and Villanova, M. et al., "X-linked vacuolated myopathy: complement membrane attack complex on surface membrane of injured muscle fibers," *Ann Neurol* 37:637-645 (1995), the entire contents and disclosures of which are hereby incorporated by reference.

The disease name 'with excessive autophagy' was given to convey the above highly unusual pathology, and does not refer to the modern molecular pathway of autophagy, of which almost nothing was known at the time. There are at least two other diseases with autophagic vacuolation similar to XMEA: chloroquine myopathy, a side-effect of the anti-malarial and anti-rheumatic agent chloroquine; and Danon disease caused by mutations in the lysosome associated membrane protein 2 (LAMP2) gene. See, e.g., Macdonald, R. D. et al., "Experimental chloroquine myopathy," *J Neuropathol Exp Neurol* 29:479-499 (1970); Stauber, W. T. et al., "Inhibition of lysosomal function in red and white skeletal muscles by chloroquine," *Exp Neurol* 71:295-306 (1981); and Nishino, I. et al., "Primary LAMP-2 deficiency causes X-linked vacuolar cardiomyopathy and myopathy (Danon disease)," *Nature* 406:906-910 (2000), the entire contents and disclosures of which are hereby incorporated by reference.

It is shown herein that LOC203547 is the human orthologue of yeast Vma21p, and hypomorphic mutations in this gene may disrupt autophagy and cause XMEA and/or possibly other vacuolar or vacuolated myopathies. XMEA represents an unusual mechanism of genetic disease: a major housekeeping enzyme (i.e., the V-ATPase) complex essential to multiple cell systems in all tissues is downregulated but only to a level affecting systems with high reliance on this complex (including autophagy) to a clinical extent in only one tissue (i.e., skeletal muscle). As a result, a syndrome is generated corresponding to part of the housekeeping enzyme's functions in a single organ.

The human VMA21 gene (previously referred to as LOC203547) is mapped to the Xq28 region of the X chromosome. The human VMA21 gene is composed of three main exons and two alternative exons that are upstream of the three main exons. FIG. 3 provides a genomic sequence (SEQ ID NO. 1 corresponding to nucleotide positions from 150315696 to 150328493 in FIG. 3) and overview of the human VMA21 gene starting with the first of the two alternative exons and continuing to the last main exon coding including sequence for the 3' untranslated region (UTR) of the mRNA transcript. In FIG. 3, the exons are shown as upper case letters, and the introns are shown in lower case letters. Upper case letters that are italicized represent sequences that may be either a 5' or 3' UTR sequence in at least some transcripts. However, the 5' UTR of the human VMA21 gene may further include the sequence from $ATG^1$ to just before $ATG^2$ in the exon "alt x2" for the alternative transcript if the $ATG^2$ is used as the start codon (see below).

The first main exon (referred to herein as "exon x1" or "x1"; SEQ ID NO: 2) includes nucleotides at positions 150316363 through 150316491 along the length of the X chromosome, which further includes the 5' UTR sequence; the second main exon (referred to herein as "exon x2" or "x2"; SEQ ID NO: 3) includes nucleotides at positions 150322761 through 150322870 along the length of the X chromosome; and the third main exon (referred to herein as "exon x3" or "x3"; SEQ ID NO: 4) includes nucleotides starting at position 150324046 of the X chromosome and continuing downstream, which further includes the 3' UTR sequence. The length of the third exon ("exon x3" or "x3") may vary depending on the exact site of polyadenylation. For example, as shown in FIG. 3, the third exon may terminate at nucleotide position 150328493 of the X chromosome before polyadenylation. These exons are also labeled in the margin of FIG. 3. The first and second main exons are spaced by a first main intron (SEQ ID NO: 5), and the second and third exons are spaced by a second main intron (SEQ ID NO: 6).

For the main VMA21 transcript, FIG. 3 shows the start "ATG" codon present in "exon x1" and the termination "TAA" codon present in "exon x3" in bold and double underlined. FIG. 4A provides a cDNA sequence (SEQ ID NO: 7) for the main mRNA transcript expressed from the VMA21 gene with intronic sequences excised, which may be deduced from the genomic sequence as described in FIG. 3. Nucleotides are numbered from the start of "exon x1" through the spliced exons "x2" and "x3." Pairs of underlined nucleotides refer to the joined splice sites from two different exons as a result of mRNA processing. For example, the GA pair at cDNA positions 129 and 130 numbered from the beginning of the transcript (or positions 53 and 54 numbered from the adenine (A) of the start "ATG" codon) corresponds to the joint splice sites for exons "x1" and "x2," whereas the GG pair at cDNA positions 239 and 240 numbered from the beginning of the transcript (or positions 163 and 164 numbered from the adenine (A) of the start "ATG" codon) corresponds to the joint splice sites for exons "x2" and "x3."

For an alternative VMA21 transcript, the first alternative exon (referred to herein as "alt x1"; SEQ ID NO: 8) includes nucleotides at positions 150315696 through 150315777 along the length of the X chromosome, which further includes the 5' UTR sequence, and the second alternative exon (referred to herein as "alt x2"; SEQ ID NO: 9) includes nucleotides at positions 150315929 through 150316187 along the length of the X chromosome. The third and fourth exons of this alternative VMA21 transcript are the same exons "x2" and "x3" described above for the main transcript. These exons are also labeled in the margin of FIG. 3. The length of exon "x3" in the alternative VMA21 transcript may vary depending on the exact site of polyadenylation. The 3' UTR sequence of alternate transcript may further extend beyond 3'UTR sequence shown in FIG. 4C. For example, 3' UTR of alternate transcript cDNA sequence in FIG. 4C may further comprise all or a portion of 3'UTR sequence shown in FIG. 4A for main transcript.

For an alternative VMA21 transcript, FIG. 3 shows two in-frame start "ATG" codons (i.e., $ATG^1$ and $ATG^2$ shown in bold and underlined in FIGS. 3 and 4C) present in "alt x1" and the termination "TAA" codon present in "exon x3" shown as before in bold and double underlined. FIG. 4C provides at least part of a cDNA sequence (SEQ ID NO: 10) for the alternative mRNA transcript expressed from the VMA21 gene with intronic sequences excised, which may be deduced from the genomic sequence as described in FIG. 3. Nucleotides may be numbered from the start of exon "alt x1" through the spliced "exon x3." Pairs of underlined nucleotides refer to the joined splice sites from two different exons as a result of mRNA processing. For example, the GC pair at cDNA positions 82 and 83 numbered from the beginning of the alternative transcript (or the beginning of exon "alt x1") corresponds to the joint splice sites for exons "alt x1" and "alt x2," the GA pair at cDNA positions 341 and 342 numbered from the beginning of the alternative transcript (or the beginning of exon "alt x1") corresponds to the joint splice sites for exons "alt x2" and "x2," and the GG pair at cDNA positions 451 and 452 numbered from the beginning of the alternative transcript (or the beginning of exon "alt x1") corresponds to the joint splice sites for exons "x2" and "x3."

The polypeptide sequence of the VMA21 protein encoded by the main transcript may have the sequence shown in FIG. 4B (SEQ ID NO: 11). The polypeptide sequence of the VMA21 protein encoded by the alternative transcript may have either the sequence shown in FIG. 4D (SEQ ID NO: 12) or FIG. 4E (SEQ ID NO: 13) depending on whether the first start codon (ATG$^1$) or the second start codon (ATG$^2$), respectively, in exon "alt x2" is used.

The present work further identifies mutations present in the VMA21 gene or locus in that may indicate a predisposition to or a presence of vacuolar or vacuolated myopathy disease. Since the VMA21 gene is located on the X chromosome, mutations in the VMA21 gene will generally affect males more than females. The following mutations are identified in individuals or patients having X-linked myopathy with excessive autophagy (XMEA): c.54–27A>T; c.54–27A>C; c.163+4A>G; c.164–7T>G; c.272G>C; and c.*6A>G. The "c." refers to cDNA. In addition, the following mutation is identified in patients having infantile autophagic vacuolar myopathy or X-linked congenital autophagic vacuolar myopathy: c.164–6T>G. Each of these mutations is shown in FIG. 3 as bold oversized letters. Each of these mutations is also shown where relevant as bold oversized letters in FIG. 4, but since many of these mutations are present in intronic sequences, they are excised with the introns and are therefore not present in the mature mRNA transcripts.

The "c.54–27A>T" mutation is shown in FIG. 3 as the adenine (A) at position 150322734 on the X chromosome present in the intron between exons "x1" and "x2," but close to exon x2. The notation "c.54–27" refers to the position of this mutation, which is 27 nucleotides upstream of the cDNA splice site derived from "exon x2" at nucleotide position 54 of the main transcript or cDNA of the VMA21 gene as shown in FIG. 4A (SEQ ID NO: 7) when numbered from the adenine (A) of the start ATG codon with the nucleotide position of the adenine (A) of the start ATG codon of the main transcript or cDNA designated as the first nucleotide position. Note that this numbering differs from the nucleotide positions shown in FIG. 4A since it is numbered from the ATG start site and not from the beginning of the transcript. The notation "A>T" refers to the mutation or replacement of the adenine (A) at this position with a thymine (T). The "c.54–27A>C" mutation is the same as the "c.54–27A>T" mutation, except that the adenine (A) at this position is mutated with a cytosine (C). Note that these mutations do not appear in the mature VMA21 transcript since they are present in the sequence of an excised intron.

The "c.163+4A>G" mutation is shown in FIG. 3 as the adenine (A) at position 150322874 on the X chromosome present in the intron between exons "x2" and "x3," but close to exon x2. The notation "c.163+4" refers to the position of this mutation, which is 4 nucleotides downstream of the splice site derived from "exon x2" at nucleotide position 163 of the main transcript or cDNA of the VMA21 gene as shown in FIG. 4A (SEQ ID NO: 7) when numbered from the adenine (A) of the start ATG codon with the nucleotide position of the adenine (A) of the start ATG codon of the main transcript or cDNA designated as the first nucleotide position. Note that this numbering differs from the nucleotide positions shown in FIG. 4A since it is numbered from the ATG start site and not from the beginning of the transcript. The notation "A>G" refers to the mutation or replacement of the adenine (A) at this position with a guanine (G). This mutation does not appear in the mature VMA21 transcript since it is present in the sequence of an excised intron.

The "c.164–7T>G" mutation is shown in FIG. 3 as the thymine (T) at position 150324039 on the X chromosome present in the intron between exons "x2" and "x3," but close to exon x3. The notation "c.164-7" refers to the position of this mutation, which is 7 nucleotides upstream of the cDNA splice site derived from "exon x3" at nucleotide position 164 of the main transcript or cDNA of the VMA21 gene as shown in FIG. 4A (SEQ ID NO: 7) when numbered from the adenine (A) of the start ATG codon with the nucleotide position of the adenine (A) of the start ATG codon of the main transcript or cDNA designated as the first nucleotide position. Note that this numbering differs from the nucleotide positions shown in FIG. 4A since it is numbered from the ATG start site and not from the beginning of the transcript. The notation "T>G" refers to the mutation or replacement of the thymine (T) at this position with a guanine (G). This mutation does not appear in the mature VMA21 transcript since it is present in the sequence of an excised intron.

The "c.164–6T>G" mutation is shown in FIG. 3 as the thymine (T) at position 150324040 on the X chromosome present in the intron between exons "x2" and "x3," but close to exon x3. The notation "c.164-6" refers to the position of this mutation, which is 6 nucleotides upstream of the cDNA splice site derived from "exon x3" at nucleotide position 164 of the main transcript or cDNA of the VMA21 gene as shown in FIG. 4A (SEQ ID NO: 7) when numbered from the adenine (A) of the start ATG codon with the nucleotide position of the adenine (A) of the start ATG codon of the main transcript or cDNA designated as the first nucleotide position. Note that this numbering differs from the nucleotide positions shown in FIG. 4A since it is numbered from the ATG start site and not from the beginning of the transcript. The notation "T>G" refers to the mutation or replacement of the thymine (T) at this position with a guanine (G). This mutation does not appear in the mature VMA21 transcript since it is present in the sequence of an excised intron.

The "c.272G>C" mutation is shown in FIG. 3 as the guanine (G) at position 150324154 on the X chromosome present in exon "x3." The notation "c.272" refers to the position of this mutation, which is derived from "exon x3" at nucleotide position 272 of the main transcript or cDNA of the VMA21 gene as shown in FIG. 4A (SEQ ID NO: 7) when numbered from the adenine (A) of the start ATG codon with the nucleotide position of the adenine (A) of the start ATG codon of the main transcript or cDNA designated as the first nucleotide position. Note that this numbering differs from the nucleotide positions shown in FIG. 4A since it is numbered from the ATG start site and not from the beginning of the transcript. The notation "G>C" refers to the mutation or replacement of the guanine (G) at this position with a cytosine (C). Note also that this mutation will appear in the mature VMA21 transcript since it is present in the sequence of "exon x3."

The "c.*6A>G" mutation is shown in FIG. 3 as the adenine (A) at position 150324194 on the X chromosome present in exon "x3." The notation "c.*6" refers to the position of this mutation, which is 6 nucleotides downstream of the TAA termination or stop codon in "exon x3" of the main transcript or cDNA of the VMA21 gene as shown in FIG. 4A (SEQ ID NO: 7) with the adenine (A) immediately following or downstream of the TAA termination or stop codon of the main transcript or cDNA designated as the first nucleotide position. Note that this numbering differs from the nucleotide positions shown in FIG. 4A since it is numbered from the TAA termination or stop codon and not from the beginning of the transcript. The notation "A>G" refers to the mutation or replacement of the adenine (A) at this position with a guanine (G). Note also that this mutation will appear in the mature VMA21 transcript since it is present in the sequence of "exon x3."

According to a broad aspect of the present invention, methods are provided for the detection of one or more of the mutations that are identified herein in or near the VMA21 gene locus on the X chromosome present in a sample. According to some embodiments, methods are provided for the diagnosis or determination of whether an individual has, or is predisposed or at risk to develop, a form of vacuolar or vacuolated myopathy based on the detection or presence of one or more of the herein identified mutations in or near the human VMA21 gene locus. According to embodiments of the present invention, methods of the present invention may comprise determining whether an individual or patient has any one or more of the following presently identified mutations in or near the human VMA21 (LOC203547) gene locus on the X chromosome shown herein to correspond to a disease, such as a form of vacuolar or vacuolated myopathy: c.54−27 A>T; c.54−27 A>C; c.163+4 A>G; c.164−7 T>G; c.164−6T>G; c.272 G>C; and/or c.*6A>G as described herein.

According to some embodiments of the present invention, such methods may also be used to differentiate among various forms of vacuolar or vacuolated myopathy or to rule out a form of vacuolar or vacuolated myopathy based on a negative result(s). For example, one or more mutations in the human VMA21 gene may be used to diagnose an individual or patient as having, experiencing, at risk of developing, or likely to develop X-linked myopathy with excessive autophagy (XMEA) disease. Such mutations corresponding to XMEA may include, for example, c.54−27 A>T; c.54−27 A>C; c.163+4 A>G; c.164−7 T>G; c.272 G>C; and/or c.*6A>G. Alternatively, the c.164−6T>G mutation in the human VMA21 gene may be used to determine or diagnose that an individual or patient has, is experiencing, is at risk of developing, or is likely to develop infantile autophagic vacuolar myopathy or X-linked congenital autophagic vacuolar myopathy. However, it is possible that a mutation or substitution at these nucleotide or base positions of the VMA21 gene may include a mutation or substitution to a different nucleotide or base, which may also indicate the presence or likelihood of developing a form of vacuolar or vacuolated myopathy.

According to embodiments of the present invention, such methods for diagnosing and/or differentiating among various types of vacuolar or vacuolated myopathies may be used in testing (i) any individual or patient having or experiencing limb-girdle muscular dystrophy and/or symptoms of a vacuolar or vacuolated myopathy to determine if such individual or patient is experiencing, for example, XMEA, infantile autophagic vacuolar myopathy, or X-linked congenital autophagic vacuolar myopathy, or (ii) to rule out such diseases even when they are not suspected. Such diagnostic methods of the present invention may be further used to determine (iii) whether an individual that is not yet experiencing symptoms may have a predisposition to develop a form of vacuolar or vacuolated myopathy disease, or (iv) whether an individual, such as a female individual, is a carrier of one or more of the herein identified mutations in the human VMA21 gene, who may contribute or transmit a mutant allele of the VMA21 gene to their offspring.

According to embodiments of the present invention, the detection of one or more of the presently identified mutations in the human VMA21 gene may be achieved by any method for the detection of single point mutations in a genomic DNA or cDNA sequence known in the art. See, e.g., U.S. Pat. No. 5,545,527, issued Aug. 13, 1996, the relevant contents and disclosures of which are hereby incorporated by reference. According to some embodiments, a DNA or RNA preparation may be generated from a sample or biopsy taken from an individual or patient for testing. Such a DNA or RNA preparation may then be used to determine if it contains one or more of the presently identified mutations in the human VMA21 gene. According to some embodiments, a DNA preparation may be pre-selected or enriched to preferentially include sequences corresponding to a region of the human X chromosome including all or a portion of the VMA21 gene from an individual, and DNA fragments in such a DNA preparation may be cloned into a vector. RNA preparations may be pre-selected or enriched to include, for example, only the polyadenylated mRNA fraction.

According to embodiments of the present invention, to detect the presence of one or more of the herein identified mutations in the human VMA21 gene in a DNA preparation, which may be pre-selected or enriched to contain a sequence of interest, such as a sequence including all or a portion of the human VMA21 gene, from a sample or biopsy taken from an individual, any technique known in the art may be used. The following merely provides some basic examples and concepts of methods for the detection of one or more point mutations known in the art.

According to some embodiments, the DNA preparation, which may be pre-selected or enriched to contain a sequence of interest, may be subjected to restriction digest followed by a restriction fragment length polymorphism (RFLP) technique to detect a mutation based on an altered pattern of restriction fragments caused by the alteration, abolishment, or creation of a restriction site due to the mutation. Such restriction enzyme-based techniques may be combined with the use of a hybridization probe to detect one or more particular bands of interest (e.g., Southern blot), which may allow detection with less pre-selection or enrichment of the DNA preparation, and the hybridization probe may be designed to preferentially bind to either the wild-type or mutant sequence to provide greater specificity.

According to some embodiments, an allele-specific primer(s) or oligonucleotide(s) may be designed to preferentially or exclusively hybridize to either a wild-type sequence or a sequence containing one or more of the herein identified mutations in the human VMA21 gene under a particular set of conditions that may be optimized for stringency based on salt concentration, temperature, etc., to only or preferentially allow hybridization with either the wild-type or mutant DNA sequence having greater complementarity. Alternatively, such an allele-specific primer(s) or oligonucleotide(s) may be designed to selectively prime DNA synthesis of either a wild-type sequence or a sequence containing one or more of the herein identified mutations in the human VMA21 gene under a particular set of stringency conditions. For example, such an allele-specific primer(s) or oligonucleotide may provide a basis for detection of one or more of the mutations using PCR, such that a PCR product will be formed only if the allele-specific primer has greater complementarity with a sequence of interest present in the DNA preparation. Such allele-specific primer(s) may also provide a basis for detection of one or more of the mutations using PCR by generating a PCR product in greater amounts or with faster kinetics over time if the allele-specific primer(s) has greater complementarity with a sequence of interest present in the DNA preparation.

According to some embodiments, an allele-specific probe(s) may be used as a labeled and detectable hybridization probe to provide a basis for detection of one or more of the herein identified mutations, which may either be used for detection according to any known technique including, for example, in situ staining, affinity chromatography, probing of a blot (e.g., Southern blot), fluorescence arrays, etc. For RNA preparations, allele-specific primer(s) or probe(s) may be similarly used to form a basis for detection by Northern blot, RT-PCR, etc., but these techniques will generally only apply to those mutations that are remain in the mature mRNA transcript (i.e., not excised or spliced out with the intron sequences during RNA processing), such as the c.272G>C or c.*6A>G mutations. The manner of detection for hybridization probes may utilize any known method including the use of radioisotopes, modified nucleotides, etc.

The exact set of stringency conditions as well as the identity of the allele-specific primer(s), oligonucleotide(s), or probe(s) used may be designed or chosen based on a number of known rules and guidelines known in the art including, for example, approximating their melting temperature ($T_m$), their predicted ability to prime DNA synthesis, etc., in relation to a sequence of interest, which may be confirmed through experimentation. The exact sequence or identity of the allele-specific primer(s), oligonucleotide(s), or probe(s) may depend, for example, on whether it is used as an allele-specific hybridization probe for direct detection or an allele-specific primer for PCR. For example, a mismatch in the center of a hybridization probe may be more likely to reduce affinity and melting temperature, but a mismatch at the 3'-end of a primer may be less likely to prime DNA synthesis in a PCR reaction. Allele-specific primer(s) or oligonucleotide(s) may have a minimum length between about 15 and 18 nucleotides to achieve sufficient affinity and specificity.

Other methods may also be used to detect one or more of the mutations. For example, differences in the structure of DNA or RNA/DNA hybrids caused by the existence of a mismatch between a probe and DNA sequence of interest may provide a basis for detection of one or more mutations by exploiting such differences in structure, which may be reflected, for example, by their electrophoretic mobility in a non-denaturing gel. Alternatively, for example, a mutation-specific or mutation-exclusive antibody may be generated to only recognize and bind with high affinity to a polypeptide sequence containing either the wild-type or mutant sequence VMA21 sequence. Such antibodies would only be relevant for detecting mutations that result in an amino acid change in the encoded VMA21 protein, such as the c.272 G>C mutation.

According to some embodiments, methods for determining whether an individual or patient has one or more of the herein identified mutations in the human VMA21 gene may preferably be achieved by sequencing of a DNA fragment of interest from a cDNA or genomic sequence containing all or a portion of the human VMA21 gene. Such a DNA fragment of interest obtained from a sample or biopsy taken from an individual or patient may be isolated or purified for sequencing according to any known method. For example, a DNA fragment of interest may be amplified by directed PCR using a set of primers designed to specifically target and amplify the DNA fragment of interest, such as a DNA fragment containing all or a portion of the human VMA21 gene. Generally speaking, such primers will generally be chosen to flank one or more of the sites of the herein identified mutations, such that the DNA fragment of interest amplified or generated includes one or more of these sites for sequencing to determine the presence or absence of the herein identified mutation(s). For example, an isolated or amplified DNA fragment of interest may be cloned into a vector or plasmid to facilitate sequencing. Once the cloned DNA fragment of interest obtained from a sample or biopsy taken from an individual or patient has been sequenced, it may be determined whether the individual or patient has one or more of the herein identified mutations in the human VMA21 gene. Furthermore, sequence analysis of the DNA fragment of interest to determine the presence or absence of one or more of the herein identified mutations in the VMA21 gene according to methods of the present invention may either be performed alone or in combination with sequence analysis of other known genes or loci, which may collectively form part of a panel of genes or sequences to be tested together.

Any blood or tissue sample from an individual or patient may theoretically be used as a source making a DNA or RNA preparation to be tested, and such blood or tissue sample may be frozen or stored prior to testing. In addition, amniotic fluid may be used to determine if a developing fetus is at risk of developing disease associated with one or more of the mutations in the VMA21 gene, although it may be separately determined if the mother is a carrier by assaying a blood or tissue sample taken from the mother. Although one aim of the present invention is to avoid invasive biopsies as a tissue source, diagnostic methods of the present invention may be performed using biopsies derived from different tissues including muscle tissue.

According to another broad aspect of the present invention, methods are provided for determining the level and/or enzymatic activity of the V-ATPase complex in a sample taken from an individual or patient according to any known and/or herein described method. For example, hydrolysis of ATP by V-ATPase may be measured by the bafilomycin A1 sensitive assay method as described further below to determine the activity of the V-ATPase complex. To determine the levels of the V-ATPase complex, the level of $V_0$ or $V_1$ subunits of the V-ATPase complex may be measured according to any known technique, such as by Western blot, immunostaining of tissue, etc. Such assays may be performed, for example, using a protein extract or tissue homogenate or fraction derived from the sample. According to embodiments of the present invention, such methods may be used as a basis to determine if an individual or patient has or is predisposed to develop any form of vacuolar or vacuolated myopathy if such an individual or patient has a reduced level and/or activity of the V-ATPase complex relative to a normal or wild-type control. In addition to XMEA, infantile autophagic vacuolar myopathy, or X-linked congenital autophagic vacuolar myopathy, such diagnostic methods based on V-ATPase activity may be used to identify and diagnose vacuolar myopathies where the causative gene is unknown and/or located on a chromosome other than the X chromosome. For example, such diagnostic methods may be used to identify or diagnose a vacuolar myopathy linked to chromosome 19. See, e.g., Di Blasi, C. et al., "Abnormal Lysosomal and Ubiquitin-Proteasome Pathways in 19p13.3 Distal Myopathy," 56(1):133-8 (2004); and Servidei, S. et al., "A distinctive autosomal dominant vacuolar neuromyopathy linked to 19p13," 53(4):830-7 (1999), the entire contents and disclosures of which are hereby incorporated by reference.

According to some embodiments, methods for determining the level and/or enzymatic activity of the V-ATPase complex in an individual or patient may also be used to differentiate among different types or forms of vacuolar or vacuolated myopathies, which may be associated differing levels and/or activities of the V-ATPase complex. Since the V-ATPase assay is not based necessarily on any specific mutation, such an approach may provide a broader and perhaps more sensitive technique for detecting and/or diagnosing a type or form of vacuolar or vacuolated myopathy or to distinguish between different types or forms of vacuolar or vacuolated myopathies. Blood and tissue sources or samples for assaying the level and/or activity of the V-ATPase complex may theoretically be the same as described above and may be frozen or stored prior to testing. For example, lymphoblasts, fibroblasts, and/or skeletal muscle cells or tissue may be used as a tissue source. Diagnostic methods based on the level and/or activity of the V-ATPase may be performed either alone or in combination with other tests, including, for example, sequence analysis of the VMA21 gene or other known genes or loci.

According to embodiments of the present invention, an individual or patient to be tested for the presence one or more of the herein identified mutations in the human VMA21 gene and/or assayed for the level and/or activity of the V-ATPase complex may include any person or individual having an interest in determining whether they have or are predisposed to develop a vacuolar or vacuolated myopathy, or are a carrier for one or more of the VMA21 mutations that may be transmitted to their offspring. An individual or patient may also be tested for the presence one or more of the herein identified mutations in the human VMA21 gene and/or assayed for the level and/or activity of the V-ATPase complex to rule out vacuolar or vacuolated myopathy (even when it is not suspected) or to possibly distinguish among different types or forms of vacuolar or vacuolated myopathies. According to some embodiments, an individual or patient to be tested for the presence one or more of the herein identified mutations in the human VMA21 gene and/or assayed for the level and/or activity of the V-ATPase complex may include any person or individual experiencing limb-girdle muscular dystrophy and/or any perceived symptoms that may be characterisitic symptoms of a vacuolar or vacuolated myopathy (i) to determine if such an individual or patient has a vacuolar or vacuolated myopathy, (ii) to possibly distinguish among different types or forms of a vacuolar or vacuolated myopathy, or (iii) to rule out such diseases.

According to another broad aspect of the present invention, a double or single stranded DNA molecule(s) is provided having a polynucleotide sequence comprising at least a portion of a genomic or cDNA sequence for a mutant human VMA21 gene or locus containing one or more of the herein identified mutations. In the case of a double stranded DNA molecule(s), a DNA molecule having a polynucleotide sequence comprising at least a portion of a genomic or cDNA sequence for a mutant human VMA21 gene or locus containing one or more of the herein identified mutations is provided in combination with a complementary DNA molecule strand. According to some embodiments, such DNA molecules may be used for expression of a mutant human VMA21 gene or locus containing the herein identified mutations in a cell. Alternatively, such DNA molecules may be used as a probe or primer with various detection or PCR-based amplification techniques according to method embodiments of the present invention. For example, a DNA molecule comprising at least a portion of the human VMA21 gene or locus and containing one or more of the herein identified mutations may be introduced into a cell and expressed to study V-ATPase function, the role of VMA21 in disease, or any other relevant question. For example, such a DNA molecule may be introduced into a cell transgenically such as by transfection, through homologous recombination with the endogenous locus, or by any other known method.

According to some embodiments, such a DNA molecule(s) having a polynucleotide sequence comprising at least a portion of the human VMA21 gene or locus and containing one or more of the herein identified mutations may be used as a primer or probe, such as an allele specific primer or probe, for detection according to methods of the present invention. Minimum lengths for primers used in a PCR reaction are generally between about 15 to 18 nucleotides in length, but often have a greater length. Since there may be numerous polymorphisms that are often benign (especially in non-coding sequences) between different individuals, it may necessary for there to be less than 100% identity in the polynucleotide sequence of DNA molecules of the present invention and/or mixtures of DNA molecules of the present invention having differing sequences may be used together to accommodate for this variation. Therefore, according to some embodiments, a DNA primer is provided comprising a polynucleotide sequence that is at least 15 or 18 nucleotides in length and at least 90% identical to at least a portion of the human VMA21 gene or locus and having one or more of the herein identified mutations in the human VMA21 gene. However, the length of a DNA molecule (such as a primer or probe) may be much longer (e.g., even hundreds or thousands of nucleotides or bases in length).

According to some embodiments, a DNA molecule having a polynucleotide sequence comprising at least a portion of the human VMA21 gene or locus and containing one or more of the herein identified mutations may be cloned or inserted into any known type of vector, such as plasmids, artificial chromosomes, viruses, etc., for their maintenance, use, and/or expression. For example, such a vector may be used to synthesize or express RNA or protein in vitro or in a host cell, such as a bacteria, yeast, mammalian cell, etc. Kits may also be provided including a DNA molecule, such as a primer or probe, having a polynucleotide sequence comprising at least a portion of the human VMA21 gene or locus and containing one or more of the herein identified mutations in the human VMA21 gene in combination with one or more reagents, which may also optionally include written instructions. According to some embodiments, a mutant protein comprising at least a portion of the human VMA21 protein is provided having an amino acid mutation or substitution caused by the presence of one of the herein identified mutations. For example, such a mutant human VMA21 protein may be expressed from a DNA molecule having the c.272G>C mutation, such that the glycine (Gly) at amino acid position 91 of the mutant human VMA21 protein (based on the numbering of amino acids for the VMA protein translated from the main mRNA transcript) is mutated or replaced with an alanine (Ala). The same mutation may also be present in the human VMA21 protein translated from an alternatively spliced transcript. According to some embodiments, such a mutant human VMA21 protein may be used to generate mutation-specific antibodies according to known techniques.

According to another broad aspect of the present invention, cells are provided that are cultured from an individual or patient having a particular type or form of vacuolar or vacuolated myopathy, such as an individual or patient having XMEA, infantile autophagic vacuolar myopathy, or X-linked congenital autophagic vacuolar myopathy, wherein such cells contain one or more of the herein identified mutations in the VMA21 gene or genomic locus on the X chromosome. Such cells may be immortalized to form a cell line, and such cells may provide a basis or model for improved study of disease. These cell lines may be characterized by having one or more of the herein identified mutations in the VMA21 gene or locus on the X chromosome and/or by their reduced level and/or activity of the V-ATPase complex. As mentioned below, V-ATPase activity has been linked to pathology and pathogenicity of a number of diseases and infectious agents, including for example, cancer, malaria, viral infection, and osteoporosis to name a few. Therefore, such cell line compositions may be extraordinarily useful for studying V-ATPase function and for exploring possible disease interventions and therapies, including identification of possible drug candidates or gene therapies for treatment of disease.

Having described the many embodiments of the present invention in detail, it will be apparent that modifications and variations are possible without departing from the scope of the invention defined in the appended claims. Furthermore, it should be appreciated that all examples in the present disclosure, while illustrating many embodiments of the invention, are provided as non-limiting examples and are, therefore, not to be taken as limiting the various aspects so illustrated.

EXAMPLES

Hypomorphic Mutations in the LOC203547 Gene Cause XMEA

Figure 6A:
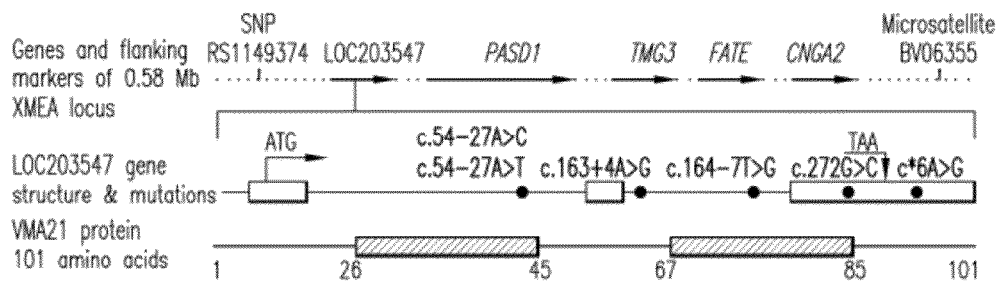
FIG. 6A is a diagram of a 0.58 Mb genomic locus of the X chromosome showing 5 genes including LOC203547 (top), a diagram of the gene structure of LOC203547 with three main exons indicated as open rectangles showing mutations identified (middle), and a diagram of the VMA21 protein translated from the main transcript with two predicted transmembrane domains indicated as grey rectangles (bottom)

The XMEA gene was previously mapped to Xq28. See, e.g. Auranen, M. et al., "X-linked vacuolar myopathies: two separate loci and refined genetic mapping," *Ann Neurol* 47:666-669 (2000); Minassian, B. et al., "Narrowing in on the causative defect of an intriguing X-linked myopathy with excessive autophagy," *Neurology* 59:596-601 (2002a); Villard, L. et al., "Linkage of X-linked myopathy with excessive autophagy (XMEA) to Xq28," *Eur J Hum Genet.* 8:125-129 (2000), the entire contents and disclosures of which are hereby incorporated by reference. The XMEA locus is further refined to a 0.58 Mb region containing four known genes and a fifth, LOC203547, predicted on the basis of multiple ESTs and mRNAs. Upon sequencing exons and flanking intronic sequences of all five genes in XMEA patients from 14 families, sequence changes are found in only LOC203547 (FIG. 6A). These changes are found in all patients and segregated with the disease in all families. To confirm that the changes are mutations, LOC203547 is sequenced in over 450 chromosomes from unaffected individuals, including about 100 chromosomes for each mutation from controls ethnically matched to the patient carrying the mutation (see table in FIG. 5). None of the normal individuals have any of these changes.

LOC203547 has three main exons, and a 4.7 Kb transcript is expressed in all tissues (FIGS. 3, 4, 6A, and 7). Most of the mutations identified in XMEA patients are located in splicing-relevant sites (FIG. 5). The predicted and actual outcome of all mutations is a decrease but not a complete elimination of wild-type LOC203547 mRNA. The mutations identified in XMEA patients consist of six different single-nucleotide substitutions (FIGS. 3, 4, 5, 6A and 8). The first two, "c.54–27A>T" and "c.54–27A>C," eliminate the A nucleotide predicted to define the first intron's splice branch point. The third, "c.163+4A>G," removes the A in the +4 position after exon 2 that is necessary for optimal U1 snRNA binding during splicing. The fourth, "c.164–7T>G," disrupts the polypyrimidine tract in intron 2, which would reduce the U2AF splice factor binding efficiency. A fifth, "c.272G>C," is in the coding sequence of LOC203547 replacing a glycine with alanine, but it also abolishes a predicted splice enhancer site. The sixth, "c.*6A>G," is in the 3'UTR.

Figure 6B:
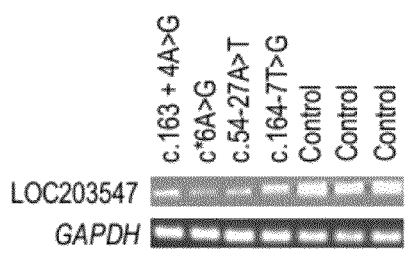
FIG. 6B is an image of a gel showing LOC203547 RT-PCR products using RNA extracts from lymphocytes of patients having the indicated mutations relative to controls with endogenous GAPDH expression used as control of starting mRNA amount.
Figure 6D:
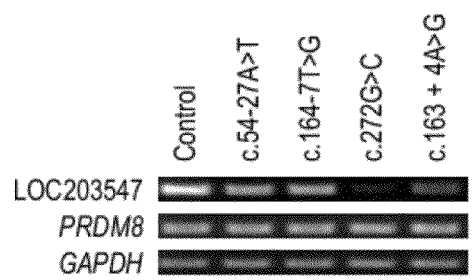
FIG. 6D is an image of a gel showing LOC203547 RT-PCR products using RNA extracts from C2C12 myoblasts transfected with the indicated minigene constructs with the PRDM8 gene co-transfected as a transfection efficiency control and endogenous GAPDH expression used as control of starting mRNA amount.
Figure 6C:
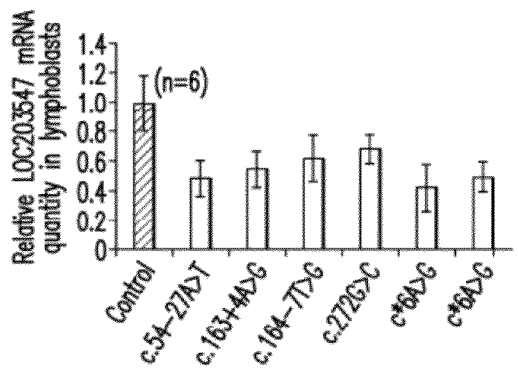
FIG. 6C is a bar graph showing LOC203547 quantitative RT-PCR levels of products from lymphocytes of patients having the indicated mutations relative to controls and measured as a ratio to β-actin (Each bar represents the mean±standard deviation of three independent experiments)
Figure 6E:
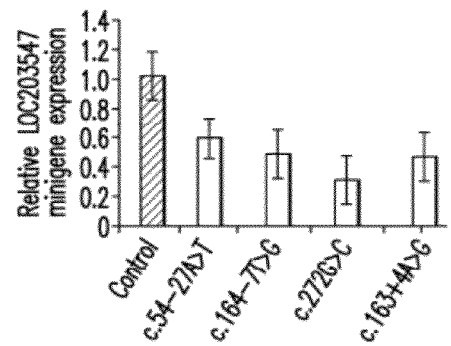
FIG. 6E is a bar graph showing LOC203547 quantitative RT-PCR levels of products from C2C12 myoblasts transfected with the indicated minigene constructs relative to controls and measured as a ratio to β-actin (Each bar represents the mean±standard deviation of three independent experiments)
Figure 8:
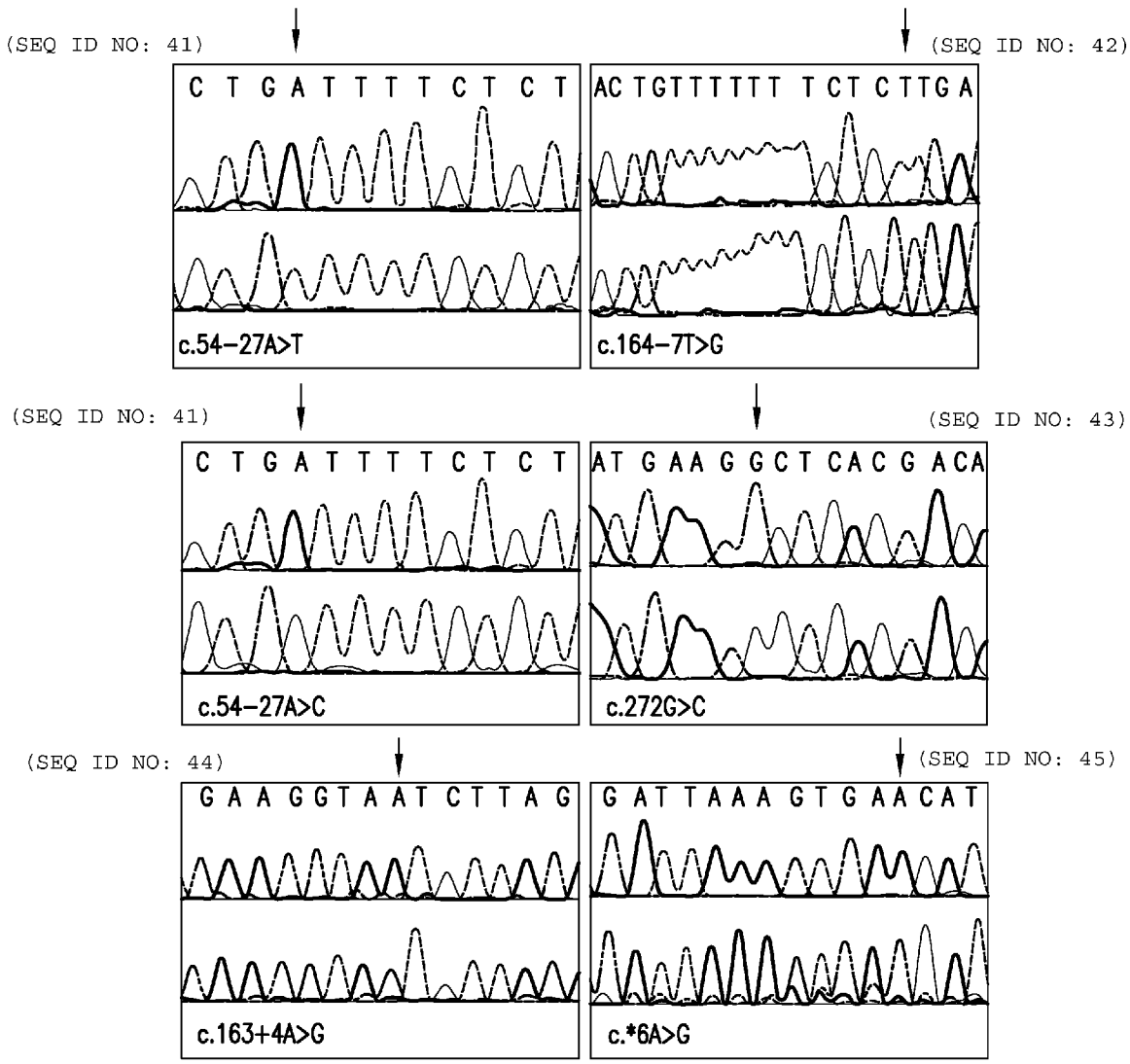
FIG. 8 is a set of sequence electropherograms of LOC203547 showing normal sequence with positions of mutations in XMEA indicated by arrows.

Splice site mutations may cause disease by generating abnormal splice forms, or by decreasing mRNA quantity through reduced splicing efficiency. Splice variants are not observed with the observed mutations, but quantitative RT-PCR (qRT-PCR) in lymphoblasts revealed about 32-58% reduction in LOC203547 mRNA levels in all patients, including those with the 3'UTR mutations (FIGS. 6B and 6C). To confirm that these reductions are directly caused by the LOC203547 mutations (and are not secondary disease effects), minigene constructs are created for each of the splice site mutations (FIG. 9) and expressed in C2C12 myoblasts. In these experiments, the only difference between these mutant minigene constructs relative to a control minigene construct is the one LOC203547 nucleotide mutated in each patient. qRT-PCR show greater than about 40% decrease in LOC203547 mRNA from the mutant minigene constructs compared to controls (FIGS. 6D and 6E), confirming that LOC203547 mutations downregulate LOC203547 mRNA. LOC203547 is the Human Orthologue of the Yeast V-ATPase Assembly Chaperone Vma21p Higher eukaryote orthologues of the yeast Vma21p protein are not evident, but two have been suggested on the basis of weak sequence similarity (i.e., having less than 18% identity). See, e.g., Ludwig, J. et al., "Identification and characterization of a novel 9.2-kDa membrane sector-associated protein of vacuolar proton-ATPase from chromaffin granules," *J Biol Chem* 273:10939-10947 (1998); and Malkus, P. et al. (2004), supra, the entire contents and disclosures of which are hereby incorporated by reference. One suggested orthologue, NP_003936, was recently disproved. See, e.g., Sambade, M. et al., "The yeast vacuolar proton-translocating ATPase contains a subunit homologous to the *Manduca sexta* and bovine e subunits that is essential for function," *J Biol Chem* 279:17361-17365 (2004), the entire contents and disclosures of which are hereby incorporated by reference. The other suggested orthologue is LOC203547. See, e.g. Malkus, P. et al. (2004), supra.

Figure 10A:
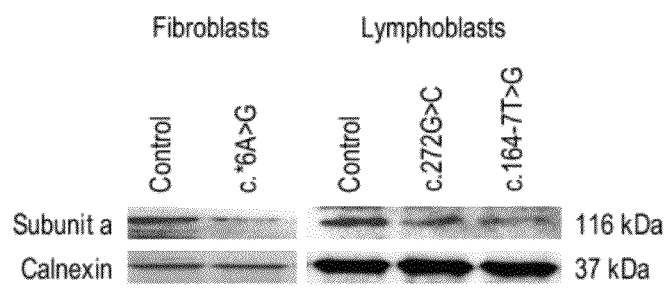
FIG. 10A is a set of Western blots showing the levels of $V_O$ "subunit a" in light membrane fractions of fibroblasts and lymphoblasts from patients having the indicated mutations relative to control with loading intensities normalized to calnexin.
Figure 10B:
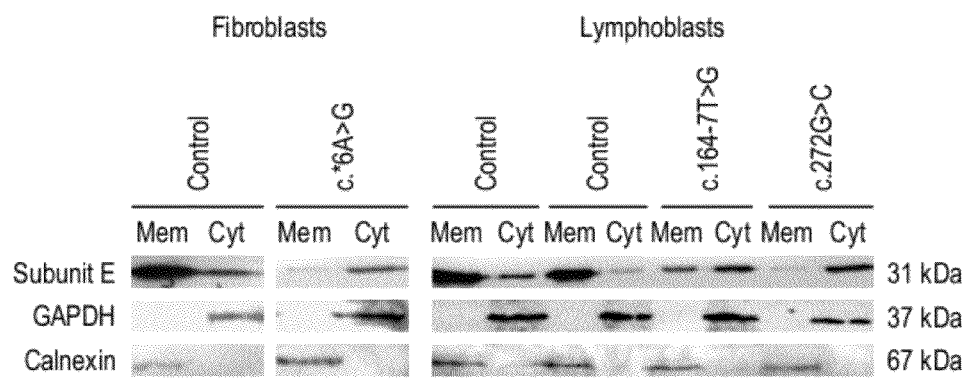
FIG. 10B is a set of Western blots showing the levels of $V_1$ "subunit E" in light membrane and cytosolic fractions of fibroblasts and lymphoblasts from patients having the indicated mutations relative to control with loading intensities normalized to calnexin and GADPH used as a positive and negative control for the two fractions.
Figure 10C:
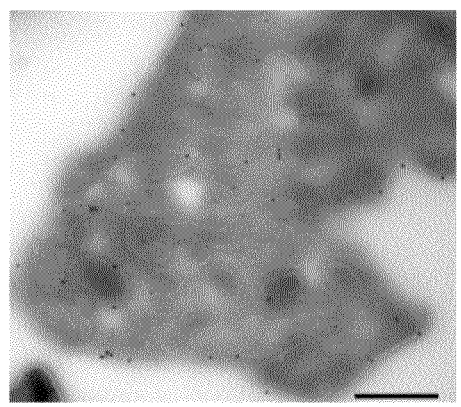
FIG. 10C is an image of an electron micrograph of an ultrathin cryosection of neutrophils from a normal individual that is immunogold labeled for the $V_0$ "subunit a" (bar=0.5 µm)
Figure 10D:
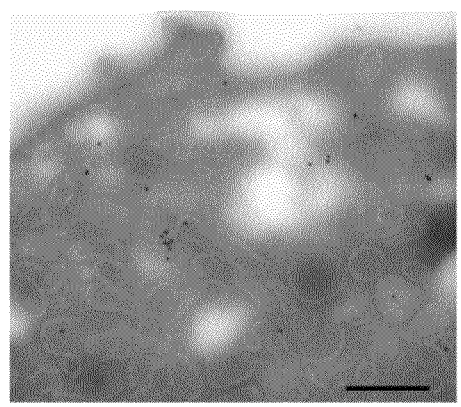
FIG. 10D is an image of an electron micrograph of an ultrathin cryosection of neutrophils from a XMEA patient that is immunogold labeled for the $V_0$ "subunit a" (bar=0.5 µm)

To find out whether LOC203547 is the human orthologue of yeast Vma21p, it is determined whether its downregulation in XMEA affects V-ATPase activity, and whether this effect on V-ATPase activity is the same as the previously characterized effect of Vma21p deficiency on the V-ATPase in yeast. The yeast vma21 deletion mutant (vma21Δ) have defective growth and drastically reduced numbers of V-ATPases and V-ATPase activity in organellar membranes. vma21Δ mutant yeast also exhibit increased $V_1$ sector proteins in its cytosol. Normally, $V_1$ subunits are produced in the cytosol and added later onto the ER-assembled $V_0$ sector. In vma21Δ mutants, $V_0$ assembly fails. As a result, $V_1$ proteins can no longer find $V_0$ matches and therefore accumulate in the cytosol. See, e.g. Malkus, P. et al. (2004), supra. In light membrane fraction (includes all organelles) of XMEA patient lymphoblast extracts, V-ATPase activity is reduced to a range of 12% to 22% of normal levels (FIG. 6F). In fibroblasts, V-ATPase activity is reduced to 11-13% of normal, and in fresh-frozen muscle biopsies, V-ATPase activity is reduced to 21-33% of normal (FIG. 6G). Western blot analysis of light membrane fractions shows that levels of V-ATPase proteins (i.e., $V_0$ subunit a; and $V_1$ subunit E) are reduced (FIGS. 10A and 10B), indicating that the decreased V-ATPase activity is due to decreased assembly and numbers of organellar V-ATPases. The band intensities of $V_0$ "subunit a" levels (normalized to calnexin) are: c.*6A>G, 0.4±0.07; c.272G>C, 0.32±0.02; c.164–7T>G, 0.36±0.03 with control individuals set at 1.0. This is confirmed by directly counting V-ATPases on intact organelle membranes of intact cells using immunogold electron microscopy (FIGS. 10C and 10D). In the XMEA patient (FIG. 10D), gold particle density is reduced from the plasma membrane and from the membranes of neutrophil phagosomes compared to a control (FIG. 10C). Actual mean counts from 150 neutrophils from three controls (50 cells per control) and 100 neutrophils from two patients (50 cells per patient) are as follows: control plasma membrane, 2.7±0.5 particles/linear μm; patient plasma membrane, 0.4±0.1 particles/linear μm; control phagosome membrane, 4.3±0.75 particles/linear μm; and patient phagosome membrane, 1.25±0.06 particles/linear μm; significance<0.001 using student's T test. Additional western blot results show that subunit E is increased in the cytosolic fraction in XMEA patients by the same amount that it is decreased in organellar membranes (FIG. 10B), as similarly occurs in vma21p deficient yeast. The band intensities of $V_1$ "subunit E" levels (normalized to calnexin) in membrane (Mem) and cytosolic (Cyt) fractions are: c.6*A>G, 0.32±0.14 (Mem) and 1.23±0.24 (Cyt); c.272G>C, 0.44±0.04 (Mem) and 1.36±0.17 (Cyt); c.164−7T>G, 0.27±0.03 (Mem) and 1.42±0.11 (Cyt).

Figure 11:
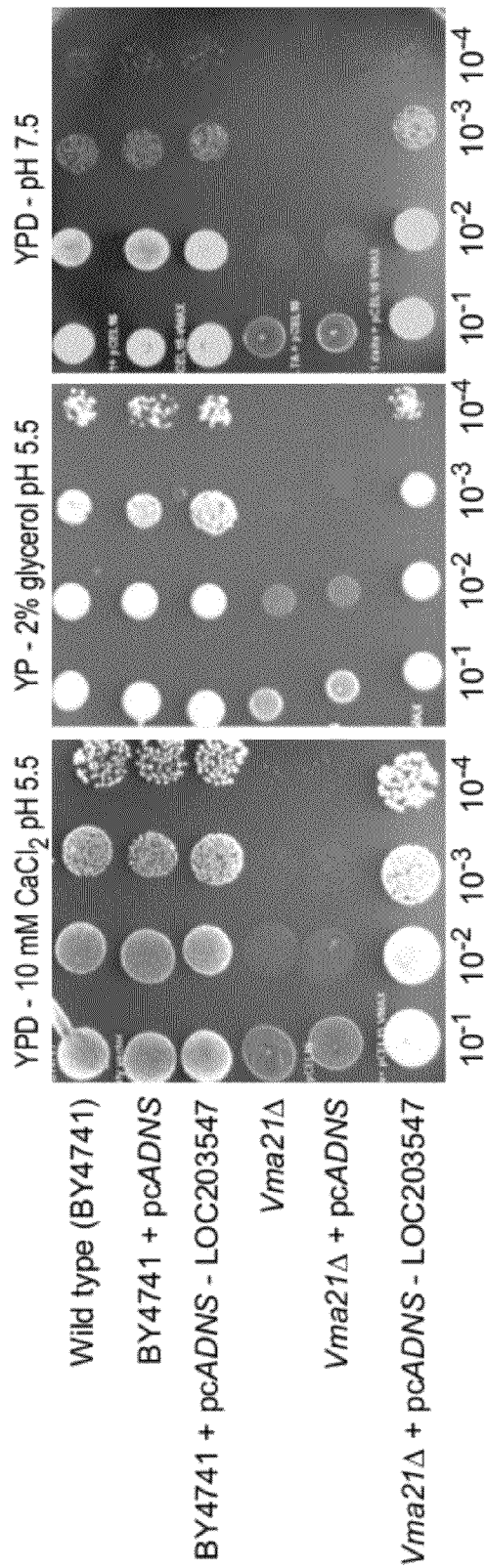
FIG. 11 is a set of images showing synchronous growth of BY4741 (wild-type) and Vma21Δ yeast cultures with or without transformation of pcADNS or pcADNS-LOC20354 at four successive dilutions ($10^{-1}$-$10^{-4}$) in three different growth media.

It is next determined whether LOC203547 can complement vma21Δ in yeast. The vma21Δ yeast strain is characterized by a well-defined set of growth defects including stunted growth on complete media, and lack of growth on media with nonfermentable carbon sources or on media with elevated pH or calcium (Malkus, P. et al. (2004), supra). vma21Δ, LOC203547-transformed vma21Δ, and wild-type (BY4741) yeast are cultured for three days in YP-glycerol pH 5.5 (glycerol as carbon source), YPD pH 7.0 (elevated pH), and YPD pH 5.5 with 10 mM $CaCl_2$. vma21Δ yeast show their characteristic negligible growth, while LOC203547-transformed vma21Δ grow proficiently and equally to wild-type BY4741 on all three media (FIG. 11) showing that LOC203547 fully rescues vma21Δ. Collectively, the foregoing results strongly establish that LOC203547 is the human orthologue of yeast Vma21p. Hereinafter, the putative human LOC203547 gene is referred to as "VMA21."

The Subcellular Stations of VMA21 Diverge from Those of Vma21p

The cellular locations frequented by VMA21 in mammalian cells are analyzed in comparison to Vma21p in yeast. The cellular locations of Vma21p in yeast and its activity in these locations have been extensively studied and are briefly reviewed here. Vma21p first interacts in the ER membrane with the V-ATPase "subunit c'." This initiates a stepwise assembly of all the other $V_0$ components, including the large "subunit a," and presence of Vma21p is necessary throughout the process. "Subunit a" is the last to join the complex. It is folded and readied to join by chaperones Vma12p and Vma22p. There are two isoforms of "subunit a," either of which can be used. Once $V_0$ is fully formed, Vma21p accompanies it, via COPII vesicles, to the Golgi apparatus. Whether $V_1$ subunits are added before or after $V_0$ is transferred to Golgi, or both, remains unclear. See, e.g. Malkus, P. et al. (2004), supra; and Ochotny, N. et al., "Effects of human a3 and a4 mutations that result in osteopetrosis and distal renal tubular acidosis on yeast V-ATPase expression and activity," *J Biol Chem* 281:26102-26111 (2006). Vma21p and the V-ATPase part company at the Golgi. Vma21p is retargeted by its c-terminal dilysine signal to the ER, while the V-ATPase continues on to its final destination, which depends on which of the two "subunit a" isoforms were originally incorporated.

Figure 12:
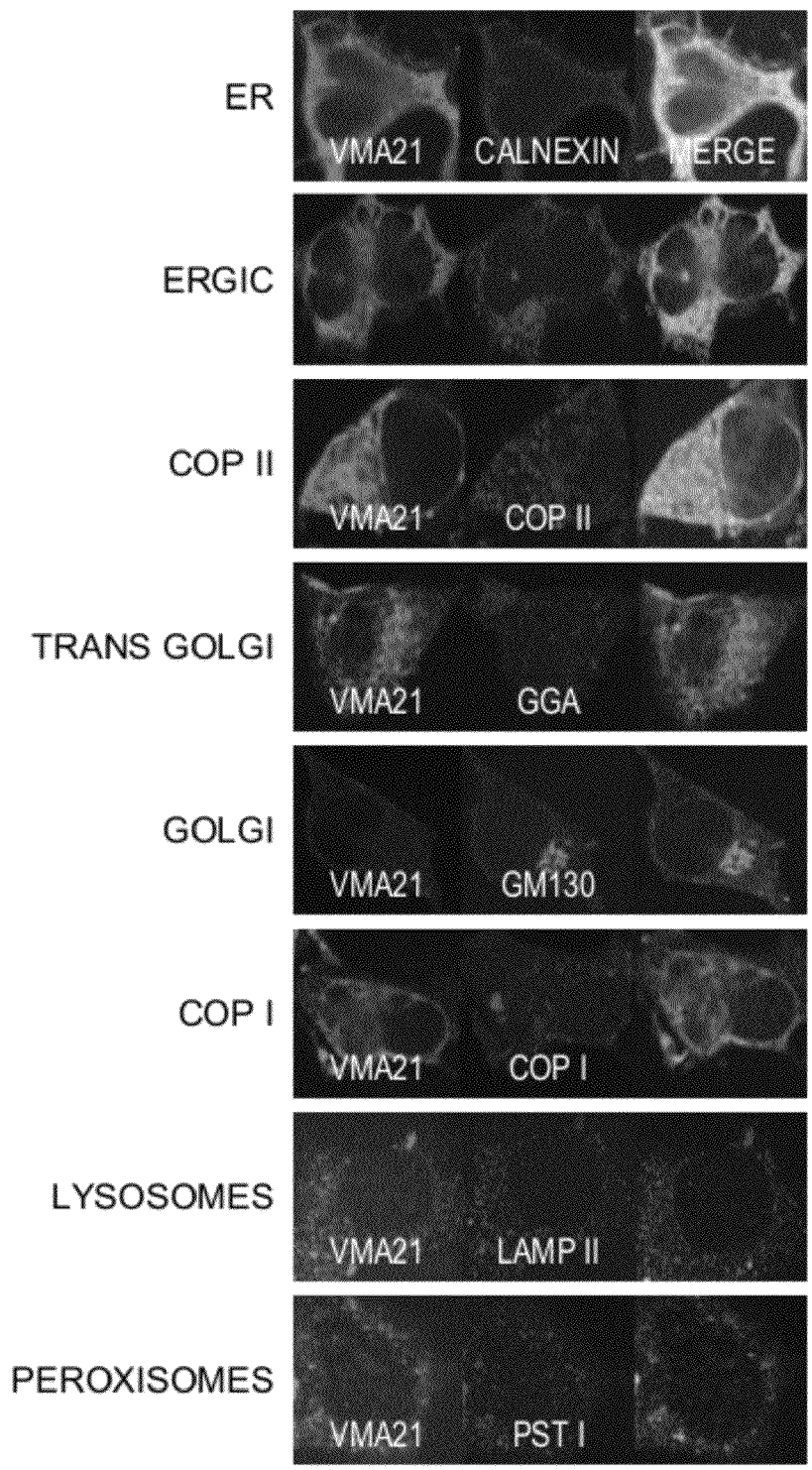
FIG. 12 is a set of images of immunofluorescent staining of COS7 cells transfected with pcDNA 3.1-VMA21-myc expressing a myc-tagged VMA21 protein using a myc antibody to detect VMA21 (left column) and co-stained with antibodies against compartment-specific markers (middle column) with the merged image shown (left column; yellow indicating co-localization)

While yeast has two "subunit a" isoforms, human cells have a choice of four isoforms: "subunit a1" used ubiquitously for most V-ATPases of most cells, "subunit a2" used for particular Golgi and early-endosome V-ATPases in certain cells, "subunit a3" for plasma membrane V-ATPases of osteoclasts, and "subunit a4" for plasma membrane V-ATPases of certain renal and inner ear cells. See, e.g., Hurtado-Lorenzo, A. et al., "V-ATPase interacts with ARNO and Arf6 in early endosomes and regulates the protein degradative pathway," *Nat Cell Biol* 8:124-136 (2006); Komak, U. et al. (2008), supra; Manolson, M. F. et al., "The a3 isoform of the 100-kDa V-ATPase subunit is highly but differentially expressed in large (> or =10 nuclei) and small (< or =nuclei) osteoclasts," *J Biol Chem* 278:49271-49278 (2003); Karet, F. E. et al. (1999), supra.

myc epitope tagged VMA21 is expressed in COS7 cells that are double-stained with myc and organelle specific antibodies. Using immunofluorescence light microscopy and immunogold electron microscopy (not shown), it is found that VMA21 localizes to the ER, but not to mitochondria, peroxisomes or lysosomes. VMA21 does not localize to Golgi, nor cis- or trans-golgi networks. However, it does localize to the ER-Golgi Intermediate Compartment (ERGIC) and to COPII vesicles, but not to COPI vesicles (FIG. 12). VMA21 lacks a dilysine ER return signal, predicting that unlike Vma21p it may not recirculate to the ER. Consistently, we do not see VMA21 on COPI vesicles, which are considered the return vehicles for Vma21p in yeast. Therefore, VMA21 appears to follow only part of the route of Vma21p in yeast cells, since VMA21 travels from ER to ERGIC but not beyond, and not back to ER, at least not via COPI vesicles.

Decreased, Increased, and 'Excessive' Autophagy in XMEA

Autophagy is the degradation of long-lived proteins and other cell components. It is composed chiefly of three lysosome dependent processes. In chaperone-mediated autophagy, the lysosome takes in proteins to be degraded via receptors. In microautophagy, the lysosome encloses the components to digest. In macroautophagy, the process begins with an isolation membrane appearing in the cytoplasm and surrounding targeted constituents. This autophagosome rapidly fuses with a lysosome at which point it is called autolysosome possessing lysosomal pH, V-ATPases, and hydrolases, which digest its contents. Macroautophagy is a larger contributor to autophagy than the two non-macro autophagic processes. See, e.g., Mizushima, N. et al., "Autophagosome formation in mammalian cells," *Cell Struct Funct* 27:421-429 (2002).

Figure 13A:
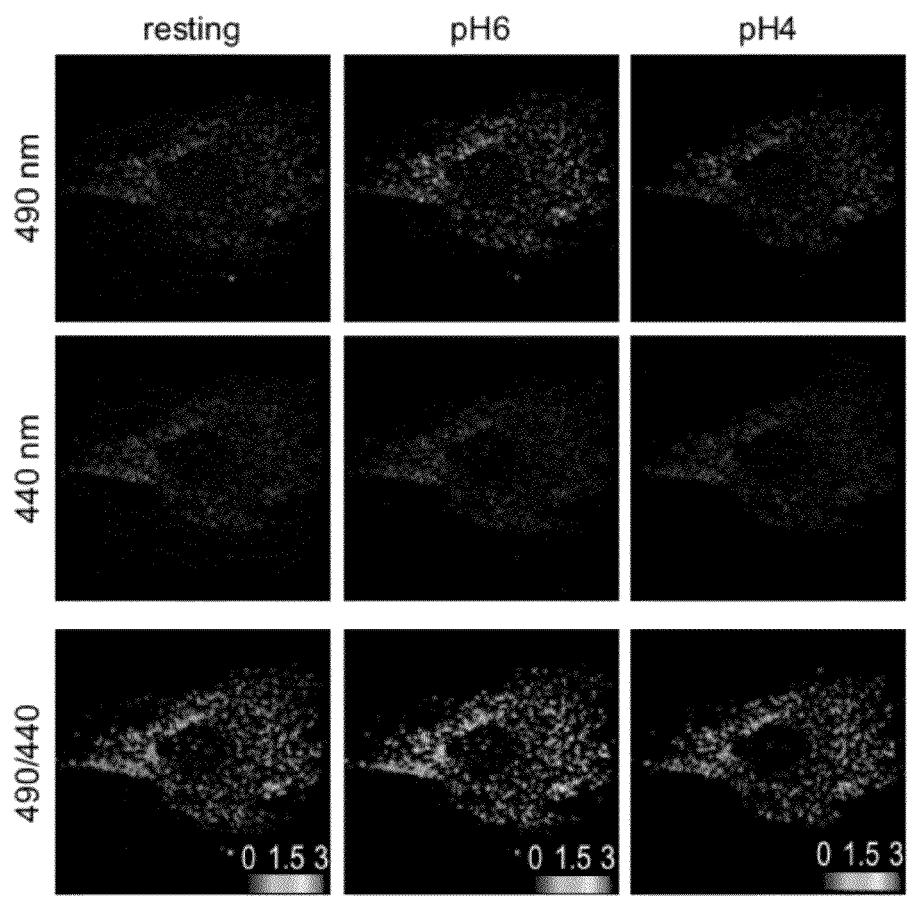
FIG. 13A is a set of live-cell ratiometric fluorescence images used to measure lysosome pH of lysosomes loaded with Oregon Green 514-coupled dextran with images acquired at 490 nm (pH sensitive wavelength) and 440 nm (reference wavelength) under varying pH environments.
Figure 13B:
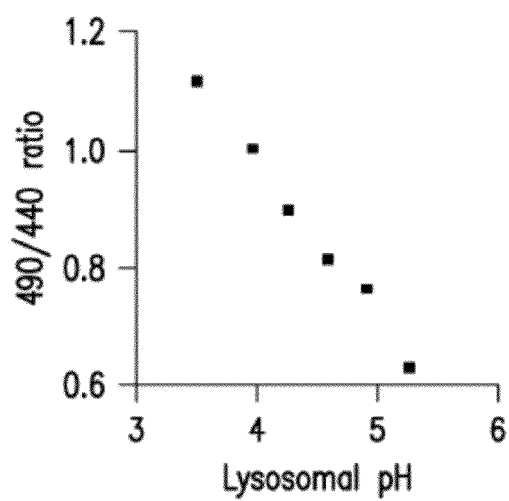
FIG. 13B is a calibration curve generated from the data obtained from the live-cell ratiometric fluorescence images constructed from the ratio of intensity measurements of selected ROI and plotted against corresponding pH values using linear regression methods.
Figure 14A:
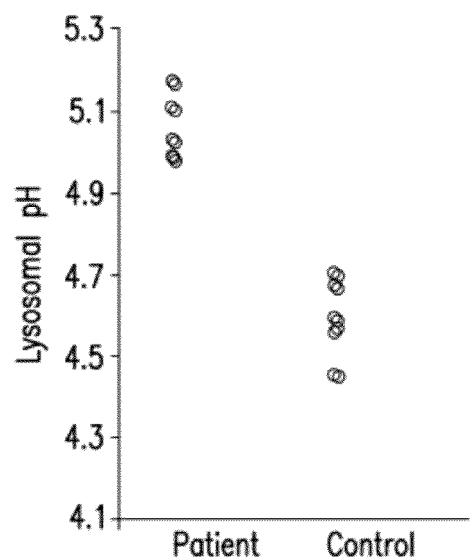
FIG. 14A is a plot showing the spread of lysosomal pH values in patient and control fibroblasts with each symbol displayed representing the mean of 10 lysosomes per cell from 11 subjects.

Based on the present findings of decreased V-ATPase activity, elevated lysosomal pH, decreased lysosomal hydrolase activities, and decreased autophagy is predicted in XMEA. To measure lysosomal pH, fibroblasts are incubated with Oregon green dextran overnight, during which time the dextran is endocytosed to the lysosome where it fluoresces with an intensity proportional to pH and emits two wavelengths around an isobestic point (i.e., fluorescence intensity at one wavelength is inversely proportional to the intensity at the other and the ratio of intensities corrects for focal plane and other artifacts) (FIGS. 13A and 13B). See, e.g., Paroutis, P. et al., "The pH of the secretory pathway: measurement, determinants, and regulation," *Physiology (Bethesda)* 19:207-215 (2004), the entire contents and disclosure of which is hereby incorporated by reference. The pH of patient lysosomes is about 0.5 units higher (i.e., about three times less [$H^+$]) than that of controls (FIG. 14A).

Figure 14B:
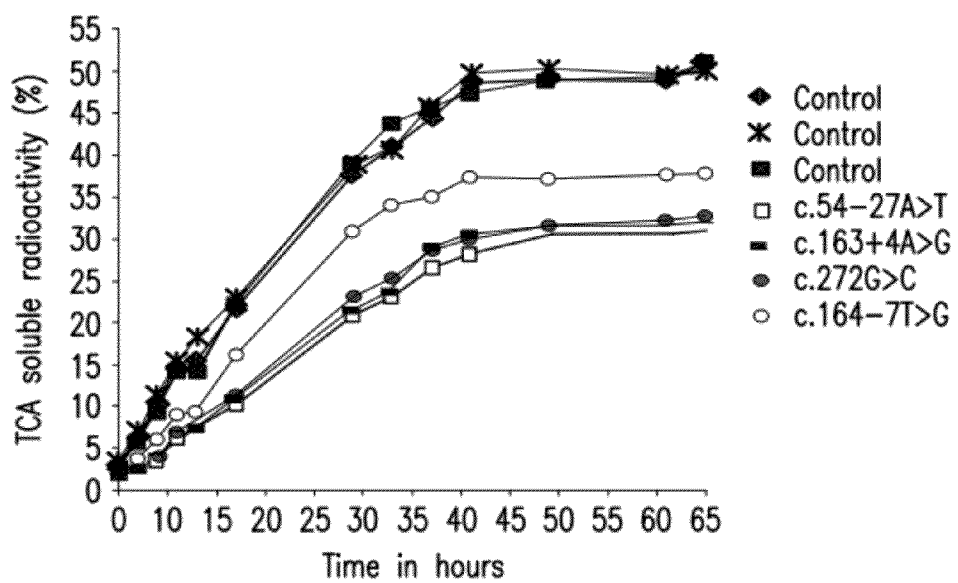
FIG. 14B is a time course plot of TCA soluble radioactivity (%) showing a chase of lysosome dependent long-lived protein degradation in lymphoblasts from patients having the indicated mutations relative to controls with chase media containing MG-132 to eliminate proteasomal contribution and with non-lysosomal proteolysis measured in cells cultured in parallel in media containing $NH_4Cl$/leupeptin subtracted from total proteolysis.

Autophagy is measured by quantifying the degradation of long-lived proteins. Lymphoblasts are cultured for 48 hours in media with [$S^{35}$]cysteine and [$S^{35}$]methionine. After washing, the cells are maintained with no further radioactivity, and chased protein degradation is measured in the trichloroacetic acid-soluble fraction of total radioactivity at different time points for 72 hours. Chase media of three types are used to allow calculation of total autophagy, macroautophagy, and non-macro autophagy: routine media, media with inhibitors of all lysosomal proteases ($NH_4Cl$ and leupeptin), and media containing 3-methyl adenine, a specific inhibitor of macroautophagy. In controls and XMEA patients, approximately half of long-lived protein degradation is macroautophagic and about half of the degradation is through non-macro autophagy. However, total long-lived protein degradation in patients is 25 to 50% lower in XMEA patients than in controls, and this reduction in autophagic flux is due about equally to reductions in macro and non-macro autophagies (FIGS. 14B and 14C), with non-lysosomal proteolysis negligible (i.e., <3% of lysosomal proteolysis) and unvarying over time. In separate experiments, proteolysis of short-lived proteins, which is largely proteasomal and non-lysosomal, is unaffected (not shown).

Figure 15:
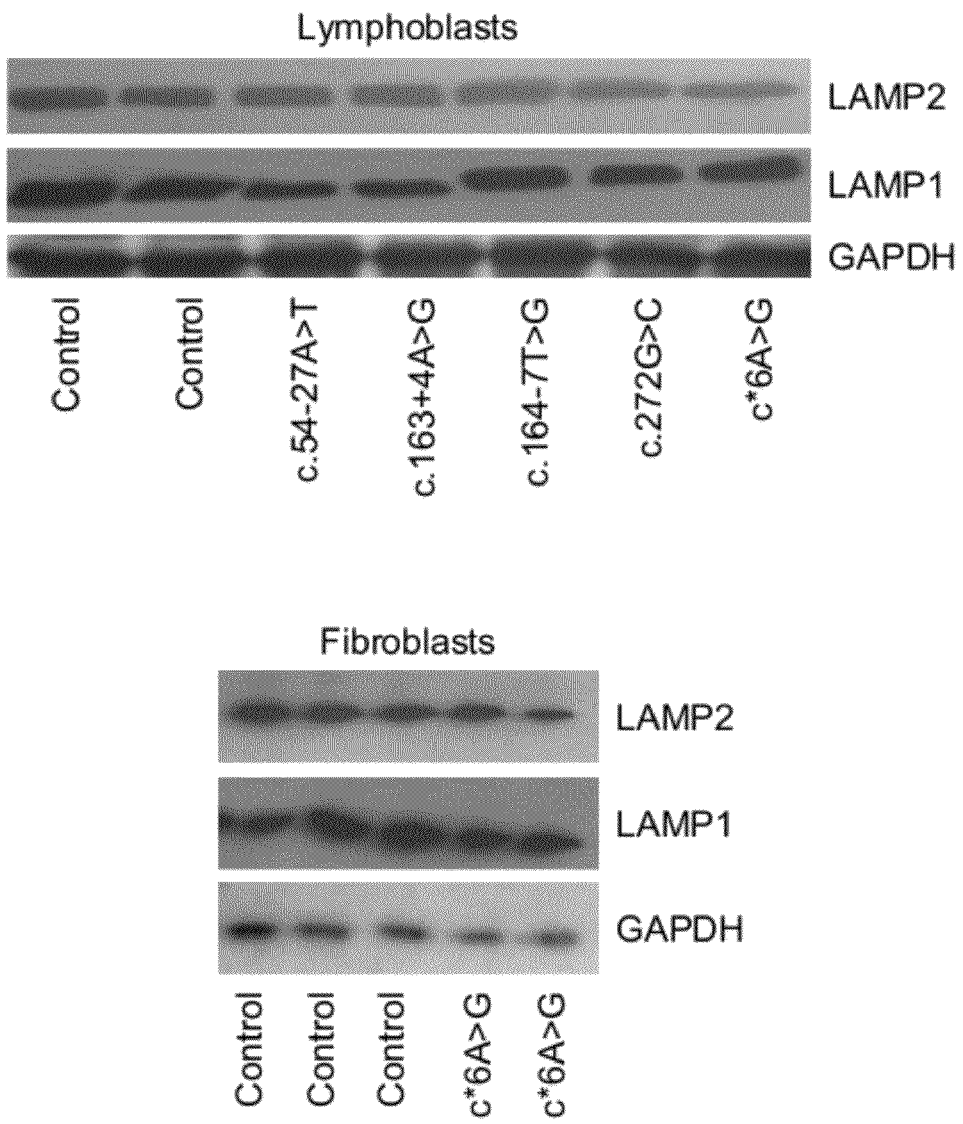
FIG. 15 is a set of Western blots for lysosomal membrane proteins LAMP1 and LAMP2 in total protein extracts from lymphoblasts and fibroblasts from patients with the indicated mutations and control individuals.

It is possible that a compensatory upregulation of macroautophagy occurs in response to the functional defect in autophagy, which may then cause the 'excessive autophagy' and/or autophagic vacuolation present in XMEA patients. Macroautophagic activity is first assessed through the LC3 protein. In the cytosol, LC3 is in an 18 kD form (LC3-I). Upon activation of macroautophagy, LC3 is converted into LC3-II (16 kD), which functions as a key constituent of the isolation membrane that forms the autophagosome. The LC3-II is then degraded once the autophagosome merges with lysosomes. See, e.g. Mizushima, N. et al. (2002), supra. LC3 western blots performed with lymphoblast and fibroblast lysates show that LC3-II is drastically increased in patients compared to controls (FIG. 14D). LC3 is also measured at the transcriptional level showing about a two-fold (i.e., about a 1.5 to 2-fold) increase in LC3 mRNA in patients (FIG. 14E). mRNA levels of a second macroautophagy-specific gene, ATG12, are also quantitated showing a ten-fold elevation in patients relative to a control (FIG. 14F). The product of the ATG12 gene functions immediately upstream of LC3. See, e.g. Mizushima, N. "Autophagy: process and function," *Genes Dev* 21:2861-2873 (2007); and Mizushima, N. et al. (2002), supra, the entire contents and disclosure of which is hereby incorporated by reference. Taken together, these results indicate upregulation of macroautophagy and increased autophagosome generation activity in XMEA. It is also asked whether lysosomes, the second arm of macroautophagy, are also increased. Western blots of lysosomal membrane proteins LAMP1 and LAMP2 show no difference between patients and controls (FIG. 15), indicating no increase in lysosomes.

Figure 16A:
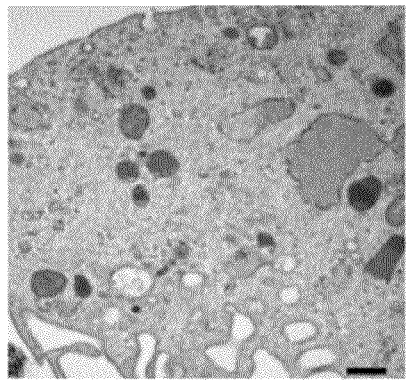
FIG. 16A is an image generated by electron microscopy showing a representative example of the ultrastructural morphological features of XMEA patient fibroblasts with an extensive number of autolysosomes distributed throughout the cell (bar=2 µm)
Figure 16B:
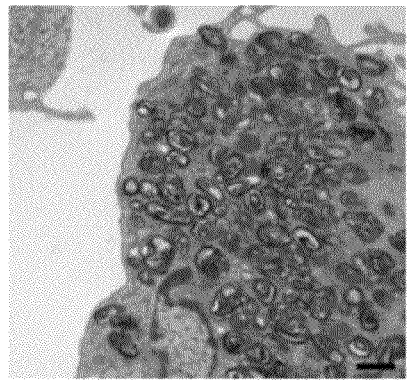
FIG. 16B is a higher power view of the image in FIG. 16A showing excellent preservation of the ultrastructural morphological features of the cell (note mitochondria, nucleus and ER) despite the presence of the autolysosomes (bar=0.5 µm)
Figure 17A:
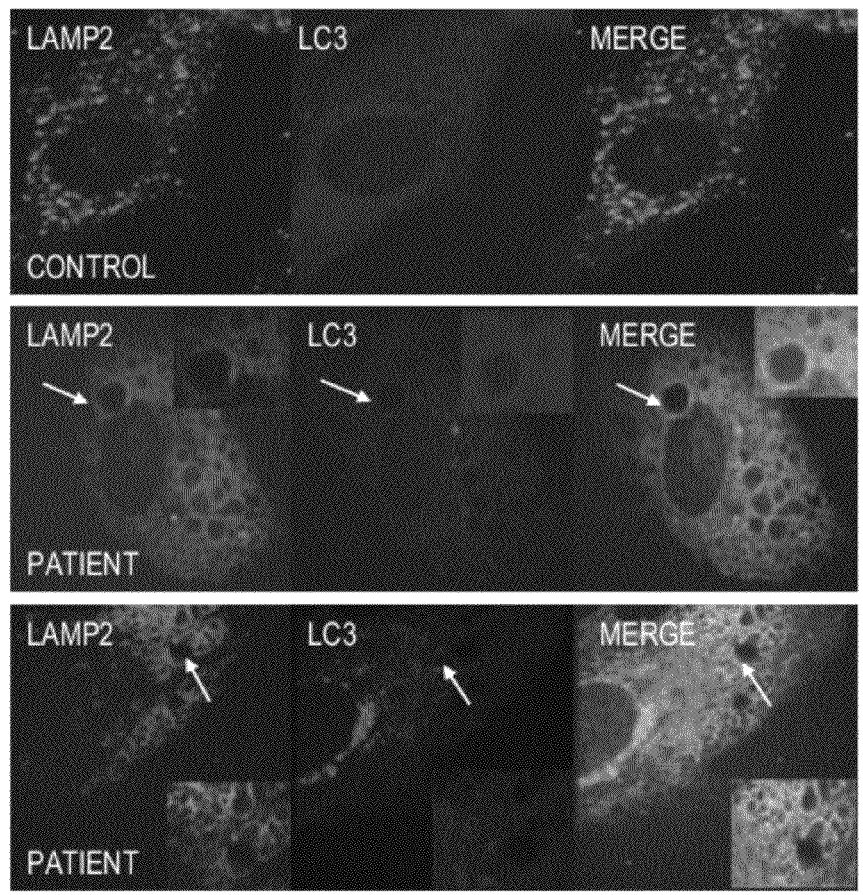
FIG. 17A is a set of images generated by immunofluorescence light microscopy showing punctuate LAMP2 (lysosomes) and diffuse LC3 signal in control fibroblasts (top panel) and showing LC3 and/or LAMP2 positive autolysosomes in patient fibroblasts (middle and lower panels) with normal-sized lysosomes still present and arrows indicating autolysosome regions shown at higher magnification in the insets.

Lymphoblasts and fibroblasts are also examined by electron microscopy. The vast majority of XMEA cells (about 95%), and none of the control cells, exhibited a great proliferation of membrane-bound spherical structures with morphologic features of autophagosomes or autolysosomes (FIGS. 16A and 16B). With a size of about 0.5 μm, these structures are twice the size of lysosomes, similar in size to autophagosomes and autolysosomes of cells in starvation mode, and about 20 times smaller than the giant autophagic vacuoles seen in XMEA muscle. See, e.g. Mizushima, N. et al., "In vivo analysis of autophagy in response to nutrient starvation using transgenic mice expressing a fluorescent autophagosome marker," *Mol Biol Cell* 15:1101-1111 (2004), the entire contents and disclosure of which is hereby incorporated by reference. Immunofluorescence light microscopy using LC3 and LAMP2 antibodies shows that the membranes of these structures are positive for LC3 and LAMP2, indicating autophagosomes transitioning to autolysosomes, or for LAMP2 alone, indicating mature autolysosomes (FIG. 17A). Both the transitional form and the mature autolysosome are hereinafter referred to as autolysosomes. Normally, autolysosomes are evanescent organelles with a very short life, rapidly degrading their contents and hardly detectable in normal cells. Their presence in such large numbers in XMEA is consistent with the decreased macroautophagic flux, since their lives may be extended by their ineffective and prolonged degradation of contents.

The number of normal-sized lysosomes (punctuate LAMP2 signal) is drastically reduced in XMEA cells compared to controls, and in some cases, the number of normal-sized lysosomes is close to none (FIG. 17A). It appears that the vast majority of lysosomes are recruited into autolysosomes but are not replaced with new normal-sized lysosomes.

Figure 16C:
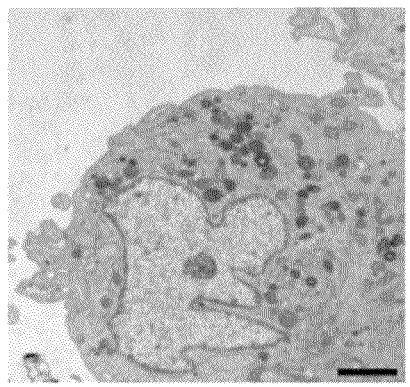
FIG. 16C is an image generated by electron microscopy showing a representative example of the minority of patient cells exhibiting giant autophagic vacuolation (bar=0.5 µm)
Figure 16D:
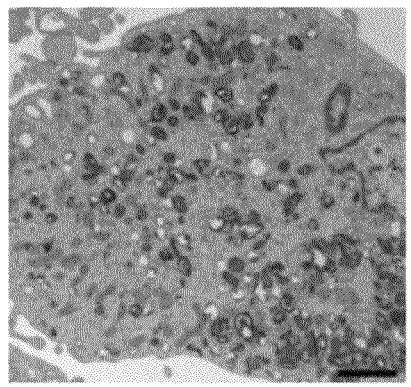
FIG. 16D is an image generated by electron microscopy showing a fibroblast from an unaffected individual (bar=2 µm)
Figure 16E:
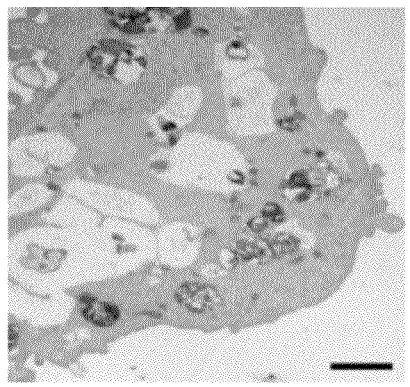
FIG. 16E is an image generated by electron microscopy showing a fibroblast from an affected individual which appears to be in the process of transitioning towards autophagic vacuolation (bar=2 µm)

Five percent of XMEA lymphoblasts and fibroblasts exhibit giant autophagic vacuoles like those in muscle (FIGS. 16C, 16D, and 16E) in addition to the autolysosome proliferation. This shows that the 'excessive autophagy' (or autophagic vacuolation) in XMEA does occur in cells other than muscle, albeit in a much smaller proportion (i.e., 5% compared to 40-80% in skeletal muscle of the same patients).

Not All Low-pH Dependent Functions are Affected in XMEA

Figure 17B:
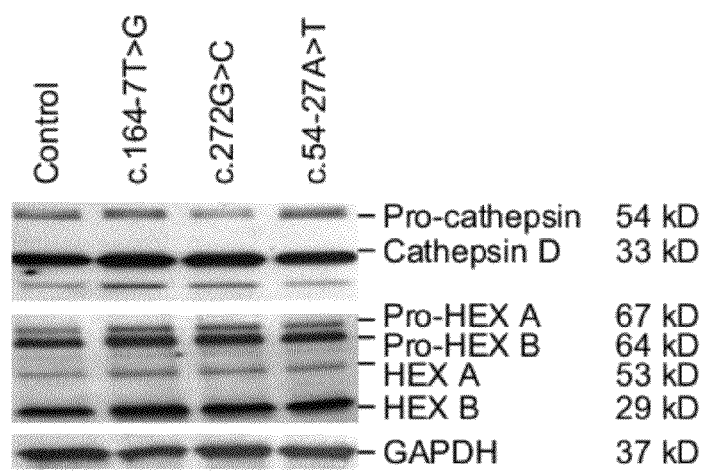
FIG. 17B is a set of Western blots probed for cathepsin D and hexosaminidase B using protein extracts from lymphoblasts derived from patients having the indicated mutations or controls with GADPH used as a loading control showing that proteolytic processing of these enzymes is unaffected.

Multiple cell systems in addition to autophagy are subserved by the V-ATPase, yet none is affected to a clinical extent in patients despite only 10-30% residual V-ATPase activity. One of these systems (i.e., maturation of lysosomal enzymes) is selected for study at the molecular level. This system is a three-step process depending on successively lower pH: mannose 6-phosphorylation in the Golgi (pH 6.5), removal of mannose in endosomes (pH 5.5) that transport the enzymes to the lysosome, and finally cleavage of pre-proteins into shorter active forms in the lysosome (pH 4.7). Maturations of hexosaminidase subunits A and B as well as cathepsin D in fibroblasts is analyzed. All three are shown to be normal at each of the maturational steps, including in the lysosome (FIG. 17B).

Materials and Methods

Mutation identification. A set of three primer pairs is designed from genomic DNA to amplify each exon of the VMA21 gene, including the flanking splice sites and the 5' and 3' UTRs. Fragments are PCR amplified (35 cycles) using the Taq DNA Polymerase (Fermentas) with (NH4)SO4 buffer and 20% betaine for the first exon and the PicoMaxx High Fidelity PCR system (Stratagene) for exons 2 and 3. Cycling conditions are: 94° C. for 30", 55° C. for 30", and 72° C. for 40". Products are sequenced forward and reverse. The following primer sequences are provided in FIG. 18: LOC203547-x1-F (SEQ ID NO: 14); LOC203547-x1-R (SEQ ID NO: 15); LOC203547-x2-F (SEQ ID NO: 16); LOC203547-x2-R (SEQ ID NO: 17); LOC203547-x3-F (SEQ ID NO: 18); and LOC203547-x3-R (SEQ ID NO: 19).

RT-PCR and quantitative real time PCR. Total RNA is isolated from cultured cells using the RNeasy Mini Kit (Qiagen). 1 μg of total RNA is converted from each sample into cDNA using oligo(dT) primers and the SuperScript First-Strand Synthesis System (Invitrogen). RT-PCR is performed with a 22-cycle standard amplification protocol. The relative standard curve technique is used to analyze the expression of VMA21 or minigene constructs normalized to β-actin expression in the same sample. The standard curve is prepared from either control lymphoblast or C2C12 cell cDNA at 1, 10, $10^2$, $10^3$, and $10^4$ dilution factors for each primer pair. Each reaction well contains 0.5 μL of template cDNA of appropriate concentration for linear amplification based on the standard curve, 100 ng of each primer, and 1×SYBR Green PCR Master Mix (Applied Biosystems) to a final volume of 20 μL. Reactions are carried out using an Applied Biosystems 7900HT Real-Time PCR System for 40 cycles (95.0° C. for 15" and 60° C. for 60"). The purity of the PCR products is determined by melting curve analysis. Within each plate, triplicates of each sample is included. Data are analyzed using the SDS2.1 v.2.1.0.3 (Applied Biosystems). At least three separate experiments per subject are performed. Values exceeding two standard deviations are excluded. Primers used for RT-PCR include: LOC203547-RT-F (SEQ ID NO: 20) and LOC203547-RT-R (SEQ ID NO: 21). Primers used for quantitative PCR (q-PCR) include: Q-LOC203547-F (SEQ ID NO: 22), Q-LOC203547-R (SEQ ID NO: 23), Q-BACT-F (SEQ ID NO: 24), Q-BACT-R (SEQ ID NO: 25), LC3B-F (SEQ ID NO: 26), LC3B-R (SEQ ID NO: 27), ATG12-F (SEQ ID NO: 28), and ATG12-R (SEQ ID NO: 29).

Complementation assay. *Saccharomyces cerevisiae* BY4742 wild type strain (MATα; his3Δ1; leu2Δ0; lys2Δ0; ura3Δ0) and vma21Δ mutant (BY4742; Matα; his3Δ1; leu2Δ0; lys2Δ0; ura3Δ0; YGR105w::kanMX4) are obtained from the yeast deletion library (Euroscarf). The coding sequence for LOC203547 is cloned into a yeast expression plasmid pCADNS under expression of an alcohol dehydrogenase (ADH) promoter and terminator, and transformed into wild type BY4742 and vma21Δ mutant yeast strains. Transformation of yeast is carried out using a high efficiency transformation protocol, See, e.g. Gietz, R. D. et al., "Applications of high efficiency lithium acetate transformation of intact yeast cells using single-stranded nucleic acids as carrier," *Yeast* 7:253-263 (1991), the entire contents and disclosure of which are hereby incorporated by reference. Transformants are selected on synthetic complete media (SC) without leucine. The transformants are assayed for viability on medium containing 10 mM Cacl2, YPD pH 7.5 (alkaline conditions) and for their ability to grow on glycerol as the sole carbon source.

Subcellular fractionation. Cultured lymphoblasts and fibroblasts are washed twice with phosphate buffered saline and centrifuged at 600 g for 5' to remove the supernatant. Packed cell volume (PCV) is measured, and cells are suspended in three volumes of hypotonic buffer (10 mM HEPES, pH 7.8, 25 mM KCl and 1 mM EGTA). Cells are incubated at 4° C. for 10' to allow swelling and are further centrifuged at 600 g for 5'. The supernatant is aspired, and the new PCV is measured. Isotonic isolation buffer (10 mM HEPES, pH 7.8, 250 mM sucrose, 25 mM KCl, and 1 mM EGTA) equal to twice the PCV is added and homogenized using the dounce homogenizer. The homogenate is maintained at 4° C. and centrifuged at 1000 g for 10'. The thin lipid layer is removed by aspiration and the resulting post nuclear supernatant is transferred to a new tube. This fraction is the post-mitochondrial fraction (PMF). PMF is subjected to ultracentrifugation at 100,000 g for 60'. The pellet obtained is the microsomal fraction and the supernatant consists of cytosolic fraction. For isolation of fractions from skeletal muscle, tissues are sliced into fine pieces and washed three times using PBS. Thin slices are moved to a glass tube, and 3.5 ml of homogenization buffer is added per gram of tissue. Samples are homogenized using an electric homogenizer. 0.5 mL of isotonic extraction buffer is added, followed by centrifugation at 1000 g for 10' at 4° C., floating lipid layer is removed, and the resulting supernatant is centrifuged at 12,000 g for 15'. The thin lipid layer is aspirated, and the PMF is centrifuged at 100,000 g for 60' to obtain the membrane-rich microsome pellet and cytosolic fractions.

V-ATPase assays. Total protein may be measured using the Bradford assay and a BSA standard curve. Hydrolysis of ATP by V-ATPase may be measured by the bafilomycin A1 sensitive assay method. Microsomal pellets are thawed on ice and suspended in ATPase buffer (10 mM HEPES-Tris pH 7, 5 mM MgCl2, 50 mM KCl, 10 mM NaN3, 1 mM levamisole and 10 mM NaF, 0.7 µg/ml leupeptin, 0.7 µg/ml pepstatin A, 48.72 µg/L PMSF) to a protein concentration in a range of about 0.75 to 1.75 mg/ml. Each reaction mixture consists of about 1 mM ATP substrate, 3 µg of total protein samples, 5 µM valinomycin, 5 µM nigericin, 1 mM orthovanadate, 10 µg/mL oligomycin in ATPase buffer made to a final volume of 70 µL and incubated in the presence or absence of 10 nM bafilomycin for about 30' at 37° C. ATP hydrolysis is terminated by addition of 13% SDS and 100 mM EDTA. Control reactions are done in order to correct any non-enzymatic hydrolysis of ATP or orthophosphate contamination from any of the reagents by adding the stop solution prior to addition of ATP substrate. Color reaction is initiated by addition of Taussky-Shorr reagent (0.5% w/v ferrous sulphate, 0.5% (w/v) ammonium molybdate and 0.5M sulphuric acid). See, e.g. Taussky, H. H. et al., "A microcolorimetric method for the determination of inorganic phosphorus," *J Biol Chem* 202:675-685 (1953), the entire contents and disclosure of which is hereby incorporated by reference. The reaction is incubated for 20' at room temperature and inorganic phosphate is measured by absorbance in a spectrophotometer at 650 nm. Standard calibration curve is generated using inorganic phosphorous standards (0, 2.5, 5, 10, 25, 50, 100, 150 nmole Pi). Mean values and standard deviation may be calculated from three independent assay repeats done in triplicate.

Determination of lysosomal pH. Control and patient fibroblasts are seeded on 25 mm circular glass cover slips (Fisher Scientific) and grown to confluence in DMEM with 10% FBS (Wisent) at 37° C., 5% $CO_2$. At confluence, cells are washed twice with phosphate buffered saline and serum-starved by adding DMEM containing 2% FBS for 40'. Lysosomes are loaded overnight with 0.5 mg/mL dextran-coupled Oregon Green 514 (Molecular Probes) in DMEM supplemented with 10% FBS. Lysosomes are subsequently chased for 2 h in DMEM (10% FBS) and washed to remove any residual dextran adhering to the coverslip. Ratiometric fluorescence microscopy is performed using a Leica DMIRB microscope with a 100× (1.4 NA) oil immersion objective. Fluorescence images are acquired using a Hamamatsu C4742 CCD camera at excitation wavelengths of 440+/−10 nm and 490+/−10 nm. Image acquisition and analysis is performed using the software package MetaMorph (Universal Imaging). The regions of interest (ROI), representing late endosomes/lysosomes as resolved by light microscopy, are defined as areas above a certain fluorescence threshold in the 490 nm excitation channel. The mean intensity ratio between the 490 nm and 440 nm excitation channels is calculated for each ROI, and the mean ratio weighted by ROI size is then calculated for each imaged fibroblast. Calibration curves are obtained after 4' equilibration in nigericin (5 µm) containing MES buffers (in mM: 30 NaCl, 130 KCl, 30 MgCl2, 25 MES and 20 glucose) with different pH values adjusted between pH 3.0 to 7.0. Ratios are converted into pH values by using the calibration curve fitted to a sigmoidal equation. At least six lysosomes within the same cell are covered, and the experiment is repeated six times to obtain statistical significance.

Long-lived protein degradation. Total protein degradation in cultured cells is measured by pulse-chase experiments. Confluent cells are labeled with 2 µCi/ml [$^{35}$S]methionine/[$^{35}$S]cysteine Redivue™ in vitro cell labeling mix for 48 h at 37° C. and then extensively washed and maintained in complete medium with an excess of unlabeled methionine and leucine for 48 h. Aliquots of the medium and cells taken at different times are precipitated in trichloroacetic acid, and proteolysis is measured. Total radioactivity incorporated in cellular proteins is determined in triplicate samples as the amount of acid-precipitable radioactivity in labeled cells immediately after washing. Proteolysis is calculated as the % acid-precipitable radioactivity (protein) transformed into acid-soluble radioactivity (amino acids and peptides) at the different analyzed time points. Values are expressed as % protein degraded. In separate sets, the above proteolysis experiments are performed in the presence of 15 mM $NH_4Cl$ and 100 µM leupeptin or 10 mM 3-methyladenine in the culture medium during the chase. The former combination effectively blocks all types of autophagy, as it reduces the activity of all lysosomal proteases by increasing the lumenal lysosomal pH without affecting the activity of other intracellular proteolytic systems. See, e.g., Salvador, N. et al., "Import of a cytosolic protein into lysosomes by chaperone-mediated autophagy depends on its folding state," *J Biol Chem* 275:27447-27456 (2000), the entire contents and disclosure of which is hereby incorporated by reference. Blockage of macroautophagy is attained with the PI3K inhibitor 3-methyladenine. See, e.g., Massey, A. C. et al., "Consequences of the selective blockage of chaperone-mediated autophagy," *Proc Natl Acad Sci USA* 103:5805-5810 (2006), the entire contents and disclosure of which is hereby incorporated by reference. The inhibitory effect on the lysosomal system is calculated as the decrease in protein degradation sensitive to $NH_4Cl$, while the inhibitory effect on macroautophagy is determined as the decrease in protein degradation sensitive to $NH_4Cl$ that is also inhibited by 3-methyladenine. Non-macroautophagy-dependent degradation is calculated as the percentage of protein degradation sensitive to $NH_4Cl$ that is not inhibited by 3-methyladenine.

Electron microscopy. Muscle biopsies minced into $mm^3$ pieces or fibroblasts and lymphoblasts cultured from patients and normal individuals are fixed in 2.5% glutaraldehyde in 0.1M phosphate buffer pH 7.4 for 2 hours. Following a thorough rinse in buffer, the samples are postfixed in 2% OsO4, dehydrated in acetone and infiltrated, embedded and polymerized in Embed 812-Araldite. Ultrathin sections are cut, mounted on grids, and stained in 2% Uranyl Acetate and Reynold's Lead Citrate. Specimens are then examined in a JEOL JEM 1230 transmission electron microscope (JEOL USA, Peabody Mass.) and photographed using a CCD camera (AMT corp., Danvers, Mass.).

Immunogold electron microscopy. Cells are fixed with 4% paraformaldehyde containing 0.1% glutaraldehyde in 0.1M phosphate buffer pH7.4 for 2-4 hours. Following a thorough rinse in phosphate buffer, cells are embedded in gelatin prior to being infused with 2.3M sucrose overnight. Cells are then mounted on aluminum cryo ultramicrotomy pins, frozen by immersion in liquid nitrogen and ultrathin cryosections prepared in a cryo ultramicrotome. Sections are transferred to a formvar coated nickel grids in loop of molten sucrose. Sections are immunogold labeled with antibodies against subunit a or subunit E of the V-ATPase or against the myc epitope. All the grids are first rinsed with PBS containing 0.5% BSA and 0.15% glycine and subsequently rinsed thoroughly with PBS BSA. They are then incubated in the appropriate primary antibody for 1 hour and again rinsed thoroughly with PBS BSA. Samples are then incubated in either goat anti-rabbit (a and E subunits) or goat anti-mouse (myc) 10 nm gold complexes for an additional 1 hour. Specimens are then washed in PBS followed by distilled water and stabilized in a thin film of methyl cellulose containing 0.2% uranyl acetate. Specimens are then examined in the electron microscope and photographed using a CCD camera. Particle density determinations are done using an image analysis program (Image J, NIH, Bethesda Md.). Particles per linear μm of membrane are determined from a minimum of 150 neutrophils from three controls and two patients. In addition, cytoplasmic density determinations are done and expressed as particles per $μm^2$. Data is expressed as a mean and standard error, and a student's t-test is used to determine significance.

Reagents, media, and antibodies. Bafilomycin A1, 3-methyl adenine, oligomycin, nigericin, levamisole, leupeptin ampicillin and G418-kanamycin sulphate are purchased from Sigma chemicals. [$^{35}$S]methionine/[$^{35}$S]cysteine Redivue™ in vitro cell labeling mix is from Amersham Biosciences. Synthetic complete drop out media (SC), yeast peptone dextrose agar (YPD), luria bertani media (LB) are purchased from BD biosciences, USA. Tissue culture media and reagents such as Dulbecco's modified eagle media (DMEM), alpha modified eagle media (α-MEM), lipofectamine, fetal bovine serum (FBS), trypsin, phosphate buffered saline, and Hank's balanced salt solution are purchased from Wisent biosceinces, Canada. Anti-chicken vacuolar ATPase subunit E antibody is purchased from Genway scientific (USA) and recognizes 31 kD V1 subunit E. V-ATPase V0 anti-rabbit subunit a1 is bought from Synaptic systems (Germany) and is used to probe 116 kD V0 subunit a. Rabbit anti-a3 is generated internally (Morris Manolson). Goat anti-calnexin, goat anti-ERGIC53, mouse anti-GAPDH, rabbit-anti COPI (beta-COP), COPII, GGA1, and mouse antiGM130 are purchased from Abcam Inc, USA. Rabbit anti-cathepsin D and hexosaminidase-B are kindly provided by Dr. Don Mahuran, Department of Genetics and Genomic biology, Hospital for Sick Children, Toronto, Canada. Rabbit LC3B antibody is purchased from Novus biologicals, USA. Anti-Mouse Lamp1 and Lamp2 antibodies are also bought from Abcam. PstI antibody is a generous gift from Dr. Richard A. Rachubinski, Department of Cell biology, University of Alberta, Edmonton, Canada.

Figure 9:
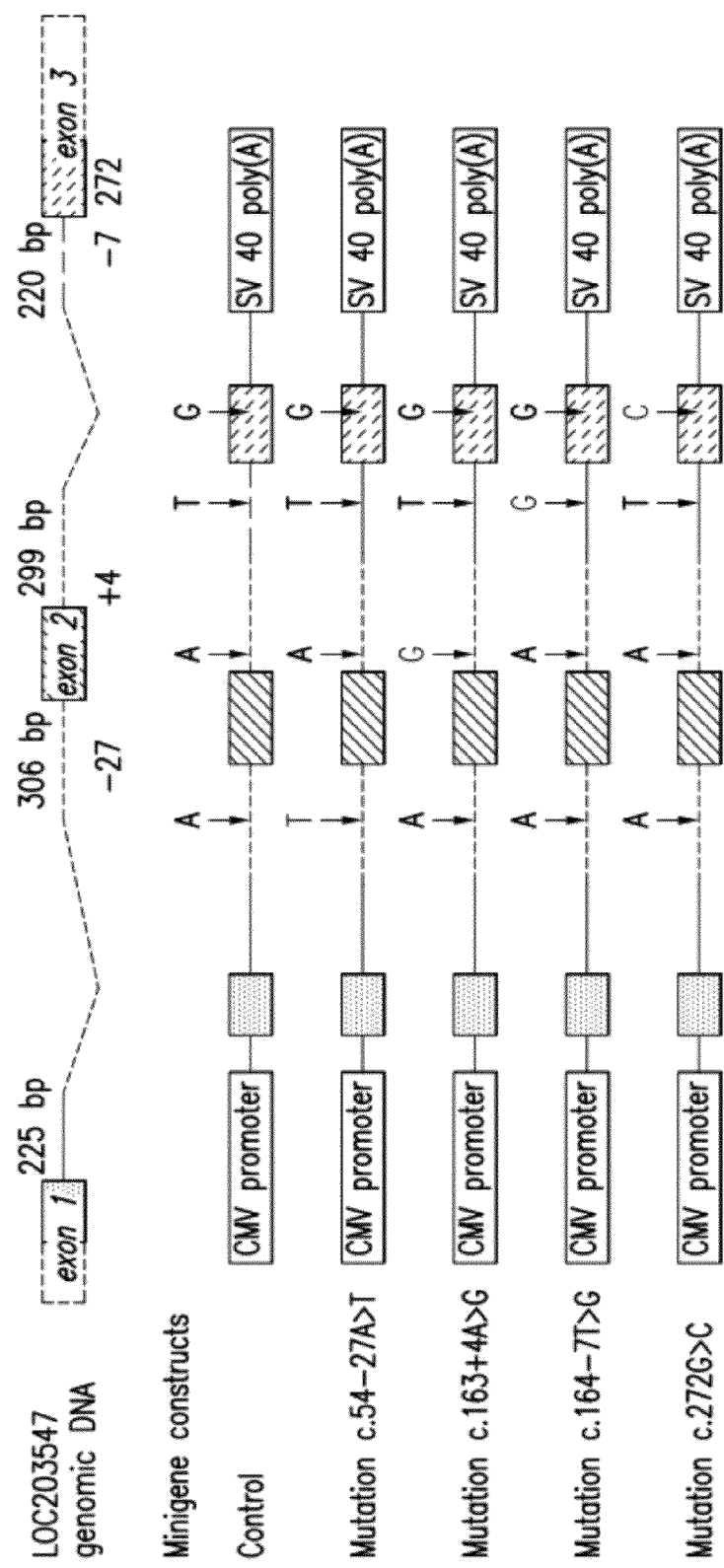
FIG. 9 is a diagram showing structure of minigene constructs with indications of mattions in pBluescript II-SK (+/−) (Stratagene)

Plasmids and constructs. Minigenes are constructed from control genomic DNA by amplifying three fragments of LOC203547 as follows: the last 60 nucleotides of exon 1 and first 225 nucleotides of intron 1, the last 306 nucleotides of intron 1, exon 2 and first 299 nucleotides of intron 2, the last 220 nucleotides of intron 2 and the first 120 nucleotides of exon 3 (FIGS. 9 and 18). From patient genomic DNA, either the second or third fragment is amplified to include the respective patient mutation. Primers in FIG. 18 used for the minigene constructs include: FI-HindIII-F (SEQ ID NO: 30), FI-XbaI-SalI-R (SEQ ID NO: 31), FII-SalI-F (SEQ ID NO: 32), FII-XbaI-BglII-R (SEQ ID NO: 33), FIII-BglII-F (SEQ ID NO: 34), and FIII-XbaI-R (SEQ ID NO: 35). All amplified fragments are sequenced and cloned in fragment 1-fragment 2-fragment 3 succession between the HindIII and XbaI sites of the pBluescript II-SK (+/−) vector (Stratagene), previously modified to include the CMV promoter and the SV40 poly(A) tail. 0.5 μg DNA of a PRDM8 gene construct is co-transfected as a transfection efficiency control. Cells are harvested 48 h post-transfection without any selection. All transfections are performed in triplicate for each construct. For immunofluorescence studies, a C-terminal myc-tagged VMA21 construct is generated by PCR amplification of full-length cDNA with KpnI (5') and XbaI (3') restriction sites attached and subsequent cloning in-frame with the myc tag (EQKLISEEDL (SEQ ID NO: 40)) into pcDNA3.1 version A vector (Invitrogen). Primers in FIG. 18 used for the myc-tagged constructs include: KpnI-VMA21-F (SEQ ID NO: 36) and XbaI-VMA21-R (SEQ ID NO: 37). To study functional complementation of LOC203547 in yeast, the pcADNS plasmid is used. This is a yeast expression plasmid that contains ADH promoter and terminator, leucine biosynthesis (LEU2) auxotrophic marker for selection and ampicillin resistance. Plasmids VMA21-myc and pcADNS are digested with KpnI and XbaL LOC203547 flanked with KpnI and XbaI sites is ligated into compatible sites (KpnI/XbaI) in the multiple cloning site of pCADNS to generate pcADNS-LOC203547.

Northern blotting. The Human 12 lane MTN blot (Clontech) is hybridized with a [$^{32}$P]dCTP-labeled 598-nucleotide fragment amplified from LOC203547 3'UTR, according to manufacturer's instructions. The blot is then stripped and controlled for RNA loading using the β-actin cDNA probe provided by the manufacturer. Primers in FIG. 18 used for amplification include: LOC203547-North-F (SEQ ID NO: 38) and LOC203547-North-R (SEQ ID NO: 39).

Cell culture and transfections. Lymphoblasts are cultured in RPMI media, and fibroblasts in DMEM supplemented with 10% fetal bovine serum (FBS), 100 U/ml penicillin, and 100 µg/ml streptomycin. C2C12 myoblasts are maintained in Dulbecco's modified Eagle's medium (DMEM) supplemented with 15% foetal calf serum (FCS) and antibiotics (penicillin 100 IU ml$^{-1}$, streptomycin 100 µg/mL) in 5% $CO_2$ at 37° C. under a humidified atmosphere of 5% $CO_2$ in air and maintained at low confluence. Transfection of C2C12 myoblasts is performed using Lipofectamine 2000 transfection reagent (Invitrogen, UK), according to the manufacturer's protocol. For minigene experiments, 0.5 µg of minigenes are transiently transfected in C2C12 myoblast cells, and 0.5 µg DNA of PRDM8 gene construct is co-transfected as a transfection efficiency control. Cells are harvested 48 h post-transfection without any selection. All transfections are performed in triplicate for each construct. Cells are incubated for 24-48 hours for RNA extractions and 48-96 hours for protein experiments. For immunoflourescence, Cos7 fibroblasts are grown in chamber slides in DMEM with 10% FBS and transfected with 0.5 µg of VMA21-myc DNA using lipofectamine according to the manufacturer's protocol.

Western blot analyses. Protein samples are mixed with an SDS sample buffer, boiled at 95° C. for 5 min, and subjected to the SDS-PAGE and Western blot procedure. Proteins are transferred on to nitrocellulose membranes using a semi-dry blot. Membranes are blocked using 4% skim milk powder in PBS-tween. Primary antibodies are added for an hour. After washing for 3 times, each lasting 10 minutes, blots are treated with corresponding horseradish peroxidase-linked secondary antibody. After three 10 minute wash steps, the regions of antibody binding are detected with the enhanced chemiluminescence method (SuperSignal kit; Pierce). Immunoblots are quantified using densitometric analysis (Multi-Analyst; Bio-Rad). For all western blots, loading controls are used and where required, verification of the purity of the cytosolic and membrane fractions is assessed using antibodies against cytosol and membrane-specific proteins.

Immunofluorescence. Cos7 cells are cultured on microscope slides in dulbecco's modified eagle medium with 10% foetal bovine serum and transfected with pcDNA3.1-VMA21-myc construct using lipofectamine (Invitrogen). Cells are fixed with 1:1 methanol-acetone for 15 mins at −20° C. and blocked with 10% bovine serum albumin in phosphate buffered saline for an hour. Following this, the cells are labeled with primary antibody and, after three 5 minute washes, treated with corresponding fluorescent secondary antibodies. Following three 5 minute PBS-tween washes, slides are fixed and viewed using Zeiss spinning disc confocal microscope with red and green filters suitable for red and green fluorescence. Images are quantified for co-localization using the volocity quantification software.

Example Discussion

XMEA is the first multi-mutation genetic disease known by applicants where all but one mutation are in untranslated regions. Each of the identified mutations is a hypomorphic allele that reduces the mRNA quantity of the VMA21 gene, in most cases by decreasing splicing efficiency. Only skeletal muscle is clinically affected, and only in males. Female carriers are unaffected, likely because muscle is a syncytium and half the nuclei will produce normal amounts of VMA21 mRNA. VMA21 is shown to be the human orthologue of the yeast V-ATPase chaperone Vma21p, and reduced VMA21 mRNA is shown to result in misassembly of the V-ATPase, decreased numbers of V-ATPase complexes on organelles and plasma membrane, and reduced total cellular V-ATPase activity to 10-30% of normal.

Several other genetic diseases affecting V-ATPases have been described previously. In all these diseases mutations affect specific V-ATPases in particular cellular locations, and practically all these mutations result in complete loss of function of the particular V-ATPase. For example, mutations in the gene encoding the a2 isoform of "subunit a" affect certain Golgi and early endosome V-ATPases in certain tissues, but not lysosomal or other V-ATPases (causing Debré developmental delay with wrinkled skin syndrome). Mutations in the a3 isoform affect only V-ATPases on osteoclast plasma membranes (causing osteopetrosis). Mutations in the a4 isoform affect only renal and inner ear plasma membrane V-ATPases (causing renal tubular acidosis and deafness). XMEA is the first disease affecting a V-ATPase in which total, not local, cellular V-ATPase activity is affected. On the other hand, XMEA mutations do not completely eliminate the V-ATPase activities. XMEA patients do not exhibit neurodevelopmental delay or clinically manifest skin and bone abnormalities, acidosis, or hearing loss, indicating that the reduced V-ATPase assembly in XMEA is not to a clinical extent for the a2, a3, and a4 containing V-ATPases.

The reduced V-ATPase activity in XMEA results in a rise in lysosomal pH from 4.7 to 5.2. Maturation of two lysosomal enzymes tested is not affected by the pH alterations, though their final activities are expected to be lowered. Hexosaminidase, for example, is known to be 50% less active at pH 5.2 than at pH 4.7. Not surprisingly, this degree of hexosaminidase downregulation is tolerated by XMEA patients. Like carriers of Tay-Sachs disease who also have 50% reduction in this enzyme, they do not have symptoms of hexosaminidase deficiency. Other individual lysosomal enzymes are likely similarly subclinically downregulated. Remarkably, it appears that the individual lysosomal enzyme functions are mostly taking place within the autolysosomes, as in most cells the number of normal-sized lysosomes is drastically reduced.

Figure 16F:
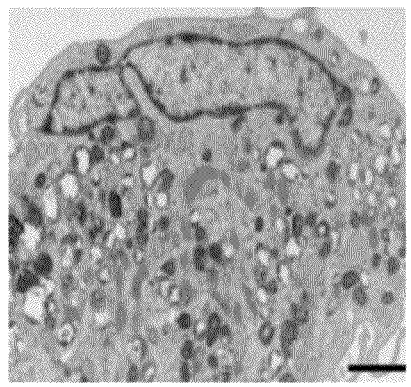
FIG. 16F is a higher power view of the image in FIG. 16E (bar=0.5 µm)

Autophagy, the collective activity of lysosomal enzymes involved in the degradation of long-lived proteins, is also reduced. But there is, at the same time, upregulation of macroautophagy and a dramatic increase in autolysosomes, apparently compensating with numbers for decreased autophagic effectiveness. A 50% rate of autophagy is achieved with which 95% of cells remain healthy, maintaining normal growth and replication and showing no morphological abnormalities, other than the increased autolysosomes. However, importantly, some of the cells (about 5%) do exhibit giant autophagic vacuolation, the hallmark of XMEA. This suggests that there is continuity between the compensated state of controlled-increased effective macroautophagy and the pathologic state of profuse giant autophagic vacuolation, that XMEA cells are precariously close to the transition between these two states, and that about 10% V-ATPase activity is the threshold for this transition. We found evidence supporting the 10% threshold in studies of the specific V-ATPase inhibitor bafilomycin. See, e.g., Bowman, E. J. et al., "Bafilomycins: a class of inhibitors of membrane ATPases from microorganisms, animal cells, and plant cells," *Proc Natl Acad Sci USA* 85:7972-7976 (1988), the entire contents and disclosure of which is hereby incorporated by reference. Shacka and colleagues incubated cells with 0.3 and 10 nM bafilomycin for 24 hours and at 10 nM found cells with 'accumulation of large, swollen, single-membraned vacuoles in the cytoplasm with electron-dense deposits', which were not present at 0.3 nM. See, e.g. Shacka, J. J. et al., "Bafilomycin A1 inhibits chloroquine-induced death of cerebellar granule neurons," *Mol Pharmacol* 69:1125-1136 (2006), the entire contents and disclosure of which is hereby incorporated by reference. These vacuoles appear morphologically identical to XMEA giant autophagic vacuoles. In reviewing earlier bafilomycin dose-response curves, it is found that 0.3 nM bafilomycin reduces V-ATPase activity to 40-50% of normal, and that 10 nM bafilomycin reduces it to just below 10%. See, e.g., Drose, S. et al., "Bafilomycins and concanamycins as inhibitors of V-ATPases and P-ATPases," *J Exp Biol* 200:1-8 (1997); Drose, S. et al., "Inhibitory effect of modified bafilomycins and concanamycins on P- and V-type adenosinetriphosphatases," *Biochemistry* 32:3902-3906 (1993), the entire contents and disclosures of which are hereby incorporated by reference. Taken together, these results indicate that, whether genetically or chemically mediated, reduction of V-ATPase activity to 10% sets in motion an autophagic vacuolar transformation, and that a variety of cells respond in the same manner (e.g. fibroblasts (FIG. 16F), lymphoblasts, leukocytes and platelets (not shown), and in the Shacka et al. study, cerebellar granule cells).

Three questions are key to understanding the pathogenesis of XMEA: What process is instigated by 10% or less and not by higher V-ATPase activities to drive the autophagic vacuolation? What are the mechanisms of the vacuolation? And why does skeletal muscle have such a high percentage of its cells vacuolated, even though its V-ATPase activity is not less than in other cell types?

One possibility is that the giant vacuoles are the fate ultimately of every XMEA cell. If the cells are managing to clear most but not all unwanted macromolecules, the excess could slowly build up over time in the autolysosomes, which might merge and become the giant debris filled vacuoles. However, a 'passive' mechanism such as this is unlikely, because one would expect to see a continuum of cells with different size vacuoles instead of a strict distinction between cells with numerous normal-sized autolysosomes versus cells with giant vacuoles. Furthermore, in the Shacka et al. study, vacuolation happened within 24 hours, hardly sufficient time for enough unwanted macromolecules to accumulate to fill up vacuoles that practically occupy the majority of the cytoplasm.

Instead, it is proposed that an 'active' process may be at play. While precariously hanging on the compensated side, if a cell drifts across the threshold towards no longer managing the defect, a switch may occur from controlled increased macroautophagy to an all out aggressive self-elimination by autophagic vacuolation and autophagic cell death. The investigators who originally described XMEA predicted such an active 'excessive' autophagy when they saw the profusion of giant vacuoles, many pouring myofiber cytoplasm out of the cell. A parallel to this 'tipping into explosive macroautophagy' concept is further found in bafilomycin work. Yamamoto et al. briefly (one hour) treated starved and non-starved cells with or without high-dose bafilomycin (100 nM bafilomycin, which completely eliminates V-ATPase activity). This brief treatment had no significant effect on non-starved cells. Starved cells without bafilomycin exhibited the expected increased controlled macroautophagy, but starved cells with bafilomycin showed explosive autophagosome formations occupying vast portions of the cytoplasm. See, e.g. Yamamoto, A. et al., "Bafilomycin A1 prevents maturation of autophagic vacuoles by inhibiting fusion between autophagosomes and lysosomes in rat hepatoma cell line, H-4-II-E cells," *Cell Struct Funct* 23:33-42 (1998), the entire contents and disclosure of which is hereby incorporated by reference. This result shows that during a state of increased macroautophagy (starvation in this case), inactivating the lysosomal component of macroautophagy switches macroautophagy into explosive expansion.

In XMEA cells, the majority of lysosomes are occupied as autolysosomes. It is possible that in those cells in which all lysosomes are thus occupied, when further autophagosomes form they find no lysosome partners. In effect, a state of complete elimination of the lysosomal component of macroautophagy results, which drives them into massive uncontrolled expansion, absorbing large sections of cytoplasm and becoming giant autophagic vacuoles. Interestingly, in XMEA skeletal muscle, the relatively smaller of the giant autophagic vacuoles are devoid of lysosomal enzymes, while the larger ones do contain lysosomal enzymes (FIG. 1H), indicating that the initial formation of vacuoles occurs with no lysosomal participation. It is likely that the expanding giant vacuole later acquires lysosomal enzymes by absorbing lysosomes and autolysosomes in its path. Of all tissues, skeletal muscle has the highest macroautophagic activity. Yet, unexpectedly, it has the fewest lysosomes (although they are more than sufficient in the physiologic state). See, e.g., Bechet, D. et al., "Lysosomal proteolysis in skeletal muscle," *Int J Biochem Cell Biol* 37:2098-2114 (2005). In the above scenario, skeletal muscle would be expected to be the organ most likely to undergo the greatest vacuolation.

The immediate consequences of significant reduction in autophagy are decreased recycling of defective and unneeded proteins and organelles leading to their accumulation, and deprivation of the cell from the amino acids and other constituents normally made available through this recycling. While cells may readily correct the deprivation through nutritional sources, relying on new, rather than recycled, building blocks would ever increase the accumulation of macromolecule content in these vacuoles, and the demands on the already critically strained autophagy would only further increase. Tissue responses to reduced autophagy may therefore include activating programs that may assist surviving on less with cells going into modes akin to what they would do in low nutritional states. Skeletal muscle is a particularly relevant tissue in this regard since it supplies amino acids to other tissues in low nutritional states. When in starvation mode, skeletal muscle undergoes a great activation of macroautophagy to support the rest of the organism. The fibers that are most involved in this self-sacrifice process are the type II fast-twitch fibers, which in XMEA are the fibers that show the greatest autophagic vacuolation. It is possible that heightened macroautophagic activation in muscle cells, which are already in a barely compensated state, tips large numbers of muscle cells into 'excessive autophagy' and autophagic vacuolation.

The drug chloroquine commonly prescribed for malaria and a host of autoimmune diseases accumulates in lysosomes, raises their pH, and impairs the degradation of long-lived proteins. As with any chemical agent, it has never been clear whether these or other unknown effects of chloroquine underlie the florid autophagic vacuolation it causes in skeletal muscle in some patients. Absence of the LAMP2 protein in Danon disease also causes autophagic vacuolation, but in both skeletal and cardiac muscle. Several functions have been attributed to LAMP2 including chaperone-mediated autophagy and lysosome biogenesis. See, e.g. Cuervo, A. M. et al., "A receptor for the selective uptake and degradation of proteins by lysosomes," *Science* 273:501-503 (1996); Cuervo, A. M. et al., "Unique properties of lamp2a compared to other lamp2 isoforms," *J Cell Sci* 113(Pt 24), 4441-4450 (2000); and Eskelinen, E. L. et al., "Role of LAMP-2 in lysosome biogenesis and autophagy," *Mol Biol Cell* 13:3355-3368

(2002). In addition, it has been shown that autophagosome maturation into autolysosomes and macroautophagy are partially impaired in this disease, possibly due to LAMP2 being necessary for the locomotion of lysosomes along microtubule tracts towards other organelles. See, e.g., Huynh, K. K. et al., "LAMP proteins are required for fusion of lysosomes with phagosomes," *Embo J* 26:313-324 (2007); and Tanaka, Y. et al., "Accumulation of autophagic vacuoles and cardiomyopathy in LAMP-2-deficient mice," *Nature* 406:902-906 (2000). Interestingly, the pathology of Danon disease differs somewhat from XMEA and chloroquine myopathy in that the autophagic vacuoles do not travel to the sarcolemma to extrude their contents, possibly due to lacking the LAMP2 motor for locomotion.

Looking at XMEA, chloroquine myopathy, and Danon disease collectively, the following common patterns are observed: In all three, the causative defect affects the lysosome in all tissues; there is no clinically significant dysfunction of any particular lysosomal enzyme in any tissue; there is partial impairment of autophagy in multiple different cell types and organs; there is autophagic vacuolation in a fraction of cells of many different cell types; there is autophagic vacuolation of most cells in muscle; and there is clinical disease only in muscle. Unraveling this pathobiological phenomenon awaits testing of hypotheses such as the ones invoked above and others in animal models for all three diseases.

Do the assembly processes directed by VMA21 in humans parallel those of Vma21p in yeast? In yeast, the c, c' and c" subunits composing the rotating cylinder of the $V_O$ sector of the V-ATPase are homologous proteins with 32-56% sequence identity, and assembly of the V-ATPase is initiated by Vma21p interacting with c', following which c, c" and then the other subunits are assembled. Subunits c and c" are conserved from yeast to man with exceptional ~70% identity, but subunit c' is altogether absent in humans. Humans therefore either use in place of c' a novel protein not resembling c' in sequence, or they simply do not need c' and can initiate assembly with c or c". The great divergence in sequence between yeast Vma21p and human VMA21 might support the first possibility and invoke the need for a human replacement for c'. However, our demonstration that VMA21 fully complements yeast vma21Δ shows that VMA21 can fully assemble the yeast V-ATPase using yeast proteins. Therefore, VMA21 in humans may likely initiate assembly with c and c" without the need for a c' substitute.

In yeast, Vma21p accompanies the nascent V-ATPase on COPII vesicles to the Golgi apparatus. At the Golgi, its separation from the complex may allow the addition of the $V_1$ components and completion of the complex, and Vma21p returns to the ER using its dilysine ER return signal for a new round of $V_O$ assembly. Human VMA21 also travels on COPII vesicles but goes only as far as the ERGIC. It does not have the dilysine ER return signal, nor is it found on the ER return COPI vesicles. The systems therefore appear to diverge between yeast and human. Where and how the $V_1$ components are added and the fate of VMA21 after it reaches the ERGIC are unknown. Possibly, VMA21 may simply drift back to the ER through the continuousness of the membranes of the ERGIC and ER.

A disease gene is identified herein. The assembly of one of the most complex machines in the cell, the V-ATPase, is shown to follow the same general plan in humans as in yeast, with important divergences to be explored. The clinical outcome at the cusp of tolerable elimination of V-ATPase activity is shown, and a model to allow understanding of the cellular events at the transitional state between demise of autophagy and autophagic demise of the cell is provided.

The development of cell lines from XMEA patients may serve as a resource to study each of the numerous functions of the V-ATPase, even if not disturbed to a clinical extent, across a range of low V-ATPase activities from about 10% to about 30%. Such resources may have ramifications on very common human diseases. For example, *Plasmidium falciparum*, the malaria parasite, encodes a V-ATPase which inserts into the red blood cell membrane and confers the cell the optimal pH for the parasite. See, e.g. Hayashi, M. et al., "Vacuolar H(+)-ATPase localized in plasma membranes of malaria parasite cells, *Plasmodium falciparum*, is involved in regional acidification of parasitized erythrocytes," *J Biol Chem* 275:34353-34358 (2000). Entry of a variety of viruses into human cells, including influenza virus to HIV, as well as toxins, such as diphtheria and anthrax, depend on V-ATPase activity. See, e.g. Forgac, M. et al. (2007), supra. Increased osteoclast activity, strictly dependent on the V-ATPase at the cell membrane of osteoclasts, underlies osteoporosis. See, e.g. Manolson, M. F. et al. (2003), supra. Neoplastic invasiveness and metastasis depend on the V-ATPase, which acidifies the extracellular field attacked by the tumor to allow hydrolases to open passages through the extracellular matrix. The more invasive a tumor, the more it possesses membrane V-ATPases, and inhibition of the V-ATPase diminishes the invasiveness of tumors. See, e.g., Sennoune, S. R. et al., "Vacuolar H+-ATPase in human breast cancer cells with distinct metastatic potential: distribution and functional activity," *Am J Physiol Cell Physiol* 286:C1443-1452 (2004). In XMEA patients, it is shown herein that the safety margin of reducing V-ATPase activity in humans is wide, increasing the therapeutic potential of bafilomycin-related compounds in all the above diseases. V-ATPase activity can be regulated through VMA21, opening the possibility of adding more specific genetic approaches (RNAi against VMA21) to less specific chemical methods of regulating V-ATPase activity to influence the course of common human diseases.

While the present invention has been disclosed with references to certain embodiments, numerous modification, alterations, and changes to the described embodiments are possible without departing from the sphere and scope of the present invention, as defined in the appended claims. Accordingly, it is intended that the present invention not be limited to the described embodiments, but that it has the full scope defined by the language of the following claims, and equivalents thereof.

What is claimed is:

1. A method comprising
   a) Preparing an isolated DNA preparation from a sample taken from an individual;
   b) Amplifying a DNA fragment of interest from the DNA preparation with a pair of isolated DNA oligonucleotide primers selected from the group consisting of SEQ ID NO: 14, SEQ ID NO: 15, SEQ ID NO: 16, SEQ ID NO: 17, SEQ ID NO: 18 and SEQ ID NO: 19;
   c) determining from the amplified DNA fragment whether the individual has the following mutations in the VMA21 gene or locus: c.54-27A>T; c.54-27A>C; and c.163+4A>G; and
   d) diagnosing the individual as having or being at risk of developing X-linked myopathy with excessive autophagy (XMEA) and/or diagnosing the individual as being a carrier of at least one mutation if the individual is determined to have at least one of the mutations.

2. The method of claim 1, wherein the DNA fragment of interest is amplified by PCR.

3. The method of claim 1, wherein the DNA fragment is further analyzed for one or more of the following mutations in the VMA21 gene or locus: c.164-7T>G; c.164-6T>G; c.272G>C; and c.*6A>G.

* * * * *

SEQUENCE LISTING

<160> NUMBER OF SEQ ID NOS: 45

<210> SEQ ID NO 1
<211> LENGTH: 12798
<212> TYPE: DNA
<213> ORGANISM: Homo sapiens

<400> SEQUENCE: 1

```
gggtcactgg catcgagtct ggaacagtca ttctcagcaa gagctctttg aactctgaca    60
ttctctagtt ttacggactc gggtgagtgt tttaactcct cccagctgcc aagggcttga   120
cttcctacca ctgcgggcag taattaatga ggcatttatt tgctcaagta gtggcgaaat   180
aatgcgcact gcttttttgt gttgtcgtcg gcggaatacg ctcagttgcc tagcaccaca   240
gccctctggc tggtagtccc tcttcgcggc tcatatgctc gggtctcctt gcggccccca   300
gctcagcgac cgagacgcag acgaggacca gtgttcacgc gagttcaggg ggcggcgtag   360
ccgccgcccg cccaggagga ccatgttgcg cggcaagtcc cggctcaacg tggagtggct   420
gggctactcg ccaggcctgc tcctcgagca caggcccctc ctggcagggc cacgccgcg    480
gagccaccgc cggtaagtca tgtgagcgcc cgccccgcg ccggcaacag ccctgcgtcg    540
ctgcggcgcg ccgcgccgcg ccgcgcctgc gtactgtggc ccgccgcccg gcgcgaacgg   600
gcacttccgg cgcgaacggg cacttccggc gcgaaccgct acttccggtg cgaaccgcct   660
cggccgttcc ctcgcggagc ttactgagcg cggccgccga gcccagctcc gccgccgagc   720
gcctgtgccg gcacggctac accatggagc gcccggataa ggcggcgctg aacgcactgc   780
agcctcctga gttcaggtag ccctgagcgg ggcctggacc gcgaggcgga ctggccccag   840
cctggagcag ggcttgaggg aaggcccctag ctgaatgggt gggcgtgagg tctgacccc   900
ggggacctgg cctcagggaa gggggcgggg aaagcaggtt ggagcctgag acgtctaaac   960
tcccggcccc gaactttcgc tcgggaacaa gggatccggg gtcatgggga ataggtcagt  1020
gggccttcag ctcatgctcc tatcctagca ctttctctcg ctgtgtctat attgcagtct  1080
ctttcattac cgcagggtca gccttctgag gacaggaatg cagtctcctt catctccgtg  1140
ttccctaggg ggcctgcata gtcggggctt aataaatgtt tgctgtatga atgaaggagt  1200
agaagggaat agtcccctgg tgtgagattg cttcacttgg ggaatcagta agatagaggc  1260
tggtgactga gttgaaggaa tgtatgagag agcaggtggt tctggcccac cccagtaggc  1320
aagggagtgg tgagggagtt agctatcatt cgttaagacc tactgtatgc caggctcagt  1380
gcacgtgctt tacatacatt gtcagaattc ttaatttctc taactgcttg atttcccaat  1440
tttgaagagg atgcagttga gggtaagtga cttgaaactg agggtgagtg attacagaat  1500
taggcgacaa agttagtatg taattgaagc taacgtttga ccaagctcac tgactccaaa  1560
gcccacgatc tttggagctc tgtgatgcct tctctttccg acagggtcat tgtgagtttt  1620
tttttttttt ttttaacttt tattttaggt tcatgagtac atgcgcaggt tgttatata   1680
ggtaaactgc atgtcacggg ggcttggcgt acaggtaatt ttgtcaccca ggtaataagc  1740
atagtacccg ataggcgttt tttctgattc tctccctcct cccagcctcc accctcaagt  1800
agaccgcact gtctgttgtt cctctcctag tgtccatctg ttcttgttgt ttagttccca  1860
cttatgagaa cgtgcagtat ttggttttct tttcctgtct taatttgctt agaataatgg  1920
cttccagctc cagtcatgtt gctgcaaagg acatgatctc attctttttt atggctgcat  1980
agtgttccat ggtgtatatg taccgcattt tctttatcca gcctcaatgt gggtttttt   2040
ttaattattc atttatgaga ataccaacat atttttatta gatacactta cagcatagtc  2100
cttctagact gattctggtt tcctaatgga atttgcagtg aaatcttgac tgtgggagaa  2160
agaattcctg ttgtcttact tgctacaaaa gggaatgtgg taggctctgt ctgctcaatg  2220
ttggctgcag aagtttgtat gaagtgggaa aactaggtgg tgttataaat ggaggcagat  2280
taaggttcat cctgaacttt ttcctttgtg tgaggacaac tttaattcca gcctttctca  2340
```

```
ttcctcactt ctaacaaatc tctgctcagt aacacccaaa gatacatagg ataaatcaat    2400
tgaatagcat cagttgcttt gtcttggata agccactgat tttacccaag gtggcttgca    2460
tcagcaaaac caacagctct tgtggctgga atccagggag aaaatgtcct ataaacagta    2520
gaggaagttt gctagttttc aaaagttgt atgtacactt tgacttaatg cttagtccca     2580
tattagtgag gtcacaacac agaaaagtag tcacattttt gaagtttgag gtaaagagag    2640
aagtgagaag gaattagcca taaattatta aggtatgctg tgtatagatt gtgtgggggc    2700
tagaaattaa tatgtagaaa ggttatattt gggtggtggg attataggtg attttgttta    2760
ctttaaaaca ttttatggt gttatatcat cttttcaata ataactttt taaaagccag      2820 accagataat agatactcaa gagaggtcat gtaaagaaca aaacaatcag ttaacacttc    2880
ctttctgttc cttaacaag ttagataatc tgaaagttgc attcctaaaa catacttttt     2940
tactcaccat agaaacacca aagtcaagtg ctttttttag ggtgcacaaa agaattggcc    3000
aattagtgac tctttgtatt ttttgtagat tctccactgc agacactcat actcttcatg    3060
aggattacac aataaatttc tctaaaaatt tactagtagg aaacagttta agggagctta    3120
tgtatattaa atgagagttg tatagctcag taataaccaa aatgaggcct gctaaaagat    3180
gatccattta agtaccaaaa gaaaatatta gaactttttt ttttacagca gtaagcattt    3240
aatttctcac acatgtgcag agcatgtgat caagaaatag gcatgaggtt agttatattt    3300
aatatatatt ttactcaatg tttttgtggg tttttttgttc aggttctttt taaataaatt   3360
tcattgtgta tatttgaggt tcataacatg atgttatggc atacatatag taaaatgatt    3420
actatggtga agcagattaa tatatctgtc atctcacata cttttgtgtg tgtgtgacca    3480
gaggcagcta aaatcttatt tacaaaagtc cctaatacca tgcaacttta ttgcctatag    3540
tcctcttgta cattagatat ctcacttgtt aatccatata tctactgctt tgtgtccttt    3600
gatgtatatc ttcctatttc ctcccctcca gcctcccacc cccaccgcca tggtaactac    3660
tgttttattc tctgtccctg tgtagttgac cgttgacctt ttttttttt ttttaaagat     3720 tccacatata agtgagctca tgtagtattc gtctttctgc gtttggctta ttttacttaa    3780
catgtcttcc aggtccatcc atgttgtggc aaatggcaga tgtcctcttt taaggctgaa    3840
taaaatattc ccttgtatat atacactacg gtttctttat tttgtctgtc tacatacacg    3900
taggttgttt tcaaatcttg gctattgtga ataatgctgc aatgaacatg gaagtgcaga    3960 tattttacg aggtagtgat ttcatctcct ttgcttatat tccagaagag agattgctgg     4020
gctgtgtggt agttctattt ttaatttctt taggaactgt tttccataat ggctgtacca    4080
gtctacattt ccagtcacaa tgtagtaggg tttctttttc tccacacttt tacaaacatt    4140
tgttatcact tgccttttg ataatagctg tccttagaag tgtgaggtta tatctcatag     4200
tggttttgat ttgcatttcc ctgatgattt agtgatgttg agcacatttt catttatctc    4260
ttggccattt ttatgtcttt ggagaaatgt ctgtccagct gttgtccata ttttaatcag    4320 gtggttttc tgctgagttg taagagttct ttataaattt tggggtatta accccttaca     4380
agataggtgg ttcgcaaata tgttttccta gtctgtaagc tgccttttca ttttgttgat    4440
tgtttccttt gcagtacaga agctttttag tttgatgcaa gccgctttat ttttctcttt    4500
gtagcctgag cttttggtgt gatatccaaa aaatcattac tgaggccaat gttaaggacc    4560
tttccctctg tgttcttta tgtcttaaaa ctttatatct ttatgtttta gttattttat     4620 ccatttggg ttgattttg tttatggtgt aagagtccag tttttttctt tgcatgtaga     4680
aatcctgttt tcccagtacc acttattgaa gggactgtcc tttccccatt gtgttcctct    4740
```

```
taacacccct gtcgaagatt agttggccat atatgtttgg atttatttct gggctctatt      4800
ctgtttcatt gttatatgtt tctgttttta tgccaatacc atattgtttt gattactata      4860
actgtaatat tttaaatcag aaagtgtgat gcttacaact ttttcaatgt tgctttggct      4920
atttggggct ttttgtggtt ctgtatgatg aattttagga ttgttttcct attttaatga      4980
agaatgctac tgtaattttg atagagattg tgttatatct gtatgttgct ttgggtgctg      5040
tagacatttc aacagtatta attcttccaa tccatgaaca caggatatct ttacatttat      5100
ttgtgtcatc ttcaatttct ttcatcagtg ttttatactt ttcagtgtac aagtcactca      5160
tcgccttggt taaatttatt cctaagtttc tttttttttg aaatagagtc ttgctctgtc      5220
acccaggcca gagtaaagtg ccccaatcac tgctcactgc agccttgacc tctgggctc      5280 aaacaatcct cccacttcag cctcttgagt agctgagatt acaggcacgt gccaccatgc      5340
ccagcgaatt atcaaaattt ttttttgtag aggtgggggtt ttgctgtgtt acctaggctt      5400
gcgtcaaact cccggcctca agcctcagcc ttcccaaagt gctgggatta caggcatgag      5460
ccactgagcc tggcccctaa gtattttttt ttaatgctat tataaatgag attgttttct      5520 tgatttctttt ttcagctcag taaaggatgc ggaagtttgt caagtgcttt ttctgcatca      5580
actgagatga tcctacttgg tcataatata taatcttttt gatgtattgg ttttgtttgt      5640
ttgtgacaga gtcttgctct gttgcccaga ctggagtgtg attttggctc attgcaacct      5700
ctgcctccca ggatcaaggg attcttgtgc cttggcctcc caagtagctg ggactatagg      5760
cacacgccac cactctcagc taattttttgt attttttagta gagactgggt tttgccatgt      5820
tggccaggct gatctcgaac tcctggcctc aagtgatccg cctgcctcgg cctcccaaag      5880
tgctgggatt acaggtgtga gccaccacac ctggcctgat tattgttgaa tttggtttga      5940
aaatatgtta ttgaggaatt ttgcaccagt gttcatcagt gatgttgtcc tgtagttttc      6000
ttgctgtgtc tgtctggctt aggtatcaag gtgattggag cctcttaaaa cgtgtttgga      6060
agtattccct ctagctcgat ttttcaccca taacagaagt tcctattcca gctggggagg      6120
gcgcactggt ccgttcgccc tgcctacctc cttcagtggt ctggtgtctg gtgctggtgg      6180
tcagggttgc tgcacgggct cagggactgg tgtggcagtg gcttccctgg gccaaagctc      6240
tgatcccagt gggggagggc acgctggtgc gtcggctcca cctggttagt ttgctggtcc      6300
actgtctggt gctggaggac aggaggctgg cagctttccc agatgcaagc tccgattcca      6360
gcgggagagg gcacactgct ccacctgtgg tgcctgccga gttccctggt ctggtgtccg      6420
gtgctggtgg tcagggttgc tgcgtgggct cagggaccag tgtgacagtg gcttccctgg      6480
gcaaaagctc tgattccagt gtgggagggt gcacaggtgt gtctgcctcg ttagttccct      6540
ggtccactgt ctcatgctgg aggacagcaa gctggtcgct tcccgtgacg gaagctctga      6600
ttccagcaaa agagggcgcg ctgatccacc catggtgcct gctgcgttcc cagctctggt      6660
gtctggtgct ggtggacacg gttgccgcat gggttgggca ctggtgccgc tgtccgccgt      6720
ggcttccctg ggtaaaagct ccagttccag aggcaggggc actgagtttc ttcacttagt      6780
ttgttcaccc agcttgttgg cagttgatct gaggtgccct gacgcttcgt cttacactgg      6840
atatgaatga cagtccctaa aggtggtgta taatcttcat gttccagctc aagaaattcc      6900
cactacccac agctggttct ctaggatctt cggattacga gtccctgcct gtgatcttcc      6960
tcctgcatag catctcattt gtggatgttt atagtttcag ggacataaga gcgtttggat      7020
atgactgtgc aggttctgat tttctctttg tttactttat tccagaaatg aaagctcatt      7080
agcatctaca ctgaagacgc tcctgttctt cacagcttta atgatcactg ttcctattgg      7140
```

-continued

```
gttatatttc acaactaaat cttacatatt tgaaggtaat cttagaccca ttaaaacaag    7200
atgttttccc ccaatttaag attctgtgct tttatgacct ctttatatct ttaaactggg    7260
tattcttatt ttttcttgt ttagcttttc aaaaaatcat attgctcata atgagtcttt    7320
atgaaataac ttattgtttc agcttgacag ttttcctatg gttttctgtg aaatagcttg    7380
caaatccttt ctcttagtac cttttaaaga ataggggttg gctgacatgg gaggaggaat    7440 tttggggaa tggactttag tgtcagataa cggaaggaag agagaatgaa gtcccctttt     7500
tgatgttgaa atttttttt ttttttgag acagtttcac tcttgttgca caggctggag      7560
tgcaatggcg cgatctcggc tcaccgcaac ccccgcctcc catgttcaag cgattctcct    7620
gtctcagcct cctgagtatc tgggattaca ggcacccgcc actacacccg actgatttt     7680 ggtattttta gtagagacgg ggtttcgcca tgttggccag gctggtctcg aactcgtgac    7740
ctcaggtgat ccacccgcct cggcctccca gagtgctggg attacaagcg tgagccaccg   7800
cacccggcct gaagtcttta taattatggt tttgtttaaa acaatgtttg tttgtttgtt    7860
tgtttgtttt tgagacggag tctcgctcag tcacccaggc tggagtgcag tggtgcgatc    7920
tcggctcgcg tcaagctctg cctcccaggt tcacgccatt ctgctgcctc agcctcccga    7980
gtagctggga ctacaggcgc ctgccactac gcctggctaa ttttttttgt attttagta     8040 gagacggggt ttcacggtgc tagccaggat ggtttccatc tcctgacctc gtgatctgcc    8100
cgtcttggcc tcccaaagtg ctgggattac aggcgtgagc cactgcaccc ggccaacata    8160
atgttcttaa tatatagaag gtactcatat cttttagtga atactttatt cattaccacc    8220
caaaatatta cttttaatt gcctgactag ttaaataaat acatcataaa aattaggatg     8280
ctttgttttt tttttttgta ctttggtaaa ttttgcaata aaatggaaac tgttttttt     8340 ctcttgatag gcgcccttgg gatgtccaat agggacagct attttacgc tgctattgtt     8400 gcagtggtcg ccgtccatgt ggtgctggcc ctctttgtgt atgtggcctg gaatgaaggc    8460
tcacgacagt ggcgtgaagg caaacaggat taaagtgaac atcaccttt tatagcatta    8520 aattcatttt ttaaaatgat aaatgctgga gggggccatc tgatttgaat aaagttgaaa    8580
gaacatgtta aagtcagtct taaggagtca cgtttgagta tgtaaatttt gatctttcta   8640
atatgttggt ttgtatattc agttttaact gtatgaatct gatttgcaaa tgagaatttg    8700
gaaaagttag ttacaaagaa atatgttaat ttaattagac aatactctgg aaggaatttt    8760
atcttctttc aacaaaacat gttttatagt attctgactt acggttgctt ttgagtttta   8820
ctcatttgga tatattaaga tgcacacagt gaagcaaatt aaactccact ttacgctgga    8880
atgctttctt tagcatgaaa ataccaggtc cttggatttg ggattttaat ttcctatgga    8940
aagttgctta aattgtggac actggaatta atctgaatgt cactgaggaa tttcacatga    9000
agtgtaatcc ctagtcaata agaattatcc attacattat tttatgggaa aactaggcta    9060
aattacatcc attcaggtaa aaggaccta gcttactgaa ggatctaaag agcaaagcaa     9120
agatctcact actcaaacac tcagcctgct tccttcaagt cccccttgcag gccagctttg   9180 tgctttgcag accaactttt taatgagata ctttgcttcc tcattcaaca ttgaagctag    9240
gcttcaatta aaaggttcga ggaagctcca tttaaaattg tttttttac tatttttaa      9300 aattgtagtg tatatgatag gaatttgcat ttaaatatgt tcatttttgc atatgttagg    9360
agtggaaaca atctggaaaa cattttttt tcatccaaaa agtattctcc ttgggcatat     9420
ctgatggaaa aaaccttga ttttatttc gtatctttag tctgtgttct ttctagttat      9480
ttggtactaa ttatgtgcaa tctaaaaaca ctcccacaag tatttgtttt ttaattataa    9540
```

```
aatcatagta tatgttcttt gtagaaaact ggaaaaatac atattcaaac aggaaaaaaa    9600
atcaaaattc cccataatgt tgccatctaa aaataacctc tattttagtt gatatcccgt    9660
attcattttt gaaagccatt ccttaatgct agtttgatac acactaaaag tttagcttac    9720
aagttcaaat tctgccagct tttcctgaca gctatttgca ttttttttcag atgagtgatt   9780 attggccatt ttctttttct ttttctttat tttatttatt tatttttttg agacagagtt   9840
ttgctctgtt gcccaggctg gagtgcagtg gtgcaatctc ggctcactgc aacctctgcc    9900
tcctgggttc aagtgattct ccacctcagc ctcccaagta gctgggacta cggatgcctg    9960
ccaccacgcc tggctaattt ttttttgtat ttttttgtag agacggggtt tcaccatgtt   10020
gtccaggcta atcttgaact tgtgacctca ggtgatccac ccgcctcggc ctccgaaagt   10080
gctgggatta caggcgtgag ctaccacgcc cggccttatt gaccatttc taaataagca   10140 cattctatct ttattctctt aaaattcaaa ttttctgtta ctgataatcc taatactagg   10200
attcttgctt aagtatgtga aaccattacc gatttgttgt tcacatttat tttttatgtt   10260
gtgaaactgg actaaaggaa tagagggatg attagtcata aaagtcaaat agcatttgtg   10320
tttaactgtt gagaaaagtg aaagatcagt atgattatta tggaactgtt tttaattctt   10380
gcttaaagac tacaaatttt gtataatgac atttgagtct agggtagtat gtggtagatt   10440
tctagatggt ccctaattaa gaagtattgt tgtatttaga attgtccacc taatttcttt   10500
ttatataatg ccaaggtatt tcttgtgctt ttgggatctt atgctgtttg taaaatgtta   10560
ctgtccaatg ttggattatt gttttggttt caggcatttg ctgaataggt gatgatacat   10620
gggtattttt ctgcaagtat ttaaaccagg ggcatatgca aaggcagttg taatttcctc   10680
ttggaaaaag cgccaaatgt ttgaaggtta aaatcaaatg ctagggttga tatttaggct   10740
tataacaaaa taggcttgtt ttcaaagcag ttttttccta gagttttaac tgttaactca   10800
ctagtttgct gctgtttta actatgttaa ataacatatg gtatttggca aatagattta   10860
tttttcaaaa tgtctcacta gtttcctttt acacaatgta tatacttcaa gatgtatagaa  10920 aaggaaagct acagttgagc ccttatacat gttttaaggt agaaatatgt tccctattgt   10980
ttgaaaactg attgtaagaa taacctcagt taggagatat aacttgaagt gtcagtccaa   11040
actactgatt taaccctatt tacggtaaca cattaccttc ctcacctcct gtttggccct   11100
ggagaatgta gtccttttc tcatttgtgt tgagaaatga aaagtctgct gtagaatgta   11160
tctgatgtca ttagttcttc aaatggatac cattgtacat ataacagtag aatttggttt   11220
ggggttgtta gtgaaaaaa atttaaacct gccattaaaa atccccatgt ttcatggaaa   11280
tctaacagaa atacattgta ataattagaa cattttgttt tctttttct ttttttttt   11340 ttcgagacgg agtttgccc ttcttgccca ggctggagtg caagggcgca atctcggctc   11400
gctgcaacct ccgcctcccg ggttcaagca gttctcctgc ctcagccccc tgagtacctc   11460
agatgacagg tgcgtgccac cacacccggc taattttgt attttagta gagacggggt   11520 ttcaccatgt tagccaggct agtctcgaac tcctgacctc aggtgatcca cccgcctccg   11580
cctcccaaag tgctgggatt acaggtatca gccaccgtgc ctggcctaat aattggaaca   11640
ttttcatcat gaaaatgtca tcagctttgc caaaagaaac aaccaattga cttgtttggc   11700
gtttgttttc cattttcatg tcaattttat gtatacagtt agaatacccca aggagaccac   11760 taaaatcagt taaacaagta gggtatatac aaagaaagat gaaacccgaa agtacataaa   11820
aaggatttaa atccgatttt agatgtacct agtgtgtatt tcttatctct agacaagttc   11880
atgtttattg tttaatttat gcccaagtga agttgtaaac ttatggttca actctgacac   11940
```

```
agaatttgtc acttgtctga ggtcagtggc aggtttctct gctgtcaagc actctgtgtc   12000
acccaccaga ttagtataac tattaattca gactgtactc ctatgtttaa gataattttt   12060
acaagagctg gctgaagcag cacattagta acctgacaag atttcttttt ccctttttcag  12120 ggggaaaggg tcaccttaaa aataaattat tttcagggac tttgggaatc taatgataaa   12180
tattacacat aatctatgaa tagcttaatc ctttatatat tccttaaaat aggaattcct    12240
cgacatcact cctggccaca cttcccttgc ctgtgttgtt gctatgtgta tttgaaagta   12300
atatctgcat tccttttaag atgttctgta agtcatattt gtcagttata cagagtagtc   12360 ttcctttcc ccacgttcag tgtaatctca ctgaacagta ataatagcaa tagctaacaa    12420
catctgcaca gcaccttaca gtttgcaaag aacgttcaca cattctcatt tgagttttgc   12480
atagtgaacc tgttacgaga tgtctcttga cgtcgatgct aaaagtgtta gaatctttac   12540
atcactagag tcattgaata tgctgtagta ttgaatagtg ccctgactag ggggaggatt   12600 tgatgtgct gcatttcaag ccgtgtataa tcatcaaaat gggggggcttg agttctttag    12660 ctacttgaat ccgatttact tctgttaagt gatgcttttc taaccgtttt ctggatggat   12720
tttgtattca ctatattgta gcttgtaatt tgtataaatg taccatctga tgtcattaaa   12780
aaaagtgttt gtagtgct                                                  12798

<210> SEQ ID NO 2
<211> LENGTH: 129
<212> TYPE: DNA
<213> ORGANISM: Homo sapiens

<400> SEQUENCE: 2
tccctcgcgg agcttactga gcgcggccgc cgagcccagc tccgccgccg agcgcctgtg    60
ccggcacggc tacaccatgg agcgcccgga taaggcggcg ctgaacgcac tgcagcctcc   120
tgagttcag                                                           129

<210> SEQ ID NO 3
<211> LENGTH: 110
<212> TYPE: DNA
<213> ORGANISM: Homo sapiens

<400> SEQUENCE: 3
aaatgaaagc tcattagcat ctacactgaa gacgctcctg ttcttcacag ctttaatgat    60
cactgttcct attgggttat atttcacaac taaatcttac atatttgaag              110

<210> SEQ ID NO 4
<211> LENGTH: 4448
<212> TYPE: DNA
<213> ORGANISM: Homo sapiens

<400> SEQUENCE: 4
gcgcccttgg gatgtccaat agggacagct attttttacgc tgctattgtt gcagtggtcg    60
ccgtccatgt ggtgctggcc ctctttgtgt atgtggcctg gaatgaaggc tcacgacagt   120
ggcgtgaagg caaacaggat taaagtgaac atcaccttt tatagcatta aattcatttt    180
ttaaaatgat aaatgctgga gggggccatc tgatttgaat aaagttgaaa gaacatgtta   240
aagtcagtct taaggagtca cgtttgagta tgtaaatttt gatctttcta atatgttggt   300
ttgtatattc agttttaact gtatgaatct gatttgcaaa tgagaatttg gaaaagttag   360
ttacaaagaa atatgttaat ttaattagac aatactctgg aaggaatttt atcttctttc   420
aacaaaacat gttttatagt attctgactt acggttgctt ttgagttta ctcatttgga   480
```

```
tatattaaga tgcacacagt gaagcaaatt aaactccact ttacgctgga atgctttctt    540
tagcatgaaa ataccaggtc cttggatttg ggattttaat ttcctatgga aagttgctta    600
aattgtggac actggaatta atctgaatgt cactgaggaa tttcacatga agtgtaatcc    660
ctagtcaata agaattatcc attacattat tttatgggaa aactaggcta aattacatcc    720
attcaggtaa aaggacctta gcttactgaa ggatctaaag agcaaagcaa agatctcact    780
actcaaacac tcagcctgct tccttcaagt ccccttgcag gccagctttg tgctttgcag    840
accaactttt taatgagata ctttgcttcc tcattcaaca ttgaagctag gcttcaatta    900
aaaggttcga ggaagctcca tttaaaattg ttttttttac tattttttaa aattgtagtg    960
tatatgatag gaatttgcat ttaaatatgt tcattttgc atatgttagg agtggaaaca   1020
atctggaaaa cattttttttt tcatccaaaa agtattctcc ttgggcatat ctgatggaaa   1080
aaaaccttga ttttattttc gtatctttag tctgtgttct ttctagttat ttggtactaa   1140
ttatgtgcaa tctaaaaaca ctcccacaag tatttgtttt ttaattataa aatcatagta   1200
tatgttcttt gtagaaaact ggaaaaatac atattcaaac aggaaaaaaa atcaaaattc   1260
cccataatgt tgccatctaa aaataaccte tatttagtt gatatcccgt attcattttt   1320
gaaagccatt ccttaatgct agtttgatac acactaaaag tttagcttac aagttcaaat   1380
tctgccagct tttcctgaca gctatttgca ttttttttcag atgagtgatt attggccatt   1440 ttcttttttct ttttctttat tttatttatt tattttttg agacagagtt ttgctctgtt   1500
gcccaggctg gagtgcagtg gtgcaatctc ggctcactgc aacctctgcc tcctgggttc   1560
aagtgattct ccacctcagc ctcccaagta gctgggacta cggatgcctg ccaccacgcc   1620
tggctaattt tttttttgtat ttttttgtag acacggggtt tcaccatgtt gtccaggcta   1680
atcttgaact tgtgacctca ggtgatccac ccgcctcggc ctcgaaagt gctgggatta   1740 caggcgtgag ctaccacgcc cggccttatt gaccattttc taaataagca cattctatct   1800
ttattctctt aaaattcaaa ttttctgtta ctgataatcc taatactagg attcttgctt   1860
aagtatgtga aaccattacc gatttgttgt tcacatttat tttttatgtt gtgaaactgg   1920
actaaaggaa tagagggatg attagtcata aaagtcaaat agcatttgtg tttaactgtt   1980
gagaaaagtg aaagatcagt atgattatta tggaactgtt tttaattctt gcttaaagac   2040
tacaatttta gtataatgac atttgagtct agggtagtat gtggtagatt tctagatggt   2100
ccctaattaa gaagtattgt tgtatttaga attgtccacc taatttcttt ttatataatg   2160
ccaaggtatt tcttgtgctt ttgggatctt atgctgtttg taaaatgtta ctgtccaatg   2220
ttggattatt gttttggttt caggcatttg ctgaataggt gatgatacat gggtattttt   2280
ctgcaagtat ttaaaccagg ggcatatgca aaggcagttg taatttcctc ttggaaaaag   2340
cgccaaatgt ttgaaggtta aaatcaaatg ctagggttga tatttaggct tataacaaaa   2400
taggcttgtt ttcaaaagcag ttttttccta gagttttaac tgttaactca ctagtttgct   2460
gctgttttta actatgttaa ataacatatg gtatttggca aatagattta tttttcaaaa   2520
tgtctcacta gtttcctttt acacaatgta tatacttcaa gatgtataga aaggaaagct   2580
acagttgagc ccttatacat gttttaaggt agaaatatgt tccctattgt ttgaaaactg   2640
attgtaagaa taacctcagt taggagatat aacttgaagt gtcagtccaa actactgatt   2700
taaccctatt tacggtaaca cattaccttc ctcacctcct gtttggccct ggagaatgta   2760 gtccttttttc tcatttgtgt tgagaaatga aaagtctgct gtagaatgta tctgatgtca   2820
ttagttcttc aaatggatac cattgtacat ataacagtag aatttggttt ggggttgtta   2880
```

| | | | | |
|---|---|---|---|---|
| gtgaaaaaaa | atttaaacct | gccattaaaa | atccccatgt | ttcatggaaa tctaacagaa | 2940 |
| atacattgta | ataattagaa | catttgttt | tcttttttct | tttttttttt ttcgagacgg | 3000 |
| agttttgccc | ttcttgccca | ggctggagtg | caagggcgca | atctcggctc gctgcaacct | 3060 |
| ccgcctccg | ggttcaagca | gttctcctgc | ctcagccccc | tgagtacctc agatgacagg | 3120 |
| tgcgtgccac | cacacccggc | taatttttgt | attttagta | gagacggggt ttcaccatgt | 3180 |
| tagccaggct | agtctcgaac | tcctgacctc | aggtgatcca | cccgcctccg cctcccaaag | 3240 |
| tgctgggatt | acaggtatca | gccaccgtgc | ctggcctaat | aattggaaca ttttcatcat | 3300 |
| gaaaatgtca | tcagctttgc | caaaagaaac | aaccaattga | cttgtttggc gtttgttttc | 3360 |
| cattttcatg | tcaattttat | gtatacagtt | agaataccca | aggagaccac taaaatcagt | 3420 |
| taaacaagta | gggtatatac | aaagaaagat | gaaacccgaa | agtacataaa aaggatttaa | 3480 |
| atccgatttt | agatgtacct | agtgtgtatt | tcttatctct | agacaagttc atgtttattg | 3540 |
| tttaatttat | gcccaagtga | agttgtaaac | ttatggttca | actctgacac agaatttgtc | 3600 |
| acttgtctga | ggtcagtggc | aggtttctct | gctgtcaagc | actctgtgtc acccaccaga | 3660 |
| ttagtataac | tattaattca | gactgtactc | ctatgtttaa | gataattttt acaagagctg | 3720 |
| gctgaagcag | cacattagta | acctgacaag | atttctttt | cccttttcag ggggaaaggg | 3780 |
| tcaccttaaa | aataaattat | tttcaggac | tttgggaatc | taatgataaa tattacacat | 3840 |
| aatctatgaa | tagcttaatc | ctttatatat | tccttaaaat | aggaattcct cgacatcact | 3900 |
| cctggccaca | ctttccttgc | ctgtgttgtt | gctatgtgta | tttgaaagta atatctgcat | 3960 |
| tcctttaag | atgttctgta | agtcatattt | gtcagttata | cagagtagtc ttcctttcc | 4020 |
| ccacgttcag | tgtaatctca | ctgaacagta | ataatagcaa | tagctaacaa catctgcaca | 4080 |
| gcaccttaca | gtttgcaaag | aacgttcaca | cattctcatt | tgagttttgc atagtgaacc | 4140 |
| tgttacgaga | tgtctcttga | cgtcgatgct | aaaagtgtta | gaatctttac atcactagag | 4200 |
| tcattgaata | tgctgtagta | ttgaatagtg | ccctgactag | ggggaggatt tggatgtgct | 4260 |
| gcatttcaag | ccgtgtataa | tcatcaaaat | ggggggcttg | agttctttag ctacttgaat | 4320 |
| ccgatttact | tctgttaagt | gatgcttttc | taaccgtttt | ctggatggat tttgtattca | 4380 |
| ctatattgta | gcttgtaatt | tgtataaatg | taccatctga | tgtcattaaa aaaagtgttt | 4440 |
| gtagtgct | | | | | 4448 |

<210> SEQ ID NO 5
<211> LENGTH: 6269
<212> TYPE: DNA
<213> ORGANISM: Homo sapiens

<400> SEQUENCE: 5

| | | | | |
|---|---|---|---|---|
| gtagccctga | gcggggcctg | gaccgcgagg | cggactggcc | ccagcctgga gcagggcttg | 60 |
| agggaaggcc | ctagctgaat | gggtgggcgt | gaggtctgga | ccccgggac ctggcctcag | 120 |
| ggaaggggc | ggggaaagca | ggttggagcc | tgagacgtct | aaactcccgg ccccgaactt | 180 |
| tcgctcggga | acaagggatc | cggggtcatg | gggaataggt | cagtgggcct tcagctcatg | 240 |
| ctcctatcct | agcactttct | ctcgctgtgt | ctatattgca | gtctctttca ttaccgcagg | 300 |
| gtcagccttc | tgaggacagg | aatgcagtct | ccttcatctc | cgtgttccct aggggcctg | 360 |
| catagtcggg | gcttaataaa | tgtttgctgt | atgaatgaag | gagtagaagg gaatagtccc | 420 |
| ctggtgtgag | attgcttcac | ttggggaatc | agtaagatag | aggctggtga ctgagttgaa | 480 |
| ggaatgtatg | agagagcagg | tggttctggc | ccaccccagt | aggcaaggga gtggtgaggg | 540 |

-continued

```
agttagctat cattcgttaa gacctactgt atgccaggct cagtgcacgt gctttacata    600
cattgtcaga attcttaatt tctctaactg cttgatttcc caattttgaa gaggatgcag    660
ttgagggtaa gtgacttgaa actgagggtg agtgattaca gaattaggcg acaaagttag    720
tatgtaattg aagctaacgt ttgaccaagc tcactgactc caaagcccac gatctttgga    780
gctctgtgat gccttctctt tccgacaggg tcattgtgag tttttttttt tttttttttaa   840 cttttatttt aggttcatga gtacatgcgc aggtttgtta tataggtaaa ctgcatgtca    900
cgggggcttg gcgtacaggt aattttgtca cccaggtaat aagcatagta cccgataggc    960
gttttttctg attctctccc tcctcccagc ctccaccctc aagtagaccg cactgtctgt   1020
tgttcctctc ctagtgtcca tctgttcttg ttgtttagtt cccacttatg agaacgtgca   1080
gtatttggtt ttcttttcct gtcttaattt gcttagaata atggcttcca gctccagtca   1140
tgttgctgca aaggacatga tctcattctt ttttatggct gcatagtgtt ccatggtgta   1200
tatgtaccgc attttcttta tccagcctca atgtgggttt ttttttaatt attcatttat   1260
gagaatacca acatatttt attagataca cttacagcat agtccttcta gactgattct    1320
ggtttcctaa tggaatttgc agtgaaatct tgactgtggg agaaagaatt cctgttgtct   1380
tacttgctac aaaagggaat gtggtaggct ctgtctgctc aatgttggct gcagaagttt   1440
gtatgaagtg ggaaaactag gtggtgttat aaatggaggc agattaaggt tcatcctgaa   1500 cttttttcctt tgtgtgagga caactttaat tccagccttt ctcattcctc acttctaaca   1560
aatctctgct cagtaacacc caaagataca taggataaat caattgaata gcatcagttg   1620
ctttgtcttg gataagccac tgattttacc caaggtggct tgcatcagca aaaccaacag   1680
ctcttgtggc tggaatccag ggagaaaatg tcctataaac agtagaggaa gtttgctagt   1740
tttcaaaagt ttgtatgtac actttgactt aatgcttagt cccatattag tgaggtcaca   1800
acacagaaaa gtagtcacat ttttgaagtt tgaggtaaag agagaagtga gaaggaatta   1860
gccataaatt attaaggtat gctgtgtata gattgtgtgg gggctagaaa ttaatatgta   1920
gaaaggttat atttgggtgg tgggattata ggtgattttg tttactttaa aacattttta   1980
tggtgttata tcatcttttc aataataaac ttttaaaag ccagaccaga taatagatac    2040
tcaagagagg tcatgtaaag aacaaaacaa tcagttaaca cttcctttct gttccttaa    2100 caagttagat aatctgaaag ttgcattcct aaaacatact tttttactca ccatagaaac   2160
accaaagtca agtgcttttt ttagggtgca caaaagaatt ggccaattag tgactctttg   2220 tatttttgt agattctcca ctgcagacac tcatactctt catgaggatt acacaataaa    2280
tttctctaaa aatttactag taggaaacag tttaagggag cttatgtata ttaaatgaga   2340
gttgtatagc tcagtaataa ccaaaatgag gcctgctaaa agatgatcca tttaagtacc   2400
aaaagaaaat attagaactt ttttttttac agcagtaagc atttaatttc tcacacatgt   2460
gcagagcatg tgatcaagaa ataggcatga ggttagttat atttaatata tattttactc   2520
aatgtttttg tgggtttttt gttcaggttc ttttaaata aatttcattg tgtatatttg    2580
aggttcataa catgatgtta tggcatacat atagtaaaat gattactatg gtgaagcaga   2640
ttaatatatc tgtcatctca catacttttg tgtgtgtg accagaggca gctaaaatct     2700
tatttacaaa agtccctaat accatgcaac tttattgcct atagtcctct tgtacattag   2760
atatctcact tgttaatcca tatatctact gctttgtgtc ctttgatgta tatcttccta   2820
tttcctcccc tccagcctcc cacccccacc gccatggtaa ctactgtttt attctctgtc   2880
cctgtgtagt tgaccgttga cctttttttt tttttttaa agattccaca tataagtgag   2940
```

```
ctcatgtagt attcgtctttt ctgcgtttgg cttattttac ttaacatgtc ttccaggtcc    3000
atccatgttg tggcaaatgg cagatgtcct cttttaaggc tgaataaaat attcccttgt    3060
atatatacac tacggtttct ttattttgtc tgtctacata cacgtaggtt gttttcaaat    3120
cttggctatt gtgaataatg ctgcaatgaa catggaagtg cagatatttt tacgaggtag    3180
tgatttcatc tcctttgctt atattccaga agagagattg ctgggctgtg tggtagttct    3240
atttttaatt tctttaggaa ctgttttcca taatggctgt accagtctac atttccagtc    3300
acaatgtagt agggtttctt tttctccaca cttttacaaa catttgttat cacttgcctt    3360
tttgataata gctgtcctta gaagtgtgag gttatatctc atagtggttt tgatttgcat    3420
ttccctgatg atttagtgat gttgagcaca ttttcattta tctcttggcc attttatgt     3480 ctttggagaa atgtctgtcc agctgttgtc catatttta  tcaggtggtt tttctgctga    3540
gttgtaagag ttcttataa  attttggggt attaacccct tacaagatag gtggttcgca    3600
aatatgtttt cctagtctgt aagctgcctt ttcattttgt tgattgtttc ctttgcagta    3660
cagaagcttt ttagtttgat gcaagccgct ttattttttc ttttgtagcc tgagcttttg    3720
gtgtgatatc caaaaaatca ttactgaggc caatgttaag gaccttttccc tctgtgttct    3780 tttatgtctt aaaactttat atctttatgt tttagttatt ttatccatt t tgggttgatt    3840 tttgtttatg gtgtaagagt ccagttttttt tctttgcatg tagaaatcct gttttcccag    3900
taccacttat tgaagggact gtcctttccc cattgtgttc ctcttaacac ccctgtcgaa    3960
gattagttgg ccatatatgt ttggatttat ttctgggctc tattctgttt cattgttata    4020
tgtttctgtt tttatgccaa taccatattg ttttgattac tataactgta atattttaaa    4080
tcagaaagtg tgatgcttac aactttttca atgttgcttt ggctatttgg ggcttttttgt    4140 ggttctgtat gatgaatttt aggattgttt ttctatttta atgaagaatg ctactgtaat    4200
tttgatagag attgtgttat atctgtatgt tgctttgggt gctgtagaca tttcaacagt    4260
attaattctt ccaatccatg aacacaggat atctttacat ttatttgtgt catcttcaat    4320
ttctttcatc agtgttttat acttttcagt gtacaagtca ctcatcgcct tggttaaatt    4380
tattcctaag tttcttttttt tttgaaatag agtcttgctc tgtcacccag gccagagtaa    4440
agtgccccaa tcactgctca ctgcagcctt gacctctggg gctcaaacaa tcctcccact    4500
tcagcctctt gagtagctga gattacaggc acgtgccacc atgcccagcg aattatcaaa    4560
attttttttt gtagaggtgg ggttttgctg tgttacctag gcttgcgtca aactcccggc    4620
ctcaagcctc agccttccca aagtgctggg attacaggca tgagccactg agcctggccc    4680
ctaagtattt ttttttaatg ctattataaa tgagattgtt ttcttgattt cttttttcagc    4740 tcagtaaagg atgcggaagt ttgtcaagtg cttttttctgc atcaactgag atgatcctac    4800
ttggtcataa tatataatct ttttgatgta ttggttttgt ttgtttgtga cagagtcttg    4860
ctctgttgcc cagactggag tgtgattttg gctcattgca acctctgcct cccaggatca    4920
agggattctt gtgccttggc ctcccaagta gctgggacta taggcacacg ccaccactct    4980
cagctaattt ttgtattttt agtagagact gggttttgcc atgttggcca ggctgatctc    5040
gaactcctgg cctcaagtga tccgcctgcc tcggcctccc aaagtgctgg gattacaggt    5100
gtgagccacc acacctggcc tgattattgt tgaatttggt ttgaaaatat gttattgagg    5160
aattttgcac cagtgttcat cagtgatgtt gtcctgtagt tttcttgctg tgtctgtctg    5220
gcttaggtat caaggtgatt ggagcctctt aaaacgtgtt tggaagtatt ccctctagct    5280 cgattttttca cccataacag aagttcctat tccagctggg gagggcgcac tggtccgttc    5340
```

```
gccctgccta cctccttcag tggtctggtg tctggtgctg gtggtcaggg ttgctgcacg    5400
ggctcaggga ctggtgtggc agtggcttcc ctgggccaaa gctctgatcc cagtgggga     5460 gggcacgctg gtgcgtcggc tccacctggt tagtttgctg gtccactgtc tggtgctgga    5520
ggacaggagg ctggcagctt cccagatgc aagctccgat tccagcggga gagggcacac    5580
tgctccacct gtggtgcctg ccgagttccc tggtctggtg tccggtgctg tggtcaggg     5640 ttgctgcgtg ggctcaggga ccagtgtgac agtggcttcc ctgggcaaaa gctctgattc    5700
cagtgtggga gggtgcacag gtgtgtctgc ctcgttagtt ccctggtcca ctgtctcatg    5760
ctggaggaca gcaagctggt cgcttcccgt gacggaagct ctgattccag caaaagaggg    5820
cgcgctgatc cacccatggt gcctgctgcg ttcccagctc tggtgtctgg tgctggtgga    5880
cacggttgcc gcatgggttg ggcactggtg ccgctgtccg ccgtggcttc cctgggtaaa    5940
agctccagtt ccagaggcag gggcactgag tttcttcact tagtttgttc acccagcttg    6000
ttggcagttg atctgaggtg ccctgacgct cgtcttaca ctggatatga atgacagtcc      6060
ctaaaggtgg tgtataatct tcatgttcca gctcaagaaa ttcccactac ccacagctgg    6120
ttctctagga tcttcggatt acgagtccct gcctgtgatc ttcctcctgc atagcatctc    6180
atttgtggat gtttatagtt tcagggacat aagagcgttt ggatatgact gtgcaggttc    6240
tgattttctc tttgtttact ttattccag                                      6269

<210> SEQ ID NO 6
<211> LENGTH: 1175
<212> TYPE: DNA
<213> ORGANISM: Homo sapiens

<400> SEQUENCE: 6
gtaatcttag acccattaaa acaagatgtt ttcccccaat ttaagattct gtgcttttat      60
gacctcttta tatctttaaa ctgggtattc ttattttttt cttgtttagc ttttcaaaaa    120
atcatattgc tcataatgag tctttatgaa ataacttatt gtttcagctt gacagttttc    180
ctatggtttt ctgtgaaata gcttgcaaat cctttctctt agtacctttt aaagaatagg    240
ggttggctga catgggagga ggaattttgg gggaatggac tttagtgtca gataacggaa    300
ggaagagaga atgaagtccc cttttttgatg ttgaaatttt ttttttttttt ttgagacagt   360 ttcactcttg ttgcacaggc tggagtgcaa tggcgcgatc tcggctcacc gcaacccccg    420
cctcccatgt tcaagcgatt ctcctgtctc agcctcctga gtatctggga ttacaggcac    480
ccgccactac acccgactga ttttttggtat ttttagtaga cggggtttt cgccatgttg     540 gccaggctgg tctcgaactc gtgaccctcag gtgatccacc cgcctcggcc tcccagagtg    600
ctgggattac aagcgtgagc caccgcaccc ggcctgaagt cttataatt atggttttgt      660 ttaaaacaat gtttgtttgt tgtttgttt gttttttgaga cggagtctcg ctcagtcacc    720
caggctggag tgcagtggtg cgatctcggc tcgcgtcaag ctctgcctcc caggttcacg    780
ccattctgct gcctcagcct cccgagtagc tgggactaca ggcgcctgcc actacgcctg    840
gctaattttt tttgtatttt tagtagagac ggggtttcac ggtgctagcc aggatggttt    900
ccatctcctg acctcgtgat ctgcccgtct tggcctccca aagtgctggg attacaggcg    960
tgagccactg cacccggcca acataatgtt cttaatatat agaaggtact catatctttt    1020
agtgaatact ttattcatta ccacccaaaa tattactttt taattgcctg actagttaaa    1080
taaatacatc ataaaaatta ggatgctttg ttttttttt ttgtactttg gtaaattttg     1140
caataaaatg gaaactgttt tttttctctt gatag                               1175
```

<210> SEQ ID NO 7
<211> LENGTH: 4687
<212> TYPE: DNA
<213> ORGANISM: Homo sapiens

<400> SEQUENCE: 7

| | | | | | | |
|---|---|---|---|---|---|---|
| tccctcgcgg | agcttactga | gcgcggccgc | cgagcccagc | tccgccgccg | agcgcctgtg | 60 |
| ccggcacggc | tacaccatgg | agcgcccgga | taaggcggcg | ctgaacgcac | tgcagcctcc | 120 |
| tgagttcaga | aatgaaagct | cattagcatc | tacactgaag | acgctcctgt | tcttcacagc | 180 |
| tttaatgatc | actgttccta | ttgggttata | tttcacaact | aaatcttaca | tatttgaagg | 240 |
| cgcccttggg | atgtccaata | gggacagcta | tttttacgct | gctattgttg | cagtggtcgc | 300 |
| cgtccatgtg | gtgctggccc | tctttgtgta | tgtggcctgg | aatgaaggct | cacgacagtg | 360 |
| gcgtgaaggc | aaacaggatt | aaagtgaaca | tcaccttttt | atagcattaa | attcattttt | 420 |
| taaaatgata | aatgctggag | ggggccatct | gatttgaata | aagtcgaaag | aacatgttaa | 480 |
| agtcagtctt | aaggagtcac | gtttgagtat | gtaaattttg | atctttctaa | tatgttggtt | 540 |
| tgtatattca | gttttaactg | tatgaatctg | atttgcaaat | gagaatttgg | aaaagttagt | 600 |
| tacaaagaaa | tatgttaatt | taattagaca | atactctgga | aggaatttta | tcttctttca | 660 |
| acaaaacatg | ttttatagta | ttctgactta | cggttgcttt | tgagttttac | tcatttggat | 720 |
| atattaagat | gcacacagtg | aagcaaatta | aactccactt | tacgctggaa | tgctttcttt | 780 |
| agcatgaaaa | taccaggtcc | ttggatttgg | gattttaatt | tcctatggaa | agttgcttaa | 840 |
| attgtgaca | ctggaattaa | tctgaatgtc | actgaggaat | tcacatgaa | gtgtaatccc | 900 |
| tagtcaataa | gaattatcca | ttacattatt | ttatgggaaa | actaggctaa | attacatcca | 960 |
| ttcaggtaaa | aggaccttag | cttactgaag | gatctaaaga | gcaaagcaaa | gatctcacta | 1020 |
| ctcaaacact | cagcctgctt | ccttcgagcc | cccttgcagg | ccagctttgt | gctttgcaga | 1080 |
| ccaacttttt | aatgagatac | tttgcttcct | cattcaacat | tgaagctagg | cttcaattaa | 1140 |
| aaggttcgag | gaagctccat | ttaaaattgt | ttttttttact | atttttttaaa | attgtagtgt | 1200 |
| atatgatagg | aatttgcatt | taaatatgtt | cattttgca | tatgttagga | gtggaaacaa | 1260 |
| tctggaaaac | atttttttttt | catccaaaaa | gtattctcct | tgggcatatc | tgatggaaaa | 1320 |
| aaaccttgat | tttattttcg | tatctttagt | ctgtgttctt | tctagttatt | tggtactaat | 1380 |
| tatgtgcaat | ctaaaaacac | tcccacaagt | atttgttttt | taattataaa | atcatagtac | 1440 |
| atgttctttg | tagaaaactg | gaaaaataca | tattcaaaca | ggaaaaaaaa | tcaaaattcc | 1500 |
| ccataatgtt | gccatctaaa | aataacctct | attttagttg | atatcccgta | ttcatttttg | 1560 |
| aaagccattc | cttaatgcta | gtttgataca | cactaaaagt | ttagcttaca | agttcaaatt | 1620 |
| ctgccagctt | ttcctgacag | ctatttgcat | ttttttcaga | tgagtgatta | ttggccattt | 1680 |
| tcttttttctt | tttctttatt | ttatttattt | attttttttga | gacagagttt | tgctctgttg | 1740 |
| cccaggctgg | agtgcagtgg | tgcaatctcg | gctcactgca | acctctgcct | cctgggttca | 1800 |
| agtgattctc | cacctcagcc | tcccaagtag | ctgggactac | ggatgcctgc | caccacgcct | 1860 |
| ggctaatttt | ttttttgtatt | ttttttgtaga | gacggggttt | caccatgttg | tccaggctaa | 1920 |
| tcttgaactt | gtgacctcag | gtgatccacc | cgcctcggcc | tcgaaagtg | ctgggattac | 1980 |
| aggcgtgagc | taccacgccc | ggccttattg | accatttttct | aaataagcac | attctatctt | 2040 |
| tattctctta | aaattcaaat | tttctgttac | tgataatcct | aatactagga | ttcttgctta | 2100 |
| agtatgtgaa | accattaccg | atttgttgtt | cacatttatt | ttttatgttg | tgaaactgga | 2160 |

```
ctaaaggaat agagggatga ttagtcataa aagtcaaata gcatttgtgt ttaactgttg    2220
agaaaagtga aagatcagtg tgattattat ggaactgttt ttaattcttg cttaaagact    2280
acaattttag tataatgaca tttgagtcta gggtagtatg tggtagattt ctagatggtc    2340
cctaattaag aagtattgtt gtatttagaa ttgtccacct aatttctttt tatataatgc    2400
caaggtattt cttgtgcttt tgggatctta tgctgtttgt aaaatgttac tgtccaatgt    2460
tggattattg ttttggtttc aggcatttgc tgaataggtg atgatacatg ggtattttc     2520 tgcaagtatt taaaccaggg gcatatgcaa aggcagttgt aatttcctct tggaaaaagc    2580
gccaaatgtt tgaaggttaa aatcaaatgc tagggttgat atttaggctt ataacaaaat    2640
aggcttgttt tcaaagcagt ttttttcctag agttttaact gttaactcac tagtttgctg    2700
ctgtttttaa ctatgttaaa taacatatgg tatttggcaa atagatttat ttttcaaaat    2760
gtctcactag tttcctttta cacaatgtat atacttcaag atgtatagaa aggaaagcta    2820
cagctgagcc cttatacatg ttttaaggta gaaatatgtt ccctattgtt tgaaaactga    2880
ttgtaagaat aacctcagtt aggagatata acttgaagtg tcagtccaaa ctactgattt    2940
aaccctattt acggtaacac attaccttcc tcacctcctg tttggccctg agaatgtag     3000 tccttttttct catttgtgtt gagaaatgaa aagtctgctg tagaatgtat ctgatgtcat    3060
tagttcttca aatggatacc attgtacata taacagtaga atttggtttg gggttgttag    3120
tgaaaaaaaa tttaaacctg ccattaaaaa tccccatgtt tcatgaaat ctaacagaaa     3180 tacattgtaa taattagaac attttgtttt cttttttctt tttttttttt tcgagacgga    3240
gttttgccct tcttgcccag gctggagtgc aagggcgcaa tctcggctcg ctgcaacctc    3300
cgcctcccgg gttcaagcag ttctcctgcc tcagcccct gagtacctca gatgacaggt     3360
gcgtgccacc acacccggct aattttttgta ttttttagtag acacggggtt tcaccatgtt    3420
agccaggcta gtctcgaact cctgacctca ggtgatccac cgcctccgc ctcccaaagt     3480 gctgggatta caggtatcag ccaccgtgcc tggcctaata attggaacat tttcatcatg    3540
aaaatgtcat cagctttgcc aaaagaaaca accaattgac ttgtttggcg tttgttttcc    3600
attttcatgt caattttatg tatacagtta gaatacccaa ggagaccact aaaatcagtt    3660
aaacaagtag ggtatataca aagaaaggtg aaacccgaaa gtacataaaa aggatttaaa    3720
tccgatttta gatgtaccta gtgtgtattt cttatctcta gacaagttca tgtttattgt    3780
ttaatttatg cccaagtgaa gttgtaaact tatggttcaa ctctgacaca gaatttgtca    3840
cttgtctgag gtcagtggca ggtttctctg ctgtcaagca ctctgtgtca cccaccagat    3900
tagtataact attaattcag actgtactcc tatgtttaag ataattttta caagagctgg    3960
ctgaagcagc acattagtaa cctgacaaga tttcttttc cctttcagg gggaaagggt      4020 caccttaaaa ataaattatt ttcagggact ttgggaatct aatgataaat attacacata    4080
atctatgaat agcttaatcc tttatatatt ccttaaaata ggaattcctc gacatcactc    4140
ctggccacac tttccttgcc tgtgttgttg ctatgtgtat ttgaaagtaa tatctgcatt    4200 cctttaaga tgttctgtaa gtcatatttg tcagttatac agagtagtct tccttttccc     4260
cacgttcagt gtaatctcac tgaacagtaa taatagcaat agctaacaac atctgcacag    4320
caccttacag tttgcaaaga acgttcacac attctcattt gagttttgca tagtgaacct    4380
gttacgagat gtctcttgac gtcgatgcta aaagtgttag aatctttaca tcactagagt    4440
cattgaatat gctgtagtat tgaatagtgc cctgactagg gggaggattt ggatgtgctg    4500
```

```
catttcaagc cgtgtataat catcaaaatg gggggcttga gttccttagc tacttgaatc    4560
cgatttactt ctgttaagtg atgcttttct aaccgttttc tggatggatt ttgtattcac    4620
tatattgtag cttgtaattt gtataaatgt accatctgat gtcattaaaa aaagtgtttg    4680
tagtgct                                                              4687

<210> SEQ ID NO 8
<211> LENGTH: 82
<212> TYPE: DNA
<213> ORGANISM: Homo sapiens

<400> SEQUENCE: 8
gggtcactgg catcgagtct ggaacagtca ttctcagcaa gagctctttg aactctgaca     60
ttctctagtt ttacggactc gg                                              82

<210> SEQ ID NO 9
<211> LENGTH: 259
<212> TYPE: DNA
<213> ORGANISM: Homo sapiens

<400> SEQUENCE: 9
caccacagcc ctctggctgg tagtccctct tcgcggctca tatgctcggg tctccttgcg     60
gcccccagct cagcgaccga gacgcagacg aggaccagtg ttcacgcgag ttcaggggc    120 ggcgtagccg ccgcccgccc aggaggacca tgttgcgcgg caagtccgg ctcaacgtgg    180 agtggctggg ctactcgcca ggcctgctcc tcgagcacag gcccctcctg gcagggcgca    240
cgccgcggag ccaccgccg                                                 259

<210> SEQ ID NO 10
<211> LENGTH: 693
<212> TYPE: DNA
<213> ORGANISM: Homo sapiens

<400> SEQUENCE: 10
gggtcactgg catcgagtct ggaacagtca ttctcagcaa gagctctttg aactctgaca     60
ttctctagtt ttacggactc ggcaccacag ccctctggct ggtagtccct cttcgcggct    120
catatgctcg ggtctccttg cggcccccag ctcagcgacc gagacgcaga cgaggaccag    180
tgttcacgcg agttcagggg gcggcgtagc cgccgcccgc ccaggaggac catgttgcgc    240
ggcaagtccc ggctcaacgt ggagtggctg ggctactcgc caggcctgct cctcgagcac    300
aggcccctcc tggcagggcg cacgccgcgg agccaccgcc gaaatgaaag ctcattagca    360
tctacactga agacgctcct gttcttcaca gctttaatga tcactgttcc tattgggtta    420
tatttcacaa ctaaatctta catatttgaa ggcgcccttg ggatgtccaa tagggacagc    480 tattttacg ctgctattgt tgcagtggtc gccgtccatg tggtgctggc cctctttgtg    540
tatgtggcct ggaatgaagg ctcacgacag tggcgtgaag gcaaacagga ttaaagtgaa    600
catcaccttt ttatagcatt aaattcattt tttaaaatga taaatgctgg aggggccat    660 ctgatttgaa taaagttgaa agaacatgtt aaa                                 693

<210> SEQ ID NO 11
<211> LENGTH: 101
<212> TYPE: PRT
<213> ORGANISM: Homo sapiens
```

-continued

<400> SEQUENCE: 11

Met Glu Arg Pro Asp Lys Ala Ala Leu Asn Ala Leu Gln Pro Pro Glu
1               5                   10                  15

Phe Arg Asn Glu Ser Ser Leu Ala Ser Thr Leu Lys Thr Leu Leu Phe
            20                  25                  30

Phe Thr Ala Leu Met Ile Thr Val Pro Ile Gly Leu Tyr Phe Thr Thr
        35                  40                  45

Lys Ser Tyr Ile Phe Glu Gly Ala Leu Gly Met Ser Asn Arg Asp Ser
    50                  55                  60

Tyr Phe Tyr Ala Ala Ile Val Ala Val Val Ala Val His Val Val Leu
65                  70                  75                  80

Ala Leu Phe Val Tyr Val Ala Trp Asn Glu Gly Ser Arg Gln Trp Arg
                85                  90                  95

Glu Gly Lys Gln Asp
            100

<210> SEQ ID NO 12
<211> LENGTH: 156
<212> TYPE: PRT
<213> ORGANISM: Homo sapiens

<400> SEQUENCE: 12

Met Leu Gly Ser Pro Cys Gly Pro Gln Leu Ser Asp Arg Asp Ala Asp
1               5                   10                  15

Glu Asp Gln Cys Ser Arg Glu Phe Arg Gly Arg Ser Arg Arg Pro
            20                  25                  30

Pro Arg Arg Thr Met Leu Arg Gly Lys Ser Arg Leu Asn Val Glu Trp
        35                  40                  45

Leu Gly Tyr Ser Pro Gly Leu Leu Leu Glu His Arg Pro Leu Leu Ala
    50                  55                  60

Gly Arg Thr Pro Arg Ser His Arg Arg Asn Glu Ser Ser Leu Ala Ser
65                  70                  75                  80

Thr Leu Lys Thr Leu Leu Phe Phe Thr Ala Leu Met Ile Thr Val Pro
                85                  90                  95

Ile Gly Leu Tyr Phe Thr Thr Lys Ser Tyr Ile Phe Glu Gly Ala Leu
            100                 105                 110

Gly Met Ser Asn Arg Asp Ser Tyr Phe Tyr Ala Ala Ile Val Ala Val
        115                 120                 125

Val Ala Val His Val Val Leu Ala Leu Phe Val Tyr Val Ala Trp Asn
    130                 135                 140

Glu Gly Ser Arg Gln Trp Arg Glu Gly Lys Gln Asp
145                 150                 155

<210> SEQ ID NO 13
<211> LENGTH: 120
<212> TYPE: PRT
<213> ORGANISM: Homo sapiens

<400> SEQUENCE: 13

Met Leu Arg Gly Lys Ser Arg Leu Asn Val Glu Trp Leu Gly Tyr Ser
1               5                   10                  15

Pro Gly Leu Leu Leu Glu His Arg Pro Leu Leu Ala Gly Arg Thr Pro
            20                  25                  30

Arg Ser His Arg Arg Asn Glu Ser Ser Leu Ala Ser Thr Leu Lys Thr
        35                  40                  45

Leu Leu Phe Phe Thr Ala Leu Met Ile Thr Val Pro Ile Gly Leu Tyr
    50                  55                  60

```
Phe Thr Thr Lys Ser Tyr Ile Phe Glu Gly Ala Leu Gly Met Ser Asn
 65                  70                  75                  80

Arg Asp Ser Tyr Phe Tyr Ala Ala Ile Val Ala Val Val Ala Val His
                 85                  90                  95

Val Val Leu Ala Leu Phe Val Tyr Val Ala Trp Asn Glu Gly Ser Arg
            100                 105                 110

Gln Trp Arg Glu Gly Lys Gln Asp
        115                 120

<210> SEQ ID NO 14
<211> LENGTH: 18
<212> TYPE: DNA
<213> ORGANISM: Artificial Sequence
<220> FEATURE:
<223> OTHER INFORMATION: Description of Artificial Sequence: Synthetic
      primer sequence

<400> SEQUENCE: 14
gagtggctgg gctactcg                                                   18

<210> SEQ ID NO 15
<211> LENGTH: 21
<212> TYPE: DNA
<213> ORGANISM: Artificial Sequence
<220> FEATURE:
<223> OTHER INFORMATION: Description of Artificial Sequence: Synthetic
      primer sequence

<400> SEQUENCE: 15
gacacagcga gagaaagtgc t                                               21

<210> SEQ ID NO 16
<211> LENGTH: 20
<212> TYPE: DNA
<213> ORGANISM: Artificial Sequence
<220> FEATURE:
<223> OTHER INFORMATION: Description of Artificial Sequence: Synthetic
      primer sequence

<400> SEQUENCE: 16
tcctcctgca tagcatctca                                                 20

<210> SEQ ID NO 17
<211> LENGTH: 22
<212> TYPE: DNA
<213> ORGANISM: Artificial Sequence
<220> FEATURE:
<223> OTHER INFORMATION: Description of Artificial Sequence: Synthetic
      primer sequence

<400> SEQUENCE: 17
ggaaaactgt caagctgaaa ca                                              22

<210> SEQ ID NO 18
<211> LENGTH: 24
<212> TYPE: DNA
<213> ORGANISM: Artificial Sequence
<220> FEATURE:
<223> OTHER INFORMATION: Description of Artificial Sequence: Synthetic
      primer sequence

<400> SEQUENCE: 18
actttattca ttaccaccca aaat                                            24
```

```
<210> SEQ ID NO 19
<211> LENGTH: 27
<212> TYPE: DNA
<213> ORGANISM: Artificial Sequence
<220> FEATURE:
<223> OTHER INFORMATION: Description of Artificial Sequence: Synthetic
      primer sequence

<400> SEQUENCE: 19
caaaccaaca tattagaaag atcaaaa                                       27

<210> SEQ ID NO 20
<211> LENGTH: 18
<212> TYPE: DNA
<213> ORGANISM: Artificial Sequence
<220> FEATURE:
<223> OTHER INFORMATION: Description of Artificial Sequence: Synthetic
      primer sequence

<400> SEQUENCE: 20
gataaggcgg cgctgaac                                                 18

<210> SEQ ID NO 21
<211> LENGTH: 20
<212> TYPE: DNA
<213> ORGANISM: Artificial Sequence
<220> FEATURE:
<223> OTHER INFORMATION: Description of Artificial Sequence: Synthetic
      primer sequence

<400> SEQUENCE: 21
ccccctccag catttatcat                                               20

<210> SEQ ID NO 22
<211> LENGTH: 24
<212> TYPE: DNA
<213> ORGANISM: Artificial Sequence
<220> FEATURE:
<223> OTHER INFORMATION: Description of Artificial Sequence: Synthetic
      primer sequence

<400> SEQUENCE: 22
cctgagttca gaaatgaaag ctca                                          24

<210> SEQ ID NO 23
<211> LENGTH: 24
<212> TYPE: DNA
<213> ORGANISM: Artificial Sequence
<220> FEATURE:
<223> OTHER INFORMATION: Description of Artificial Sequence: Synthetic
      primer sequence

<400> SEQUENCE: 23
tcccaagggc gccttcaaat atgt                                          24

<210> SEQ ID NO 24
<211> LENGTH: 20
<212> TYPE: DNA
<213> ORGANISM: Artificial Sequence
<220> FEATURE:
<223> OTHER INFORMATION: Description of Artificial Sequence: Synthetic
      primer sequence

<400> SEQUENCE: 24
ctggaacggt gaaggtgaca                                               20
```

```
<210> SEQ ID NO 25
<211> LENGTH: 23
<212> TYPE: DNA
<213> ORGANISM: Artificial Sequence
<220> FEATURE:
<223> OTHER INFORMATION: Description of Artificial Sequence: Synthetic
      primer sequence

<400> SEQUENCE: 25
aagggacttc ctgtaacaat gca                                           23

<210> SEQ ID NO 26
<211> LENGTH: 20
<212> TYPE: DNA
<213> ORGANISM: Artificial Sequence
<220> FEATURE:
<223> OTHER INFORMATION: Description of Artificial Sequence: Synthetic
      primer sequence

<400> SEQUENCE: 26
agcagcttcc tgttctggat                                               20

<210> SEQ ID NO 27
<211> LENGTH: 20
<212> TYPE: DNA
<213> ORGANISM: Artificial Sequence
<220> FEATURE:
<223> OTHER INFORMATION: Description of Artificial Sequence: Synthetic
      primer sequence

<400> SEQUENCE: 27
ctgggaggca tagaccatgt                                               20

<210> SEQ ID NO 28
<211> LENGTH: 19
<212> TYPE: DNA
<213> ORGANISM: Artificial Sequence
<220> FEATURE:
<223> OTHER INFORMATION: Description of Artificial Sequence: Synthetic
      primer sequence

<400> SEQUENCE: 28
gtcttccgct gcagtttcc                                                19

<210> SEQ ID NO 29
<211> LENGTH: 20
<212> TYPE: DNA
<213> ORGANISM: Artificial Sequence
<220> FEATURE:
<223> OTHER INFORMATION: Description of Artificial Sequence: Synthetic
      primer sequence

<400> SEQUENCE: 29
atgagtcctt ggatggttcg                                               20

<210> SEQ ID NO 30
<211> LENGTH: 32
<212> TYPE: DNA
<213> ORGANISM: Artificial Sequence
<220> FEATURE:
<223> OTHER INFORMATION: Description of Artificial Sequence: Synthetic
      primer sequence

<400> SEQUENCE: 30
tataagcttg ctacaccatg gagcgcccgg at                                 32
```

```
<210> SEQ ID NO 31
<211> LENGTH: 35
<212> TYPE: DNA
<213> ORGANISM: Artificial Sequence
<220> FEATURE:
<223> OTHER INFORMATION: Description of Artificial Sequence: Synthetic
      primer sequence

<400> SEQUENCE: 31
tattctagag tcgaccactg acctattccc catga                          35

<210> SEQ ID NO 32
<211> LENGTH: 30
<212> TYPE: DNA
<213> ORGANISM: Artificial Sequence
<220> FEATURE:
<223> OTHER INFORMATION: Description of Artificial Sequence: Synthetic
      primer sequence

<400> SEQUENCE: 32
tatgtcgacc actgagtttc ttcacttagt                                30

<210> SEQ ID NO 33
<211> LENGTH: 37
<212> TYPE: DNA
<213> ORGANISM: Artificial Sequence
<220> FEATURE:
<223> OTHER INFORMATION: Description of Artificial Sequence: Synthetic
      primer sequence

<400> SEQUENCE: 33
tattctagaa gatcttccgt tatctgacac taaagtc                        37

<210> SEQ ID NO 34
<211> LENGTH: 27
<212> TYPE: DNA
<213> ORGANISM: Artificial Sequence
<220> FEATURE:
<223> OTHER INFORMATION: Description of Artificial Sequence: Synthetic
      primer sequence

<400> SEQUENCE: 34
tatagatcta ggcgtgagcc actgcac                                   27

<210> SEQ ID NO 35
<211> LENGTH: 29
<212> TYPE: DNA
<213> ORGANISM: Artificial Sequence
<220> FEATURE:
<223> OTHER INFORMATION: Description of Artificial Sequence: Synthetic
      primer sequence

<400> SEQUENCE: 35
tattctagaa ctgtcgtgag ccttcattc                                 29

<210> SEQ ID NO 36
<211> LENGTH: 27
<212> TYPE: DNA
<213> ORGANISM: Artificial Sequence
<220> FEATURE:
<223> OTHER INFORMATION: Description of Artificial Sequence: Synthetic
      primer sequence

<400> SEQUENCE: 36
tatggtacca tggagcgccc ggataag                                   27
```

```
<210> SEQ ID NO 37
<211> LENGTH: 27
<212> TYPE: DNA
<213> ORGANISM: Artificial Sequence
<220> FEATURE:
<223> OTHER INFORMATION: Description of Artificial Sequence: Synthetic
      primer sequence

<400> SEQUENCE: 37
tattctagaa tcctgtttgc cttcacg                                         27

<210> SEQ ID NO 38
<211> LENGTH: 25
<212> TYPE: DNA
<213> ORGANISM: Artificial Sequence
<220> FEATURE:
<223> OTHER INFORMATION: Description of Artificial Sequence: Synthetic
      primer sequence

<400> SEQUENCE: 38
ttgtaaactt atggttcaac tctga                                           25

<210> SEQ ID NO 39
<211> LENGTH: 22
<212> TYPE: DNA
<213> ORGANISM: Artificial Sequence
<220> FEATURE:
<223> OTHER INFORMATION: Description of Artificial Sequence: Synthetic
      primer sequence

<400> SEQUENCE: 39
tcaagagaca tctcgtaaca gg                                              22

<210> SEQ ID NO 40
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Glu Gln Lys Leu Ile Ser Glu Glu Asp Leu
1               5                   10

<210> SEQ ID NO 41
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 41
ctgattttct ct                                                         12

<210> SEQ ID NO 42
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 42
actgtttttt tctcttga                                                   18
```

```
-continued

<210> SEQ ID NO 43
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 43
atgaaggctc acgaca                                                       16

<210> SEQ ID NO 44
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 44
gaaggtaatc ttag                                                         14

<210> SEQ ID NO 45
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 45
gattaaagtg aacat                                                        15
```